(12) United States Patent
Castro Pichel et al.

(10) Patent No.: US 9,334,265 B2
(45) Date of Patent: *May 10, 2016

(54) 3-AMINO-PYRAZOLE DERIVATIVES USEFUL AGAINST TUBERCULOSIS

(71) Applicant: GLAXO GROUP LIMITED, Brentford, Middlesex (GB)

(72) Inventors: Julia Castro Pichel, Madrid (ES); Raquel Fernandez Menendez, Madrid (ES); Esther Pilar Fernandez Velando, Madrid (ES); Silvia Gonzalez Del Valle, Madrid (ES)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/639,241

(22) Filed: Mar. 5, 2015

(65) Prior Publication Data

US 2015/0307485 A1    Oct. 29, 2015

Related U.S. Application Data

(63) Continuation of application No. 14/295,589, filed on Jun. 4, 2014, now Pat. No. 9,000,181, which is a continuation of application No. 13/878,889, filed as application No. PCT/EP2011/067705 on Oct. 11, 2011, now Pat. No. 8,779,153.

(30) Foreign Application Priority Data

Oct. 13, 2010 (EP) .................................... 10382266

(51) Int. Cl.
| | | |
|---|---|---|
| *A61K 31/44* | (2006.01) | |
| *C07D 285/12* | (2006.01) | |
| *C07D 417/14* | (2006.01) | |
| *C07D 471/04* | (2006.01) | |

(52) U.S. Cl.
CPC ............ *C07D 417/14* (2013.01); *C07D 471/04* (2013.01)

(58) Field of Classification Search
None
See application file for complete search history.

(56) References Cited

U.S. PATENT DOCUMENTS 8,779,153 B2 *  7/2014  Castro Pichel et al. ....... 548/138
9,000,181 B2 *  4/2015  Fernandez Menendez et al. ............................ 548/138

FOREIGN PATENT DOCUMENTS

WO    WO2010058423    5/2010

OTHER PUBLICATIONS

International Search Report issued on parent international application No. PCT/EP2011/057705 filed Oct. 11, 2011.

* cited by examiner

*Primary Examiner* — Heidi Reese
(74) *Attorney, Agent, or Firm* — Robert H. Brink

(57) ABSTRACT

A compound of Formula (I) or a pharmaceutically acceptable salt thereof:

Wherein: Het is a 5 to 10-membered heteroaromatic ring; Either X is N and Y is $CR^5$; or X is C and Y is S; Z is selected from N and CH; $R^1$ is selected from H and $C_{1-2}$alkyl; $R^2$ is selected from H, $C_{1-2}$alkyl, OH, —$CH_2OH$ and $C_{1-2}$alkoxy; Each $R^3$ is independently selected from OH, $C_{1-3}$alkyl, F, Cl, Br, $NH_2$, and $C_{1-3}$alkoxy; $R^4$ is selected from $C_{1-3}$alkyl and halo$C_{1-3}$alkyl; $R^5$ is selected from H, $C_{1-3}$alkyl and halo $C_{1-3}$alkyl; $R^6$ and $R^7$ are either i) each independently selected from H, $C_{1-3}$alkyl and $C_{1-3}$alkoxy; or ii) $R^6$ and $R^7$ together with the ring to which they are attached form a 9-membered bicyclic ring; p is 0-3; and $R^A$ is selected from H and $C_{1-3}$alkyl, compositions containing them, their use in therapy, for example in the treatment of tuberculosis, and methods for the preparation of such compounds, are provided.

7 Claims, No Drawings

3-AMINO-PYRAZOLE DERIVATIVES USEFUL AGAINST TUBERCULOSIS

This application is filed as a continuation application of U.S. Ser. No. 14/295,589, filed on Jun. 4, 2014, which is a continuation of U.S. Ser. No. 13/878,889, filed on Apr. 11, 2013 (now granted as U.S. Pat. No. 8,779,153 on Jul. 15, 2014), which is a National Phase Application of International Application No. PCT/EP2011/067705 filed on Oct. 11, 2011, which claims priority from EP 10382266.4 filed on Oct. 13, 2010.

FIELD OF THE INVENTION

This invention relates to compounds, compositions containing them, their use in therapy, for example in the treatment of tuberculosis, and methods for the preparation of such compounds.

BACKGROUND OF THE INVENTION

Synthetic drugs for treating tuberculosis (TB) have been available for over half a century, but incidences of the disease continue to rise world-wide. In 2004, it is estimated that 24,500 people developed active disease and close to 5,500 died each day from TB (World Health Organization, Global Tuberculosis Control: Surveillance, Planning, Financing. WHO Report 2006, Geneva, Switzerland, ISBN 92-4 156314-1). Co-infection with HIV is driving the increase in incidence (Williams, B. G.; Dye, C. Science, 2003, 301, 1535) and the cause of death in 31% of AIDS patients in Africa can be attributed to TB (Corbett, E. L.; Watt, C. J.; Catherine, J.; Walker, N.; Maher D.; Williams, B. G.; Raviglione, M. C.; Dye, C. Arch. Intl. Med., 2003, 163, 1009, Septkowitz, A.; Raffalli, J.; Riley, T.; Kiehn, T. E.; Armstrong, D. Clin. Microbiol. Rev. 1995, 8, 180). When coupled with the emergence of multi-drug resistant strains of Mycobacterium tuberculosis (MDR-TB), the scale of the problem is amplified. It is now more than a decade since the WHO declared TB "a global health emergency" (World Health Organization, Global Tuberculosis Control: Surveillance, Planning, Financing. WHO Report 2006, Geneva, Switzerland, ISBN 92-4 156314-1).

The limitations of tuberculosis therapy and prevention are well-known. The current available vaccine, BCG was introduced in 1921 and fails to protect most people past childhood. Patients who do become infected with active disease currently endure combination therapy with isoniazid (INH), rifampin, pyrazinamide and ethambutol for two months and then continue taking isoniazid and rifampin for a further four months. Daily dosing is required and poor compliance drives the emergence and spread of multi-drug-resistant strains, which are challenging to treat. A recently-published detailed review discusses many aspects of TB such as pathogenesis, epidemiology, drug discovery and vaccine development to date (Nature Medicine, Vol 13(3), pages 263-312).

Shorter courses of more active agents which can be taken less frequently and which present a high barrier to the emergence of resistance, i.e. agents which are effective against multi-drug resistant strains of TB, are urgently required. There is therefore a need to discover and develop new chemical entities to treat TB. Recent synthetic leads are reviewed in: Ballell, L.; Field, R. A.; Duncan, K.; Young, R. J. Antimicrob. Agents Chemother. 2005, 49, 2153.

Lipid metabolism is especially important for the genus Mycobacterium and it represents a well-validated target for the development of selective antitubercular agents. The enzyme which is denoted "InhA" is an NADH-dependent (dependent on the reduced form of nicotinamide adenine dinucleotide), 2-trans enoyl-ACP (acyl carrier protein) reductase of the type 2 fatty acid synthesis (FASII) pathway in Mycobacterium tuberculosis. There is a strong body of evidence indicating that InhA is the primary target of the frontline antitubercular drug isoniazid (INH). Clinical isolates as well as laboratory modified mycobacteria over-expressing InhA show resistance to INH. The drug inhibits InhA enzymatic activity inducing an accumulation of saturated C24-C26 fatty acids and blocking the production of longer molecules, including mycolic acids. This inhibition correlates with mycobacterial cell death.

The essentiality of InhA has also been demonstrated by the use of temperature-sensitive mutants of InhA in Mycobacterium smegmatis, where a shift to the non-permissive temperature results in rapid lysis and cell death.

INH is a bactericidal drug, showing specific activity against Mycobacterium tuberculosis, and is part of the first-line drug combination regimen for antitubercular therapy. INH is activated within the mycobacterial cell by the KatG catalase. The activated form is thought to react covalently with NADH within the InhA active site to form an inhibitory adduct. X-Ray structures of InhA bound to several inhibitors are available and are being used to design new inhibitors.

In vitro-activated INH forms adducts with NAD(P) cofactors which bind to and inhibit InhA and other enzymes like DHFR (dehydrofolate reductase); the physiological relevance of these interactions in vivo is clear in the case of the enoyl-reductase, but it has been shown to be almost irrelevant in the case of DHFR; the potential role of other possible targets of INH in the antitubercular activity of the drug seems minimal or non-existent.

Resistance to INH has been associated with at least five different genes (KatG, InhA, ahpC, kasA, and ndh); 60-70% of resistant isolates can be directly linked to defects in the KatG gene (often with compensatory mutations in other genes) and less commonly in the InhA structural gene and upstream promoter region.

It is anticipated that a drug targeted at InhA, not requiring activation by KatG, would interact with the enzyme in a different way from the complex NAD-INH, would also have a different pharmacological profile from INH, would kill the majority of the current INH$^R$ (isoniazid-resistant) strains and would replace INH in the existing therapy against Mycobacterium tuberculosis.

PCT Patent Application No. PCT/EP2010/002265 discloses a class of compounds which are targeted at InhA and do not require activation by KatG, and which exhibit activity against Mycobacterium tuberculosis H37Rv.

DETAILED DESCRIPTION OF THE INVENTION

The present invention provides a compound of Formula (I) or a pharmaceutically acceptable salt thereof:

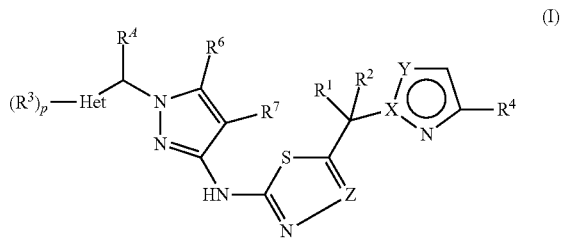

Wherein:
Het is a 5 to 10-membered heteroaromatic ring;
Either X is N and Y is CR$^5$; or X is C and Y is S;
Z is selected from N and CH;
R$^1$ is selected from H and C$_{1-2}$alkyl;

$R^2$ is selected from H, $C_{1-2}$alkyl, OH, —$CH_2OH$ and $C_{1-2}$alkoxy;

Each $R^3$ is independently selected from OH, $C_{1-3}$alkyl, F, Cl, Br, $NH_2$, and $C_{1-3}$alkoxy;

$R^4$ is selected from $C_{1-3}$alkyl and halo$C_{1-3}$alkyl;

$R^5$ is selected from H, $C_{1-3}$alkyl and halo$C_{1-3}$alkyl;

$R^6$ and $R^7$ are either i) each independently selected from H, $C_{1-3}$alkyl and $C_{1-3}$alkoxy; or ii) $R^6$ and $R^7$ together with the ring to which they are attached form a 9-membered bicylic ring;

p is 0-3; and $R^A$ is selected from H and $C_{1-3}$alkyl.

In one aspect of the invention there is provided a compound of Formula (I) as defined hereinabove.

The invention further provides a pharmaceutical composition comprising a compound of Formula (I), or a pharmaceutically acceptable salt thereof, and one or more pharmaceutically acceptable carriers, excipients or diluents.

In one aspect of the invention there is provided a pharmaceutical composition comprising a compound of Formula (I) and one or more pharmaceutically acceptable carriers, excipients or diluents.

The invention also provides a method of treatment of tuberculosis in mammals, particularly in man, which method comprises the administration to a mammal in need of such treatment an effective amount of a compound of Formula (I), or a pharmaceutically acceptable salt thereof.

In one aspect of the invention there is provided a method of treatment of tuberculosis in mammals, particularly in man, which method comprises the administration to a mammal in need of such treatment an effective amount of a compound of Formula (I).

The invention further provides a compound of Formula (I), or a pharmaceutically acceptable salt thereof, for use in therapy.

In one aspect of the invention there is provided a compound of Formula (I) for use in therapy.

The invention yet further provides a compound of Formula (I), or a pharmaceutically acceptable salt thereof, for use in the treatment of tuberculosis in mammals, particularly in man.

In one aspect of the invention there is provided a compound of Formula (I) for use in the treatment of tuberculosis in mammals, particularly in man.

The invention still further provides the use of a compound of Formula (I), or a pharmaceutically acceptable salt thereof, in the manufacture of a medicament for use in the treatment of tuberculosis in mammals, particularly in man.

In one aspect of the invention there is provided the use of a compound of Formula (I) in the manufacture of a medicament for use in the treatment of tuberculosis in mammals, particularly in man.

The invention also provides a pharmaceutical composition comprising a compound of Formula (I), or a pharmaceutically acceptable salt thereof, and one or more pharmaceutically acceptable carriers, excipients or diluents, for use in the treatment of tuberculosis in mammals, particularly in man.

In one aspect of the invention there is provided a pharmaceutical composition comprising a compound of Formula (I) and one or more pharmaceutically acceptable carriers, excipients or diluents, for use in the treatment of tuberculosis in mammals, particularly in man.

In one aspect of the invention, the absolute stereochemistry of the compound of Formula (I), or a pharmaceutically acceptable salt thereof, is as shown in Formula (I*):

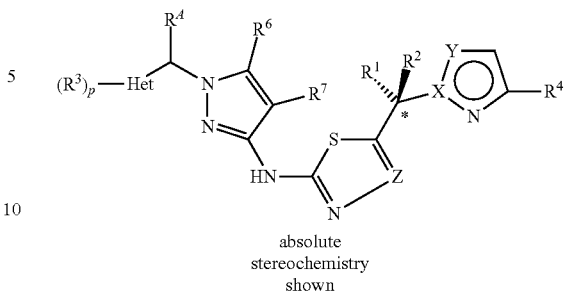

(I*)

absolute stereochemistry shown

In one aspect of the invention, Het is selected from pyridyl, thiazolyl, quinolinyl, oxazolyl, imidazopyridyl, pyrazolyl, isoxazolyl, imidazolyl and isothiazolyl. In another aspect, Het is selected from pyridyl, thiazolyl, quinolinyl, oxazolyl, imidazopyridyl, pyrazolyl, isoxazolyl and imidazolyl. In a further aspect, Het is selected from pyridyl, thiazolyl quinolinyl, oxazolyl, imidazopyridyl and pyrazolyl. In a yet further aspect, Het is selected from pyridyl and thiazolyl, for example pyridyl. In one embodiment, Het is 2-pyridyl or 3-pyridyl. In another embodiment, Het is 2-pyridyl. In one embodiment, Het is 4-thiazolyl.

In one aspect of the invention, X is N and Y is $CR^5$.

In one aspect of the invention, X is C and Y is S.

In one aspect of the invention, Z is N.

In one aspect of the invention, $R^1$ is $C_{1-2}$alkyl, for example $CH_3$.

In one aspect of the invention, $R^2$ is selected from H, $C_{1-2}$alkyl, OH and $C_{1-2}$alkoxy. In another aspect, $R^2$ is selected from H and OH. In another aspect of the invention, when X is N and Y is $CR^5$, $R^2$ is selected from H, $C_{1-2}$alkyl and —$CH_2OH$. In yet another aspect, when X is N and Y is $CR^5$, $R^2$ is H.

In embodiments of the invention in which $R^1$ and $R^2$ are different from each other, the carbon atom to which groups $R^1$ and $R^2$ are bonded (labelled "*" in Formula (I*) above) is a stereogenic centre. Such embodiments may be present as a mixture of isomers, for example a racemic mixture of enantiomers, or present as a single isomer, for example, in at least 98% enantiomeric excess (e.e.). In one embodiment, the invention provides an isomer of a compound of the invention wherein $R^1$ and $R^2$ are different from each other, for example wherein $R^1$ is $CH_3$ and $R^2$ is H or OH. In a further embodiment, the invention provides a compound of Formula (I) or a pharmaceutically acceptable salt thereof having the absolute chemistry shown in Formula (I*).

In one aspect, the invention provides compounds of the Formula (I) or pharmaceutically acceptable salts thereof in which the stereogenic centre marked * in Formula (I-S) below is in the (S)-configuration:

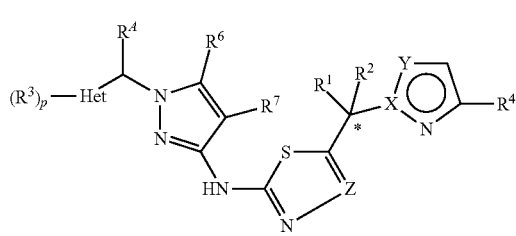

(I-S)

In one aspect, compounds which are useful in the present invention include those mentioned in the Examples and their pharmaceutically acceptable salts.

In one aspect of the invention, each $R^3$ is independently selected from OH, $CH_3$, F, Cl, Br, $NH_2$, MeO and EtO. In one aspect of the invention at least one $R^3$ group is $CH_3$ or F. In one aspect of the invention, p is 1 or 2. In another aspect, p is 1. In one aspect of the invention, when Het is 2-pyridyl, one $R^3$ group is F, for example at the 3-position, and the other $R^3$ groups are absent (p is 1). In another aspect, when Het is 2-pyridyl, one $R^3$ group is F, for example at the 3-position, and another $R^3$ group is F or $CH_3$, for example at the 4-position, and the other $R^3$ group is absent (p is 2). In another aspect of the invention, when Het is 4-thiazolyl, one $R^3$ group is attached at the 2-position, for example $CH_3$, and the other $R^3$ groups are absent (p is 1).

In one aspect of the invention, $R^4$ is selected from $CH_3$, $CF_3$ and $CH_2F$. In another aspect, $R^4$ is $CH_3$.

In one aspect of the invention, $R^5$ is selected from H, $CH_3$, $CF_3$ and $CH_2F$. In another aspect, $R^5$ is selected from H and $CH_3$.

In one aspect of the invention, $R^6$ and $R^7$ are each independently selected from H, $C_{1-3}$alkyl and $C_{1-3}$alkoxy. In another aspect, $R^6$ and $R^7$ are each independently selected from H and $C_{1-3}$alkyl, for example from H and $CH_3$. In yet another aspect, $R^6$ is $CH_3$ and $R^7$ is H.

In one aspect of the invention, $R^6$ and $R^7$ together with the ring to which they are attached form a 9-membered bicyclic ring. In one aspect, the 9-membered bicyclic ring is tetrahydroindazole:

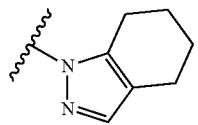 [SMILES: *n1ncc2c1CCCC2]

In another aspect of the invention, the 9-membered bicyclic ring is indazole:

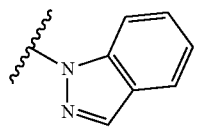 [SMILES: *n1ncc2ccccc21]

In one aspect of the invention, $R^A$ is selected from H and $CH_3$. In another aspect, $R^A$ is H.

It will be appreciated that compounds of the invention can exist in different tautomeric forms. For example, when Het is pyridyl, for example 2-pyridyl, and one $R^3$ is OH, for example 4-OH, compounds of Formula (I) may exist in the 4-pyridinol tautomeric form (a) or the 4-pyridinone (4-pyridone) tautomeric form (b), or a mixture thereof as follows:

All possible tautomeric forms of the compounds of Formula I are contemplated to be within the scope of the present invention. In one aspect of the invention there is provided a compound of Formula I as defined hereinabove, which is other than a compound wherein Het is 2-pyridyl and one $R^3$ is 4-OH and Het is in the 4-pyridinone (4-pyridone) tautomeric form (b).

In another aspect, compounds which are useful in the present invention include:

1: 5-[1-(3,5-dimethyl-1H-pyrazol-1-yl)ethyl]-N-{1-[(6-methyl-2-pyridinyl)methyl]-1H-pyrazol-3-yl}-1,3,4-thiadiazol-2-amine
2: 5-[1-(3,5-dimethyl-1H-pyrazol-1-yl)ethyl]-N-{1-[(3-fluoro-4-methyl-2 pyridinyl)methyl]-1H-pyrazol-3-yl}-1,3,4-thiadiazol-2-amine
3: N-{1-[(3-fluoro-4-methyl-2-pyridinyl)methyl]-1H-pyrazol-3-yl}-5-[1-(3-methyl-1H-pyrazol-1-yl)ethyl]-1,3,4-thiadiazol-2-amine
4: 5-[1-(3,5-dimethyl-1H-pyrazol-1-yl)ethyl]-N-[1-(3-pyridinylmethyl)-1H-pyrazol-3-yl]-1,3,4-thiadiazol-2-amine
5: 5-[1-(3,5-dimethyl-1H-pyrazol-1-yl)ethyl]-N-[1-(2-pyridinylmethyl)-1H-pyrazol-3-yl]-1,3,4-thiadiazol-2-amine
6: 5-[1-(3,5-dimethyl-1H-pyrazol-1-yl)ethyl]-N-{1-[(3-fluoro-2-pyridinyl)methyl]-1H-pyrazol-3-yl}-1,3,4-thiadiazol-2-amine
7: 5-[1-(3,5-dimethyl-1H-pyrazol-1-yl)ethyl]-N-{1-[(2-fluoro-3-pyridinyl)methyl]-1H-pyrazol-3-yl}-1,3,4-thiadiazol-2-amine
8: N-{1-[(5-chloro-6-methyl-3-pyridinyl)methyl]-1H-pyrazol-3-yl}-5-[1-(3,5-dimethyl-1H-pyrazol-1-yl)ethyl]-1,3,4-thiadiazol-2-amine
9: N-{1-[(3,5-dichloro-2-pyridinyl)methyl]-1H-pyrazol-3-yl}-5-[1-(3,5-dimethyl-1H-pyrazol-1-yl)ethyl]-1,3,4-thiadiazol-2-amine
10: N-{1-[(2-fluoro-3-pyridinyl)methyl]-1H-pyrazol-3-yl}-5-[1-(3-methyl-1H-pyrazol-1-yl)ethyl]-1,3,4-thiadiazol-2-amine
11: 5-[1-(3,5-dimethyl-1H-pyrazol-1-yl)ethyl]-N-(1-{[2-(ethyloxy)-3-pyridinyl]methyl}-1H-pyrazol-3-yl)-1,3,4-thiadiazol-2-amine
12: 1-[5-({1-[(3,5-difluoro-2-pyridinyl)methyl]-1H-pyrazol-3-yl}amino)-1,3,4-thiadiazol-2-yl]-1-(4-methyl-1,3-thiazol-2-yl)ethanol
13: N-{1-[(3-fluoro-2-pyridinyl)methyl]-1H-pyrazol-3-yl}-5-[1-(3-methyl-1H-pyrazol-1-yl)ethyl]-1,3,4-thiadiazol-2-amine
14: 1-[5-({1-[(3-methyl-2-pyridinyl)methyl]-1H-pyrazol-3-yl}amino)-1,3,4-thiadiazol-2-yl]-1-(4-methyl-1,3-thiazol-2-yl)ethanol
15: 1-(4-methyl-1,3-thiazol-2-yl)-1-(5-{[1-(2-quinolinylmethyl)-1H-pyrazol-3-yl]amino}-1,3,4-thiadiazol-2-yl)ethanol

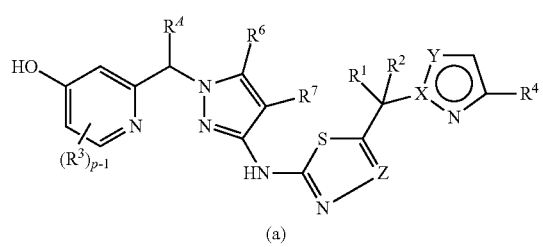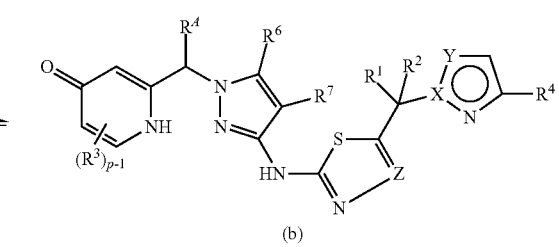

(a)            (b)

16: 2-{[3-({5-[1-hydroxy-1-(4-methyl-1,3-thiazol-2-yl)ethyl]-1,3,4-thiadiazol-2-yl}amino)-1H-pyrazol-1-yl]methyl}-3-pyridinol 17: 1-[5-({1-[(2-amino-1,3-thiazol-4-yl)methyl]-1H-pyrazol-3-yl}amino)-1,3,4-thiadiazol-2-yl]-1-(4-methyl-1,3-thiazol-2-yl)ethanol 18: 1-[5-({1-[(6-fluoro-2-pyridinyl)methyl]-1H-pyrazol-3-yl}amino)-1,3,4-thiadiazol-2-yl]-1-(4-methyl-1,3-thiazol-2-yl)ethanol 19: 1-(5-{[1-(1-isoquinolinylmethyl)-1H-pyrazol-3-yl]amino}-1,3,4-thiadiazol-2-yl)-1-(4-methyl-1,3-thiazol-2-yl)ethanol 20: 1-(4-methyl-1,3-thiazol-2-yl)-1-(5-{[1-(8-quinolinylmethyl)-1H-pyrazol-3-yl]amino}-1,3,4-thiadiazol-2-yl)ethanol 21: 1-(4-methyl-1,3-thiazol-2-yl)-1-[5-({1-[(2-methyl-1,3-thiazol-4-yl)methyl]-1H-pyrazol-3-yl}amino)-1,3,4-thiadiazol-2-yl]ethanol 22: 1-[5-({1-[(5-methyl-3-isoxazolyl)methyl]-1H-pyrazol-3-yl}amino)-1,3,4-thiadiazol-2-yl]-1-(4-methyl-1,3-thiazol-2-yl)ethanol 23: 5-[1-(3-methyl-1H-pyrazol-1-yl)ethyl]-N-{1-[(2-methyl-1,3-thiazol-4-yl)methyl]-1H-pyrazol-3-yl}-1,3,4-thiadiazol-2-amine 24: 1-(5-{[1-(imidazo[1,2-a]pyridin-2-ylmethyl)-1H-pyrazol-3-yl]amino}-1,3,4-thiadiazol-2-yl)-1-(4-methyl-1,3-thiazol-2-yl)ethanol 25: 1-[5-({1-[(1-methyl-1H-pyrazol-4-yl)methyl]-1H-pyrazol-3-yl}amino)-1,3,4-thiadiazol-2-yl]-1-(4-methyl-1,3-thiazol-2-yl)ethanol 26: 1-[5-({1-[(3,5-dimethyl-4-isoxazolyl)methyl]-1H-pyrazol-3-yl}amino)-1,3,4-thiadiazol-2-yl]-1-(4-methyl-1,3-thiazol-2-yl)ethanol 27: N-{1-[(3,5-dimethyl-4-isoxazolyl)methyl]-1H-pyrazol-3-yl}-5-[1-(3-methyl-1H-pyrazol-1-yl)ethyl]-1,3,4-thiadiazol-2-amine 28: 1-[5-({1-[(3-fluoro-2-pyridinyl)methyl]-5-methyl-1H-pyrazol-3-yl}amino)-1,3,4-thiadiazol-2-yl]-1-(4-methyl-1,3-thiazol-2-yl)ethanol 29: N-{1-[(3-fluoro-2-pyridinyl)methyl]-5-methyl-1H-pyrazol-3-yl}-5-[1-(3-methyl-1H-pyrazol-1-yl)ethyl]-1,3,4-thiadiazol-2-amine 30: 1-{5-[(1-{[5-(ethyloxy)-3-fluoro-2-pyridinyl]methyl}-1H-pyrazol-3-yl)amino]-1,3,4-thiadiazol-2-yl}-1-(4-methyl-1,3-thiazol-2-yl)ethanol 31: 1-{5-[(1-{[3,5-dimethyl-4-(methyloxy)-2-pyridinyl]methyl}-1H-pyrazol-3-yl)amino]-1,3,4-thiadiazol-2-yl}-1-(4-methyl-1,3-thiazol-2-yl)ethanol 32: 1-[5-({1-[(3,5-difluoro-4-pyridinyl)methyl]-1H-pyrazol-3-yl}amino)-1,3,4-thiadiazol-2-yl]-1-(4-methyl-1,3-thiazol-2-yl)ethanol 33: 3-fluoro-2-{[3-({5-[1-hydroxy-1-(4-methyl-1,3-thiazol-2-yl)ethyl]-1,3,4-thiadiazol-2-yl}amino)-1H-pyrazol-1-yl]methyl}-4(1H)-pyridinone 34: N-{1-[(3-fluoro-2-pyridinyl)methyl]-1H-pyrazol-3-yl}-5-[1-(4-methyl-1,3-thiazol-2-yl)ethyl]-1,3,4-thiadiazol-2-amine 35: 5-[1-(3,5-dimethyl-1H-pyrazol-1-yl)ethyl]-N-{1-[1-(3-fluoro-2-pyridinyl)ethyl]-1H-pyrazol-3-yl}-1,3,4-thiadiazol-2-amine 36: 5-[1-(3,5-dimethyl-1H-pyrazol-1-yl)ethyl]-N-(1-{[6-(ethyloxy)-2-pyridinyl]methyl}-1H-pyrazol-3-yl)-1,3,4-thiadiazol-2-amine 37: 1-[5-({1-[(3-fluoro-4-methyl-2-pyridinyl)methyl]-1H-pyrazol-3-yl}amino)-1,3,4-thiadiazol-2-yl]-1-(4-methyl-1,3-thiazol-2-yl)ethanol 38: 1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol 39: N-{1-[(3-fluoro-2-pyridinyl)methyl]-1H-pyrazol-3-yl}-5-[(1R)-1-(3-methyl-1H-pyrazol-1-yl)ethyl]-1,3,4-thiadiazol-2-amine 40: N-{1-[(3-fluoro-2-pyridinyl)methyl]-1H-pyrazol-3-yl}-5-[(1S)-1-(3-methyl-1H-pyrazol-1-yl)ethyl]-1,3,4-thiadiazol-2-amine 41: (1S)-1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol 42: (1R)-1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol 43: (1S)-1-(4-methyl-1,3-thiazol-2-yl)-1-[5-({1-[(2-methyl-1,3-thiazol-4-yl)methyl]-1H-pyrazol-3-yl}amino)-1,3,4-thiadiazol-2-yl]ethanol 44: (1R)-1-(4-methyl-1,3-thiazol-2-yl)-1-[5-({1-[(2-methyl-1,3-thiazol-4-yl)methyl]-1H-pyrazol-3-yl}amino)-1,3,4-thiadiazol-2-yl]ethanol 45: 1-(4-methyl-1,3-thiazol-2-yl)-1-[5-({1-[(2-methyl-1,3-thiazol-4-yl)methyl]-1H-indazol-3-yl}amino)-1,3,4-thiadiazol-2-yl]ethanol 46: N-{5-[1-(3-methyl-1H-pyrazol-1-yl)ethyl]-1,3,4-thiadiazol-2-yl}-1-[(2-methyl-1,3-thiazol-4-yl)methyl]-1H-indazol-3-amine 47: 1-(4-ethylthiazol-2-yl)-1-(5-((1-((2-methylthiazol-4-yl)methyl)-1H-pyrazol-3-yl)amino)-1,3,4-thiadiazol-2-yl)ethanol; or a pharmaceutically acceptable salt thereof.

In one aspect, the invention provides a compound selected from:

40: N-{1-[(3-fluoro-2-pyridinyl)methyl]-1H-pyrazol-3-yl}-5-[(1S)-1-(3-methyl-1H-pyrazol-1-yl)ethyl]-1,3,4-thiadiazol-2-amine 41: (1S)-1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol 43: (1S)-1-(4-methyl-1,3-thiazol-2-yl)-1-[5-({1-[(2-methyl-1,3-thiazol-4-yl)methyl]-1H-pyrazol-3-yl}amino)-1,3,4-thiadiazol-2-yl]ethanol;

or a pharmaceutically acceptable salt thereof.

In one aspect, the invention provides a compound selected from:

41: (1S)-1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol 43: (1S)-1-(4-methyl-1,3-thiazol-2-yl)-1-[5-({1-[(2-methyl-1,3-thiazol-4-yl)methyl]-1H-pyrazol-3-yl}amino)-1,3,4-thiadiazol-2-yl]ethanol.

In another aspect, the invention provides a compound of Examples 40, 41 or 43 as a single enantiomer, for example, in at least 98% enantiomeric excess (e.e.).

In one aspect the invention provides a process for the preparation of a compound of Formula (Ia)

Wherein:

Het is a 5 to 10-membered heteroaromatic ring;

Either X is N and Y is $CR^5$; or X is C and Y is S;

Z is N;

$R^1$ is selected from H and $C_{1-2}$alkyl;

$R^2$ is selected from H, $C_{1-2}$alkyl, OH, —$CH_2OH$ and $C_{1-2}$alkoxy;

Each $R^3$ is independently selected from OH, $C_{1-3}$alkyl, F, Cl, Br, $NH_2$, and $C_{1-3}$alkoxy;

$R^4$ is selected from $C_{1-3}$alkyl and halo$C_{1-3}$alkyl;

$R^5$ is selected from H, $C_{1-3}$alkyl and halo$C_{1-3}$alkyl;
$R^6$ and $R^7$ are either
i) each independently selected from H, $C_{1-3}$alkyl and $C_{1-3}$alkoxy; or
ii) $R^6$ and $R^7$ together with the ring to which they are attached form a 9-membered bicylic ring;
p is 0-3; and
$R^4$ is selected from H and $C_{1-3}$alkyl;
comprising the step of reacting of compound of Formula (II) with a compound of Formula (III):

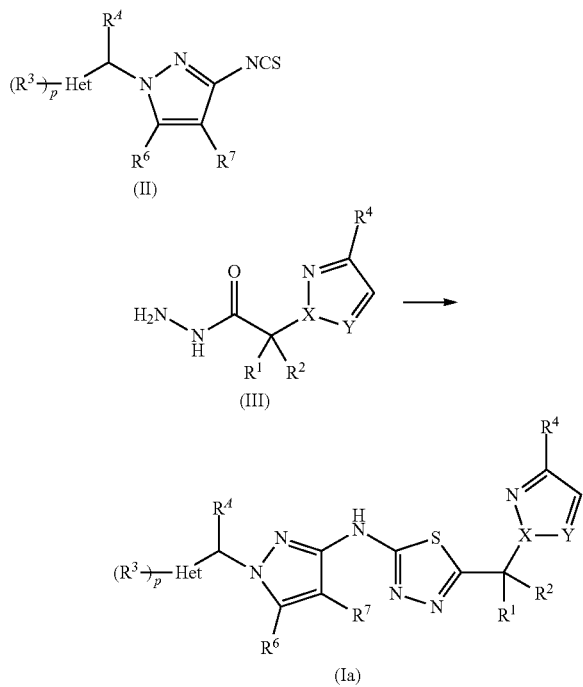

In another aspect, the compound of Formula (II) is reacted with the compound of Formula (III) in a suitable solvent such as DCM or ethanol. In another aspect the process of preparing a compound of Formula (Ia) comprises the step of reacting a hydrazinecarbothioamide intermediate prepared from the reaction of a compound of Formula (II) with the compound of Formula (III) with a dehydrating reagent, such as $H_2SO_4$ or $POCl_3$.

TERMS AND DEFINITIONS

The term "5 to 10-membered heteroaromatic ring" as used herein refers to a 5 to 10-membered monocyclic aromatic ring or a fused 8 to 10-membered bicyclic aromatic ring, the monocylic or bicyclic ring containing 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such bicyclic aromatic rings include quinolinyl, isoquinolinyl, imidazopyridyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and the like.

The term "9-membered bicyclic ring" as used herein refers to a fused bicyclic ring which, in one embodiment, is formed by $R^6$ and $R^7$ together with the pyrazolyl ring to which they are attached. The fused bicyclic ring may be either i) fully aromatic or ii) partially saturated wherein the pyrazolyl ring is aromatic and the ring fused thereto is either saturated or unsaturated. Examples of fully aromatic rings include indazole. Examples of partially saturated rings include tetrahydroindazole.

The term "$C_{1-2}$alkyl" as used herein refers to an alkyl group having 1 or 2 carbon atoms. $C_{1-2}$alkyl groups are methyl (Me) or ethyl (Et).

The term "$C_{1-3}$alkyl" as used herein refers to a straight or branched chain alkyl group having 1 to 3 carbon atoms. Examples of $C_{1-3}$alkyl groups include methyl (Me), ethyl (Et), n-propyl (nPr) and isopropyl (iPr).

The term "$C_{1-4}$alkyl" as used herein refers to a straight or branched chain alkyl group having 1 to 4 carbon atoms. Examples of $C_{1-4}$alkyl groups include methyl (Me), ethyl (Et), propyl (Pr) (for example n-propyl, iso-propyl), butyl (Bu) (for example n-butyl, sec-butyl, iso-butyl, tert-butyl (t-Bu)).

The term "$C_{1-2}$alkoxy" as used herein refers to an alkoxy group having 1 to 2 carbon atoms. $C_{1-2}$alkoxy groups are methoxy (MeO) or ethoxy (EtO).

The term "$C_{1-3}$alkoxy" as used herein refers to a straight or branched chain alkoxy group having 1 to 3 carbon atoms. Examples of $C_{1-3}$alkoxy groups include, methoxy (MeO), ethoxy (EtO), n-propoxy (nPrO) and isopropoxy (iPrO).

The term 'halo$C_{1-3}$alkyl' as used herein refers to a $C_{1-3}$alkyl group as defined herein wherein at least one hydrogen atom is replaced with halogen. Examples of such groups include fluoromethyl ($CH_2F$), trifluoromethyl ($CF_3$), fluoroethyl($CH_2CH_2F$), trifluoroethyl ($CH_2CF_3$) and the like.

The term "halo" as used herein refers to fluoro, chloro, bromo and iodo groups. In one aspect, the term "halo" as used herein refers to fluoro, chloro and bromo groups. In another aspect, the term "halo" as used herein refers to chloro, bromo and iodo groups.

The term "compounds of the invention" as used herein means a compound of Formula (I) or a pharmaceutically acceptable salt thereof. The term "a compound of the invention" means any one of the compounds of the invention as defined above.

Furthermore, it will be understood that phrases such as "a compound of Formula (I) or a pharmaceutically acceptable salt thereof" or "compounds of the invention" are intended to encompass the compound of Formula (I), a pharmaceutically acceptable salt or solvate of the compound of Formula (I), or any pharmaceutically acceptable combination of these. Thus by way of non-limiting example used here for illustrative purpose, "a compound of Formula (I) or a pharmaceutically acceptable salt thereof" encompasses a pharmaceutically acceptable salt of a compound of Formula (I) which is present as a solvate, and this phrase also encompasses a mixture of a compound of Formula (I) and a salt of a compound of Formula (I).

It will be appreciated by those skilled in the art that whilst certain compounds of the invention can form pharmaceutically acceptable salts with an acid or a base, certain other compounds of the invention may not readily form such salts. It will be appreciated that all possible pharmaceutically acceptable salts of a compound of Formula (I) are contemplated to be within the scope of the present invention.

It will be further appreciated that all crystalline forms, polymorphs and enantiomers of the compounds of the invention, or mixtures thereof, are contemplated to be within the scope of the present invention. Unless otherwise specified (for example when the absolute stereochemistry is shown), for compounds of the invention which possess at least one stereocentre, and which can therefore form enantiomers (for example, when $R^1$ and $R^2$ are different from one another, e.g. when $R^1$ is as defined for Formula (I) and $R^2$ represents hydroxy (OH)), the compound can contain a mixture of enantiomers, for example a 1:1 mixture of enantiomers, i.e. a racemic mixture of enantiomers. These may be separated using conventional techniques such as chiral HPLC. For an isomer of compound of the invention for which the absolute stereochemistry is stated or which is otherwise described as a single enantiomer, said isomer of a compound of the invention has, in one embodiment, at least 80% e.e. In another embodiment, said isomer of a compound of the invention has at least 90% e.e., for example at least 95% e.e. In another embodiment said isomer of compound of the invention corresponds to at least 98% e.e, for example at least 99% e.e.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of Formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of a compound of Formula (I) or pharmaceutically acceptable salt and/or solvate thereof.

COMPOUND PREPARATION

The general procedures used to synthesise the compounds of Formula (I), are described in reaction Schemes 1-14 and are illustrated in the Examples.

Preparation of Compounds of Formula (I)

Compounds of Formula (Ia) which are thiadiazole compounds of Formula (I) wherein Z is
N may be prepared according to Scheme 1a by reaction of an isothiacyanate of Formula (II), wherein Het, p, $R^3$, $R^4$, $R^6$ and $R^7$ are as for Formula (I), and an hydrazide of Formula (III), wherein $R^1$, $R^2$ and $R^4$ are as for Formula (I), via a hydrazinecarbothioamide intermediate which can either be isolated and purified, or employed directly in the next step without purification.

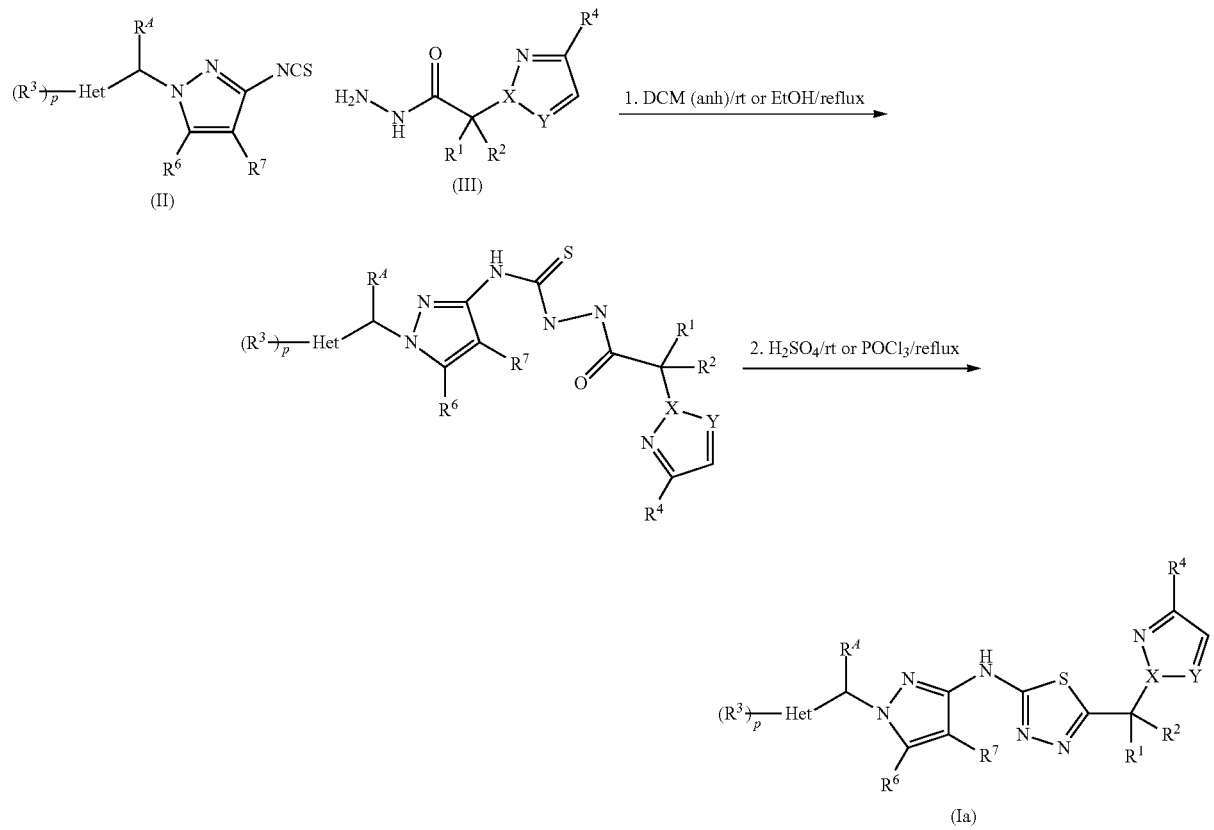

Compounds of Formula (Ib) which are thiazole-pyrazole compounds of Formula (I) wherein Z is CH, X is N and Y is $CR^5$, may be prepared according to Scheme 1 b by reaction of an amine of Formula (IIb), wherein $R^3$, p, $R^6$, $R^7$ and $R^A$ are as for Formula (I) and an halogenated thiazole-pyrazole of Formula (IIIb), wherein $R^1$, $R^2$, $R^4$ and $R^5$ are as for Formula (I), respectively.

Scheme 1b

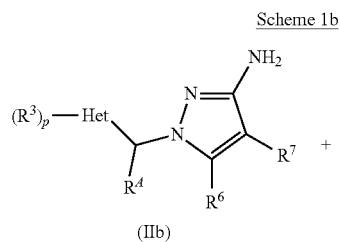

(IIb)

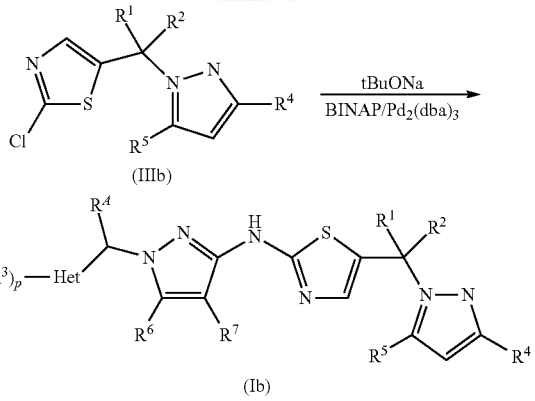

Compounds of Formula (Ic) which are thiazole-thiazole compounds of Formula (I) wherein Z is CH, X is C, Y is S, $R^1$ is methyl and $R^2$ is OH, may be prepared according to Scheme 1c, wherein throughout the scheme, $R^3$, p, $R^4$, $R^6$, $R^{7'}$ Het, and $R^A$ are as for Formula (I).

Scheme 1c

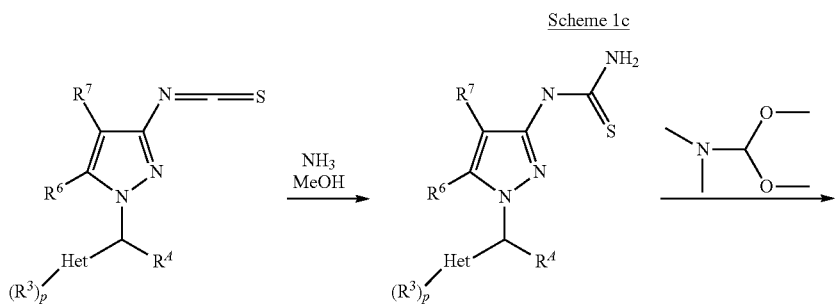

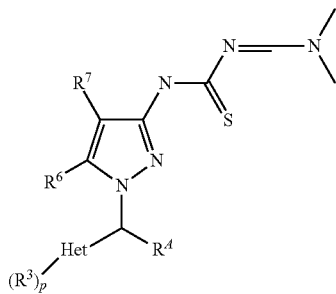

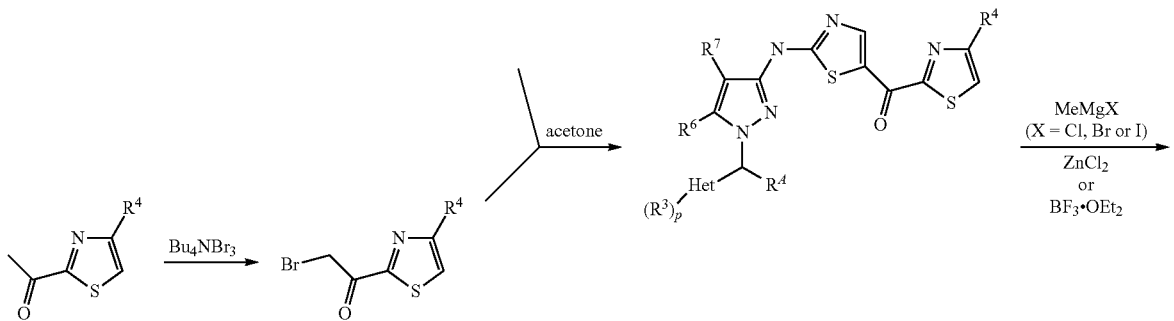

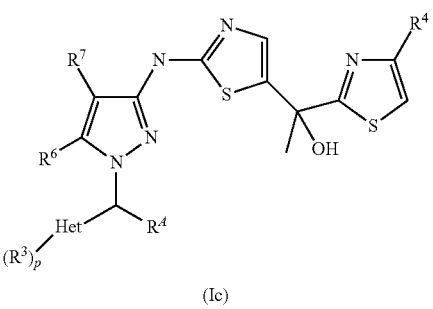

(Ic)

For compounds of Formula (I) wherein at least one $R^3$ group is $NH_2$, the reaction in Schemes 1a, 1b or 1c may be performed wherein the $NH_2$ group(s) is/are protected in the form of a suitable protecting group such as an amide or a carbamate, for example to give rise to compounds of Formula (X) hereinabove. The protecting group can subsequently be removed under standard conditions to provide compounds of Formula (I).

Synthesis of Isothiacyanate Intermediates of Formula (II)

Isothiacyanate intermediates of Formula (II), wherein p, $R^3$ and $R^6$ are as for Formula (I), may be prepared from 3-amino pyrazole intermediates of Formula (IV) (which is the same as compound IIb), wherein p, $R^3$, $R^A$, $R^6$ and $R^7$ are as for Formula (I), as shown in Scheme 2.

Scheme 2

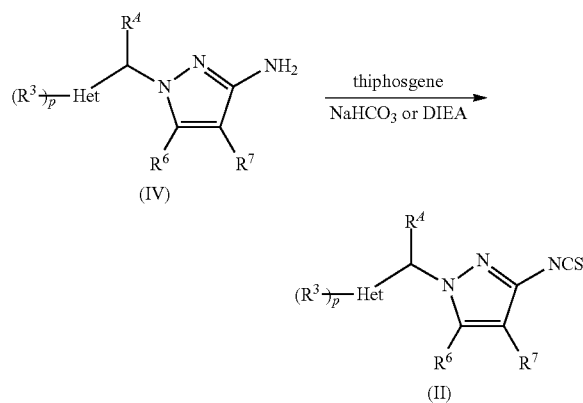

3-Amino pyrazole intermediates of Formula (IV) can be prepared from protected intermediates of the Formula (V), wherein p, $R^3$, $R^A$, $R^6$ and $R^7$ are as for Formula (I), or intermediates of Formula (VI), wherein p, $R^3$, $R^A$, $R^6$ and $R^7$ are as for Formula (I), as shown in Schemes 3 and 4 respectively.

Scheme 3

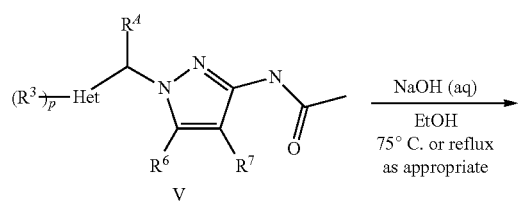

Scheme 4

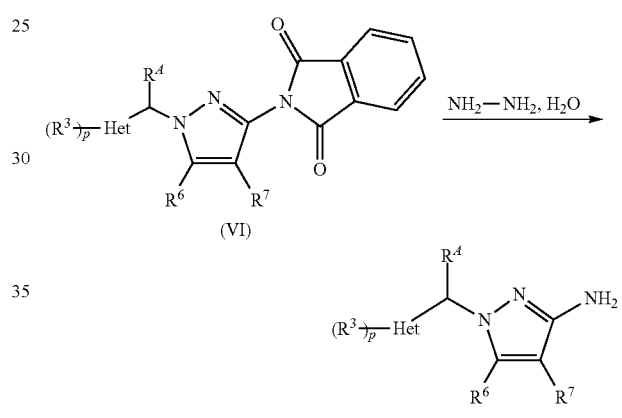

Protected 3-amino pyrazole compounds of Formula (V) may be prepared from a reaction between a 3-acetylamino pyrazole compound of the Formula (VII), wherein $R^6$ and $R^7$ are as for Formula (I), and a commercially available heteroaryl chloride compound, a heteroaryl mesylate (OMs) compound or a heteroaryl bromide compound, wherein p, $R^3$ and $R^A$ are as for Formula (I), as shown in Scheme 5.

Scheme 5

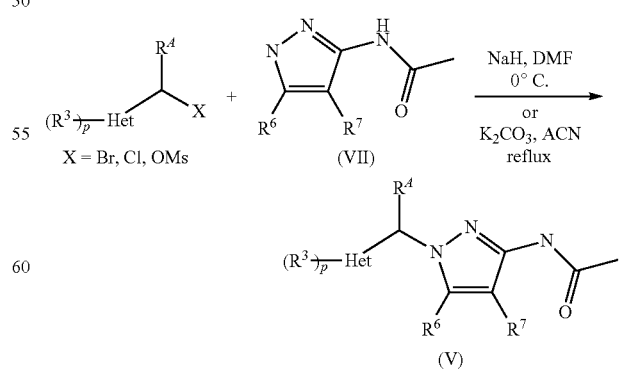

Protected 3-amino pyrazole intermediates of Formula (VI) may be prepared from N-phthalimide intermediates of the Formula (VIII), wherein $R^6$ and $R^7$ are as for Formula (I), and a heteroaryl bromide, chloride or mesylate compound, wherein p, $R^3$ and $R^4$ are as for Formula (I), as shown in Scheme 6.

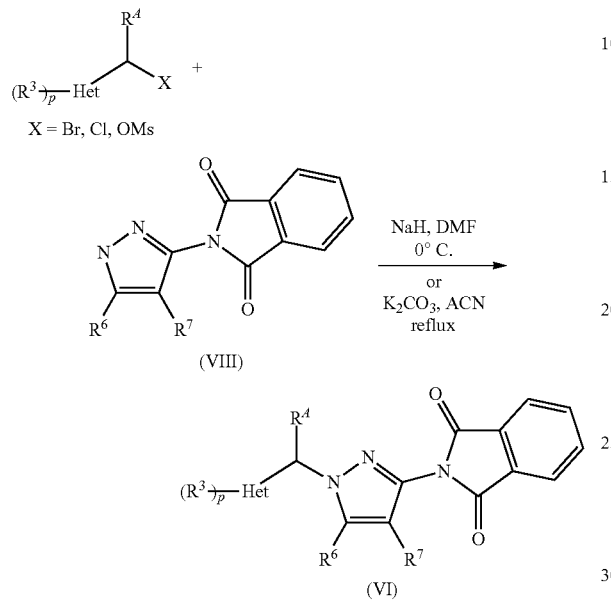

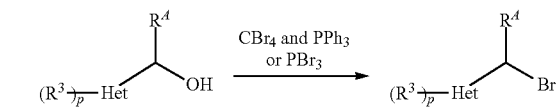

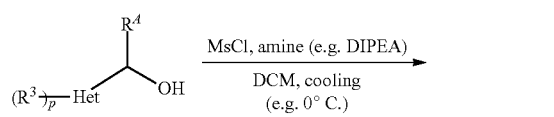

Heteroaryl bromide compounds or heteroaryl mesylate compounds, wherein one $R^3$ group is a protected amine, such as a Boc-protected amine, may be prepared as shown in Schemes 8a and 8b respectively, using Boc anhydride in the presence of a suitable base, such as triethylamine, in a suitable solvent such as THF, followed by conversion of the alcohol moiety to bromide or mesylate. The amine protecting group may be removed at a suitable stage in the preparation of compounds of Formula (I) to provide a compound of Formula (I) in which one $R^3$ group is $NH_2$.

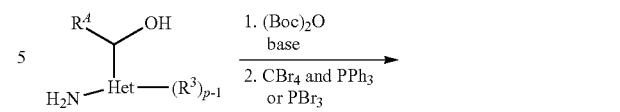

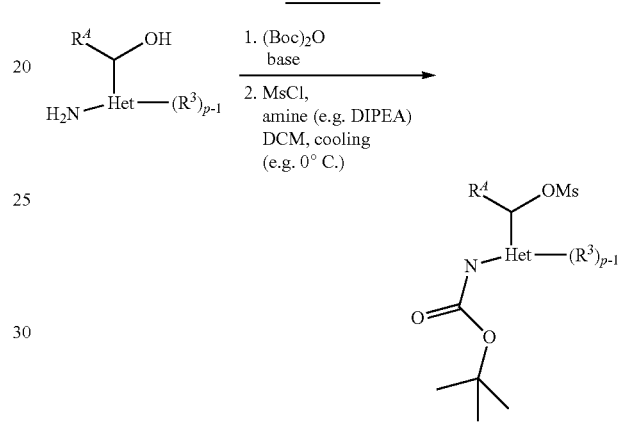

Protected 3-amino pyrazole intermediates of Formula (VII) and Formula (VIII) may be prepared from commercially available 3-amino pyrazoles, wherein $R^6$ is as for Formula (I), as shown in Schemes 9 and 10.

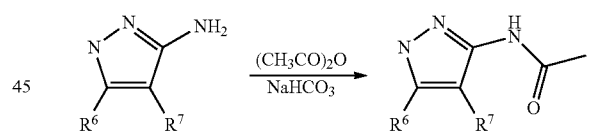

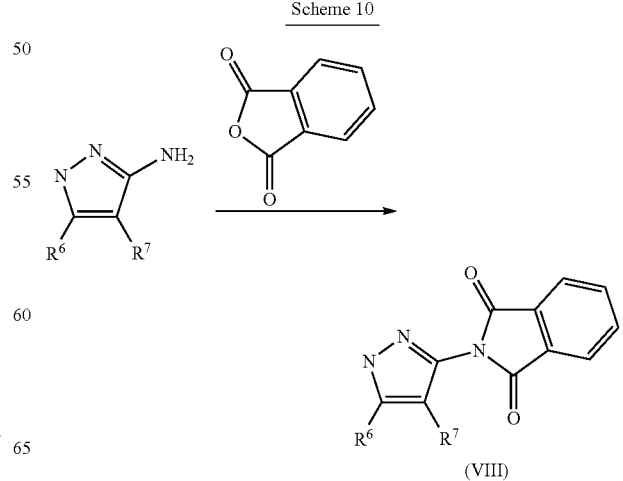

Synthesis of Hydrazine Intermediates of Formula (III)

Hydrazine intermediates of Formula (III), wherein $R^1$, $R^2$ and $R^4$ are as for Formula (I), may be prepared from N-alkyl pyrazole intermediates of the Formula (IX), wherein $R^1$, $R^2$ and $R^4$ are as for Formula (I) and $R^a$ is $C_{1-4}$alkyl, as shown in Scheme 11.

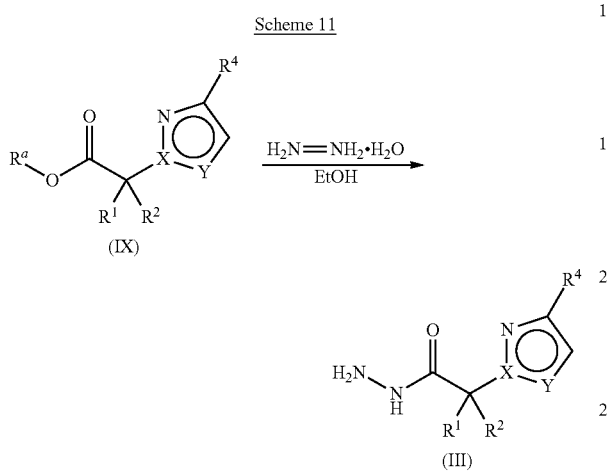

Compounds of Formula (IXa), which are N-alkyl pyrazole compounds of Formula (IX) wherein X is N and Y is $CR^5$ and $R^1$ and $R^4$ are as for Formula (I), $R^2$ is H, $C_{1-2}$alkyl or —$CH_2OH$ and $R^a$ is $C_{1-4}$alkyl, may be prepared as shown in Scheme 12 from a commercially available alkyl bromide, wherein $R^1$ and $R^2$ are as for Formula (I) and $R^a$ is $C_{1-4}$alkyl. Compounds of Formula (IXb), which are 2-alkyl 1,3 thiazole compounds of Formula (IX) wherein X is C and Y is S and $R^1$, $R^2$ and $R^4$ are as for Formula (I), and $R^a$ is $C_{1-4}$alkyl, may be prepared as shown in Scheme 13, starting from a commercially available nitrile compound, wherein $R^1$ and $R^2$ are as for Formula (I) and $R^a$ is $C_{1-4}$alkyl, via a thioamide intermediate compound.

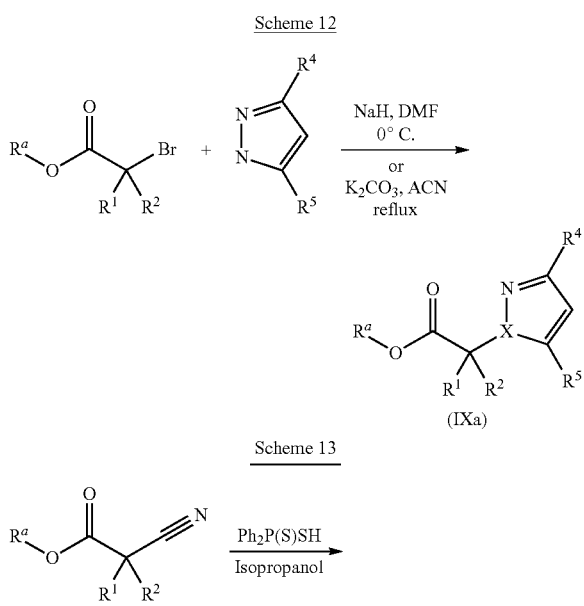

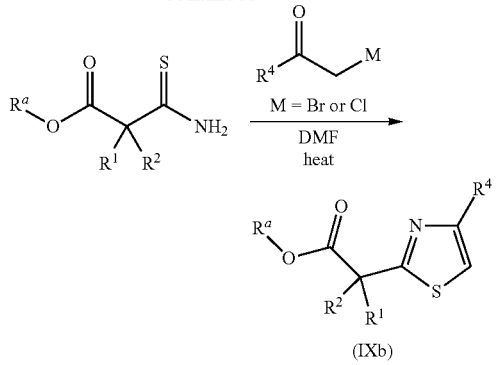

Compounds of Formula (IXb(i)), which are compounds of Formula (IXb) wherein $R^1$ is Me and $R^2$ is OH, may be prepared from compounds of Formula (IXb(ii)), which are compounds of Formula (IXb) wherein $R^1$ is Me and $R^2$ is H, according to Scheme 14.

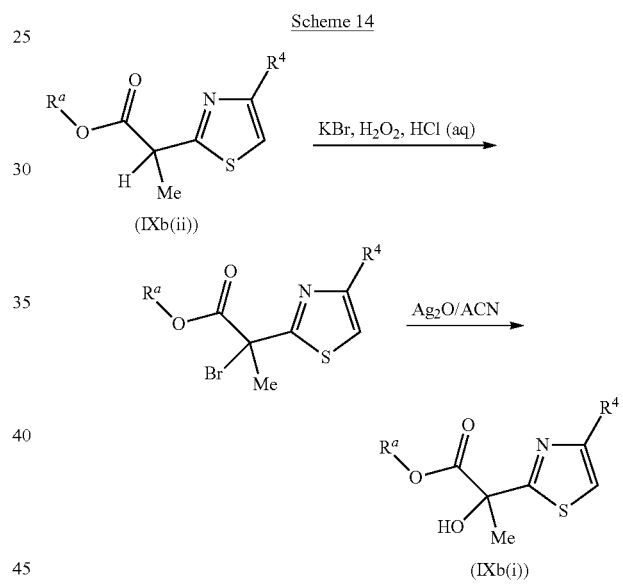

It should be noted that for compound (IXb(ii)) wherein $R^1$ is Me and $R^2$ is H, this compound will undergo slow autooxidation to give compound (IXb(i)) wherein $R^1$ is Me and $R^2$ is OH. Therefore compound (IXb(ii)) is best employed in the next reaction step (Scheme 11) as soon as it has been synthesised, to minimise autooxidation.

Those skilled in the art will appreciate that in the preparation of the compound of Formula (I), it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), N-tert-butyloxycarbonyl (Boc), isopropyloxycarbonyl, cyclohexyloxycarbonyl, ethyloxycarbonyl) and alkyl or aralkyl type protecting groups (e.g. benzyl, trityl, chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate.

It will be readily apparent to those skilled in the art that other compounds of Formula (I) may be prepared using methods analogous to those outlined above, or by reference to the experimental procedures detailed in the Examples provided herein. Further details for the preparation of compounds of Formula (I) are found in the Examples.

Compositions and Formulations

The compounds of the invention may be formulated for administration in any convenient way for use in human or veterinary medicine, by analogy with formulation of antibacterials, or formulation of other antitubercular agents.

The compounds of the invention will normally, but not necessarily, be formulated into pharmaceutical compositions prior to administration to a patient. In one aspect, the invention is directed to a pharmaceutical composition comprising a compound of Formula (I), or a pharmaceutically acceptable salt thereof. In another aspect the invention is directed to a pharmaceutical composition comprising a compound of Formula (I), or a pharmaceutically acceptable salt thereof, and one or more pharmaceutically acceptable carriers, excipients or diluents. The carrier, excipient or diluent must be "acceptable" in the sense of being compatible with the other ingredients of the formulation and not deleterious to the recipient thereof.

A therapeutically effective amount of the compound of the present invention can be determined by methods known in the art. The therapeutically effective quantities will depend on the age and on the general physiological condition of the subject, the route of administration and the pharmaceutical formulation used. The therapeutic doses will generally be between about 1 and 2000 mg/day. The daily dose as employed for acute or chronic human treatment will range from 0.01 to 250 mg/kg body weight, which may be administered in one to four daily doses, for example, depending on the route of administration and the condition of the subject. When the composition comprises dosage units, each unit will contain 1 mg to 2 g of active ingredient.

The present invention is further related to a pharmaceutical composition for the treatment of tuberculosis, comprising the compound of Formula (I) or a pharmaceutically acceptable salt thereof.

The present invention is even further related to a pharmaceutical composition comprising a) 1 to 2000 mg of the compound of Formula (I) or a pharmaceutically acceptable salt thereof, and b) 0.1 to 2 g of one or more pharmaceutically acceptable excipients.

The pharmaceutical compositions of the invention include those in a form adapted for oral, or parenteral use and may be used for the treatment of tuberculosis in mammals including humans.

The pharmaceutical compositions of the invention include those in a form adapted for oral or parenteral use in mammals including humans.

The composition may be formulated for administration by any convenient route. For the treatment of tuberculosis, the compositions may be in the form of tablets, capsules, powders, granules, lozenges, aerosols or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

In one aspect of the invention, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compound of Formula (I), or a pharmaceutically acceptable salt thereof, may be the sole therapeutic agent in the compositions of the invention, or it may be present in the formulation in combination with one or more additional therapeutic agents.

The invention thus provides in a further aspect, a combination comprising a compound of Formula (I), or a pharmaceutically acceptable salt thereof together with one or more additional therapeutic agents. Examples of such one or more additional therapeutic agents are anti-tuberculosis agents including, but not limited to, amikacin, aminosalicylic acid, capreomycin, cycloserine, ethambutol, ethionamide, isoniazid, kanamycin, pyrazinamide, rifamycins (such as rifampin, rifapentine and rifabutin), streptomycin, clarithromycin, azithromycin, oxazolidinones and fluoroquinolones (such as ofloxacin, ciprofloxacin, moxifloxacin and gatifloxacin). Such chemotherapy is determined by the judgment of the treating physician using preferred drug combinations. "First-line" chemotherapeutic agents used to treat a *Mycobacterium tuberculosis* infection that is not drug resistant include isoniazid, rifampin, ethambutol, streptomycin and pyrazinamide. "Second-line" chemotherapeutic agents used to treat a *Mycobacterium tuberculosis* infection that has demonstrated drug resistance to one or more "first-line" drugs include ofloxacin, ciprofloxacin, ethionamide, aminosalicylic acid, cycloserine, amikacin, kanamycin and capreomycin. In addition to the aforementioned, there is a number of new anti-tuberculosis therapeutic agents emerging from clinical studies that may also be employed as the one or more additional therapeutic agents in a combination with a compound of Formula (I), including, but not limited to, TMC-207, OPC-67683, PA-824, LL-3858 and SQ-109.

In another aspect, the invention provides a combination comprising a compound of Formula (I), or a pharmaceutically acceptable salt thereof together with one or more additional therapeutic agents, such as an anti-tuberculosis agent, especially isoniazid (INH), rifampin, pyrazinamide and ethambutol and/or an anti-bacterial agent or an anti-AIDS agent.

In a further aspect, the one or more additional therapeutic agent is, for example, an agent useful for the treatment of tuberculosis in a mammal, therapeutic vaccines, anti-bacterial agents, anti-viral agents; antibiotics and/or agents for the treatment of HIV/AIDS. Examples of such therapeutic agents include isoniazid (INH), ethambutol, rifampin, pirazinamide, streptomycin, capreomycin, ciprofloxacin and clofazimine.

In one aspect, the one or more additional therapeutic agent is a therapeutic vaccine. A compound of Formula (I), or a pharmaceutically acceptable salt thereof, may thus be administered in conjunction with vaccination against mycobacterial infection, in particular vaccination against *Mycobacterium tuberculosis* infection. Existing vaccines against mycobacterial infection include *Bacillus* Calmette Guerin (BCG). Vaccines currently under development for the treatment, prophylaxis or amelioration of mycobacterial infection include: modified BCG strains which recombinantly express additional antigens, cytokines and other agents intended to improve efficacy or safety; attenuated mycobacteria which express a portfolio of antigens more similar to *Mycobacterium tuberculosis* than BCG; and subunit vaccines. Subunit vaccines may be administered in the form of one or more individual protein antigens, or a fusion or fusions of multiple protein antigens, either of which may optionally be adjuvanted, or in the form of a polynucleotide encoding one or more individual protein antigens, or encoding a fusion or fusions of multiple protein antigens, such as where the polynucleotide is administered in an expression vector.

Examples of subunit vaccines include, but are not limited to: M72, a fusion protein derived from the antigens Mtb32a and Mtb39; HyVac-1, a fusion protein derived from antigen 85b and ESAT-6; HyVac-4, a fusion protein derived from antigen 85b and Tb10.4; MVA85a, a modified vaccinia virus Ankara expressing antigen 85a; and Aeras-402, adenovirus 35 expressing a fusion protein derived from antigen 85a, antigen 85b and Tb10.4.

The compound of Formula (I), or a pharmaceutically acceptable salt thereof, may be either i) administered to an individual who has previously been vaccinated against mycobacterial infection; ii) administered to an individual who is subsequently vaccinated against mycobacterial infection; or iii) may be co-administered with a vaccine against mycobacterial infection, either by administering the compound of the invention and the vaccine together in the same dosage form or co-administering the compound of the invention and the vaccine in separate dosage forms.

When a compound of Formula (I), or a pharmaceutically acceptable salt thereof is used in combination with one or more additional therapeutic agents, the dose of the compound or agent may differ from that when the compound or agent is used alone. Appropriate doses will be readily appreciated by those skilled in the art. It will be appreciated that the amount of a compound of the invention and the one or more additional therapeutic agents required for use in treatment will vary with the nature of the condition being treated and the age and the condition of the patient and will be ultimately at the discretion of the attendant physician or veterinarian.

The combinations may conveniently be presented for use in the form of a pharmaceutical formulation. In a further aspect of the present invention there is provided a pharmaceutical combination comprising a compound of Formula (I), or a pharmaceutically acceptable salt thereof, together with one or more additional therapeutic agents, and one or more pharmaceutically acceptable carriers, excipients or diluents. The individual components of such combinations may be administered either sequentially or simultaneously in separate or combined pharmaceutical formulations by any convenient route.

When administration is sequential, either the compound of the present invention or one or more additional therapeutic agent may be administered first. When administration is simultaneous, the combination may be administered either in the same or different pharmaceutical composition. When combined in the same formulation it will be appreciated that the compound and agents must be stable and compatible with each other and the other components of the formulation. When formulated separately they may be provided in any convenient formulation, conveniently in such manner as are known for such compounds in the art.

ABBREVIATIONS

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:

EtOAc ethyl acetate
Ac acetyl
AcOH acetic acid
$Ac_2O$ acetic anhydride
anh anhydrous
Boc N-tert-butoxycarbonyl
$(Boc)_2O$ di-tert-butyl dicarbonate
Boc anhydride di-tert-butyl dicarbonate
Celite® a filter aid composed of acid-washed diatomaceous silica, (a trademark of Manville Corp., Denver, Colo.)
DME dimethoxyethane
DCM dichloromethane
DIBAL-H diisobutyl aluminium hydride
DIPEA diisoproylethylamine
DMF dimethylformamide
DMSO-d6 deuterated dimethylsulfoxide
DMSO dimethylsulfoxide
ES MS Electrospray mass spectrometry
Et Ethyl
EtOH ethanol
h hours
HPLC high performance liquid chromatography
Int. Intermediate
LCMS Liquid chromatography mass spectroscopy
Mesylate methanesulfonate
Me methyl
MeOH methanol
OMs methanesulfonate MsCl mesyl chloride, methanesulfonyl chloride
min(s) minutes
NaBH(OAc)₃ sodium triacetoxyborohydride
NMR Nuclear Magnetic Resonance spectroscopy
Rt retention time
t-BuOMe methyl t-butyl ether
t-BuO tert-butyloxy
TFA trifluoroacetic acid
TEA triethylamine
THF tetrahydrofuran
uv ultraviolet

EXAMPLES

The following Examples illustrate the invention. These Examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance (¹H NMR) spectra were recorded, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Reactions involving metal hydrides including lithium hydride, lithium aluminium hydride, di-isobutylaluminum hydride, sodium hydride, sodium borohydride and sodium triacetoxyborohydride are carried out under argon or nitrogen unless otherwise specified.

Intermediates

Intermediate 1: N-1H-pyrazol-3-ylacetamide

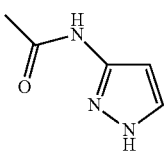

1H-pyrazol-3-amine (ALDRICH, 11.32 g, 0.136 mol) was dissolved in 100 mL of distilled water. NaHCO₃ (34 g, 0.408 mol) was slowly added. Acetic anhydride was then added dropwise and the resulting suspension was heated at reflux overnight. Then, the mixture was allowed to cool down to room temperature and the solid obtained was filtered off and characterized as the title compound (8.4 g, 0.067 mol, 49% yield). After concentration of the filtrate, a second precipitate was obtained (2.7 g, 0.021 mol, 16% yield), also characterized as the title compound. ¹H NMR (300 MHz, DMSO-d₆) δ ppm: 12.23 (br s, 1H), 10.30 (br s, 1H), 7.55 (br s, 1H), 6.45 (br s, 1H), 1.97 (s, 3H). [ES+MS] m/z 126 (MH⁺).

Intermediate 2: N-(5-methyl-1H-pyrazol-3-yl)acetamide

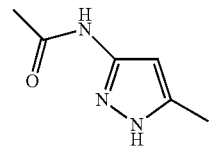

Title compound was prepared by a method analogous to that described for Intermediate 1, replacing 1H-pyrazol-3-amine with 5-methyl-1H-pyrazol-3-amine. (ALDRICH, 1.01 g, 7.25 mmol, 70.4% yield). ¹H NMR (300 MHz, DMSO-d₆) δ ppm: 11.89 (s, 1H), 10.16 (s, 1H), 6.22 (s, 1H), 2.16 (s, 3H), 1.94 (s, 3H). [ES+MS] m/z 140 (MH⁺).

Intermediate 3: ethyl 2-({[(1,1-dimethylethyl)oxy]carbonyl}amino)-1,3-thiazole-4-carboxylate

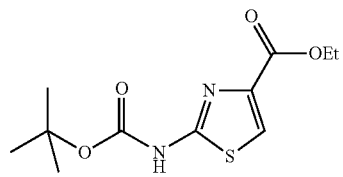 [SMILES: CCOC(=O)c1csc(NC(=O)OC(C)(C)C)n1]

Title compound was prepared following the procedure described in Synlett, 1999(8), pg. 1239-1240. ¹H NMR (300 MHz, CDCl₃) δ ppm: 8.20 (br s, 1H), 7.56 (s, 1H), 4.35 (q, 2H), 1.50 (m, 9H), 1.40 (t, 3H). [ES+MS] m/z 273 (MH⁺).

Intermediate 4: 1,1-dimethylethyl[4-(hydroxymethyl)-1,3-thiazol-2-yl]carbamate

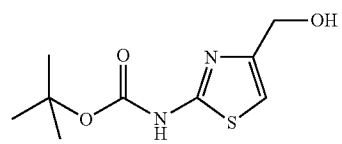

Sodium bis(methoxyethoxy) aluminium hydride (Red-Al) 65% solution in toluene (ALDRICH, 1.654 mL, 5.51 mmol) was added to a stirred solution of Intermediate 3 (ethyl 2-({[(1,1-dimethylethyl)oxy]carbonyl}amino)-1,3-thiazole-4-carboxylate (500 mg, 1.836 mmol) in dry THF (40 mL) under N₂ atmosphere at 0° C. Reaction mixture was stirred for 12 h at room temperature. THF was added to the mixture. Mixture was poured into water (20 mL) and was extracted with DCM, washed with NaCl saturated solution (15 mL) and dried over magnesium sulfate to afford the title compound (410 mg, 1.78 mmol, 97% yield). ¹H NMR (400 MHz, DMSO-d₆) δ ppm:

11.33 (br s, 1H), 6.84 (s, 1H), 5.17 (t, 1H), 4.40 (d, 2H), 1.48 (s, 9H). [ES+MS] m/z 231 (MH+).

Intermediate 5: 3,4-difluoro-2-pyridinecarbaldehyde

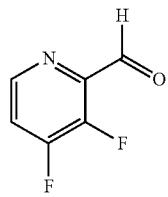

Butyllithium (ALDRICH, 1.529 mL, 3.82 mmol) was added dropwise over 10 min at −20° C. (CCl₄/acetone) to a solution of N,N,N',N'-tetramethylethylendiamine (ALDRICH, 0.521 mL, 3.48 mmol) in diethyl ether (anh) (15 mL). Reaction mixture was stirred at −20° C. for 1 h and cooled to −78° C. (acetone/CO₂(s)). A solution of 3,4-difluoropyridine (CHEMCOLLECT, 400 mg, 3.48 mmol) in diethyl ether (1 mL) was added dropwise over 15 min at −78° C. Mixture was stirred at −78° C. temperature for 1 hour. N,N-Dimethylformamide (300 µl), previously dissolved in diethyl ether (1 mL), was added dropwise over 10 min at −78° C. Reaction mixture was stirred for 2 hours and was poured carefully onto a rapidly stirring ice/water mixture. Mixture was stirred for 20 min and diluted with ethyl acetate (15 mL). Aqueous layer was further extracted with DCM (4×15 ml). Organic layers were combined, dried over MgSO₄(anh) and concentrated. Residue was purified by silica chromatography using Hexane-AcOEt (1:3) as eluents to yield the title compound (148 mg, 1.034 mmol, 30% yield). ¹H NMR (400 MHz, DMSO-d₆) δ ppm: 10.02-10.03 (m, 1H), 8.63-8.66 (m, 1H), 7.87-7.93 (m, 1H). [ES+MS] m/z 144 (MH+).

Intermediate 6: (3-fluoro-4-methyl-2-pyridinyl)methanol

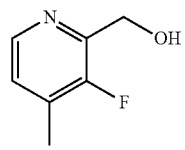

3-fluoro-4-methyl-2-pyridinecarbaldehyde (ASYMCHEM, 250 mg, 1.797 mmol) was dissolved under N₂ atmosphere, in dry MeOH (5 mL). NaBH₄ (ALDRICH, 187 mg, 4.94 mmol) was added. After 2 h reaction was completed. Solvent was evaporated. Residue was dissolved in ethyl acetate and partitioned between NaHCO₃ aqueous saturated solution. Organic layer was dried over MgSO₄ (anh), filtered and concentrated to obtain the title compound (200 mg, 1.42 mmol, 79%). ¹H NMR (300 MHz, DMSO-d₆) δ ppm: 8.21-8.22 (m, 1H), 7.27-7.31 (m, 1H), 5.23 (t, 1H), 4.56 (dd, 2H), 2.27-2.28 (m, 3H). [ES+MS] m/z 142 (MH+).

Intermediate 7: (3,4-difluoro-2-pyridinyl)methanol

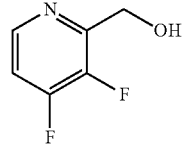

Intermediate 5 (142 mg, 0.992 mmol) was dissolved in ethanol (5 mL) under N₂(g) atmosphere. Sodium borohydride (ALDRICH, 113 mg, 2.98 mmol) was added and mixture of reaction was stirred for 1 hour. Crude of reaction was partitioned between DCM (15 mL) and distilled water (15 mL). Aqueous layer was extracted with DCM (2×15 mL). Organic layers were dried over MgSO₄(anh), filtered and concentrated to yield title compound (3,4-difluoro-2-pyridinyl)methanol (140 mg, 0.965 mmol, 97% yield). ¹H NMR (400 MHz, DMSO-d₆) δ ppm: 8.37-8.40 (m, 1H), 7.50-7.55 (m, 1H), 5.45 (t, 1H), 4.61-4.63 (m, 2H). [ES+MS] m/z 146 (MH+).

Intermediate 8: (3,5-difluoro-4-pyridinyl)methanol

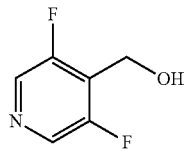

Title compound was prepared by a method analogous to that described for Intermediate 7, replacing 3,4-difluoro-2-pyridinecarbaldehyde with 3,5-difluoro-4-pyridinecarbaldehyde (FRONTIER) and using MeOH as solvent. (200 mg, 1.398 mmol, 73% yield). ¹H NMR (400 MHz, DMSO-d₆) δ ppm: 8.51 (s, 2H), 5.55 (t, 1H), 4.55-4.57 (m, 2H). [ES+MS] m/z 146 (MH+).

Intermediate 9: (3,5-difluoro-2-pyridinyl)methanol

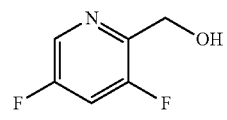

3,5-difluoro-2-pyridinecarboxylic acid (ALFAAESAR, 300 mg, 1.886 mmol) was dissolved in tetrahydrofuran (THF) (10 mL). N,N-diethylethanamine (FLUKA, 0.549 mL, 3.96 mmol) was added and mixture was cooled to −10° C. (ice in acetone). Isobutyl chloroformate (0.269 mL, 2.074 mmol, FLUKA) was added dropwise. Reaction was stirred 20 min at −10° C. Mixture was filtered into a previously prepared solution of sodium borohydride (ALDRICH, 214 mg, 5.66 mmol) in 2 mL of water at 0° C. and was stirred at 0° C. for 45 min. HCl (1N, aq) was added slowly until neutral pH. Aqueous mixture was partitioned with DCM (3×15 ml). Organic layer was dried over Na₂SO₄ (anh), filtered and concentrated. Residue was purified by silica gel chromatography using a linear gradient of DCM/MeOH to yield title compound (3,5-difluoro-2-pyridinyl)methanol (116 mg, 0.799 mmol, 42.4% yield). $^1$H NMR (400 MHz, DMSO-d$_6$) δ ppm: 8.44-8.45 (s, 1H), 7.88-7.93 (m, 1H), 5.35 (t, 1H), 4.56-4.58 (m, 2H). [ES+MS] m/z 146 (MH$^+$).

Intermediate 10: 2-(bromomethyl)-3-fluoro-4-methylpyridine

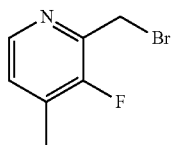

Intermediate 6 ((3-fluoro-4-methyl-2-pyridinyl)methanol, 246 mg, 1.743 mmol) was dissolved in 10 mL of anhydrous THF. Phosphorous tribromide (ALDRICH, 519 mg, 1.917 mmol) was added. Reaction mixture was stirred at room temperature overnight. Solvent was evaporated and residue was partitioned between Et$_2$O and NaHCO$_3$ (aqueous saturated solution). Organic layer was dried over MgSO$_4$ (anh), filtered and concentrated to give the title compound (372 mg, quantitative yield). $^1$H NMR (300 MHz, DMSO-d$_6$) ppm: 8.23-8.24 (m, 1H), 7.34-7.37 (m, 1H), 4.66 (s, 2H), 2.28 (s, 3H). [ES+MS] m/z 204 (M).

Intermediate 11: 2-(bromomethyl)-6-methylpyridine

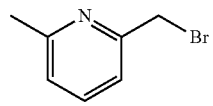

(6-methyl-2-pyridinyl)methanol (ALDRICH, 300 mg, 2.436 mmol) were dissolved in 10 mL of anhydrous THF. Phosphorous tribromide (ALDRICH, 0.252 mL, 2.68 mmol) was added. Reaction mixture was stirred at room temperature overnight. Solvent was evaporated and residue was purified by silica column chromatography using hexane:EtOAc as eluents to give a white solid. This solid was partitioned between EtOAc and distilled water (basified with NH$_3$ (32%, aqueous). Organic layer was dried with MgSO$_4$ (anh). Solvent was evaporated to obtain the title compound (152 mg, 0.817 mmol, 33.5% yield). $^1$H NMR (300 MHz, DMSO-d$_6$) δ ppm: 7.68 (t, 1H), 7.33 (d, 1H), 7.17 (d, 1H), 4.62 (s, 2H), 2.44 (s, 3H). [ES+MS] m/z 186 (M).

Intermediate 12: 1,1-dimethylethyl[4-(bromomethyl)-1,3-thiazol-2-yl]carbamate

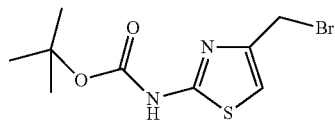

Intermediate 4 (1,1-dimethylethyl[4-(hydroxymethyl)-1,3-thiazol-2-yl]carbamate, 410 mg, 1.78 mmol) was dissolved in 5 mL of anhydrous DCM. Phosphorous tribromide (ALDRICH, 530 mg, 1.958 mmol) was added at 0° C. Reaction mixture was stirred at room temperature overnight. Reaction was diluted with 5 mL of water and extracted with DCM (3×5 mL). Organic layer was dried over MgSO$_4$ (anh), filtered and concentrated to give the title compound (300 mg, 1.02 mmol, 58% yield). $^1$H NMR (400 MHz, DMSO-d$_6$) δ ppm: 11.56 (br s, 1H), 7.23 (s, 1H), 4.60 (s, 2H), 1.48 (s, 9H).

Intermediate 13: 3-(bromomethyl)-2-fluoropyridine

To a solution of (2-fluoro-3-pyridinyl)methanol (ASYNCHEM, 505 mg, 3.97 mmol) in dry DCM (15 mL), under N$_2$ atmosphere, were added triphenylphospine (ALDRICH, 1042 mg, 3.97 mmol) and carbon tetrabromide (ALDRICH, 1318 mg, 3.97 mmol) in an ice-water bath. Reaction mixture was stirred at room temperature overnight. 0.3 eq. of carbon tetrabromide (ALDRICH, 409 mg, 1.19 mmol) and 0.3 eq. of triphenylphospine (ALDRICH, 323 mg, 1.19 mmol) were added. Reaction mixture was stirred until starting material was not detected. Solvent was evaporated to dryness. Residue was purified by silica gel chromatography using a linear gradient of hexane-EtOAc. Collected fractions afforded title compound (812 mg, 4.27 mmol, quantitative yield) as yellow oil. $^1$H NMR (300 MHz, DMSO-d$_6$) δ ppm: 8.20-8.21 (m, 1H), 8.06-8.12 (m, 1H), 735-7.39 (m, 1H), 4.69 (s, 2H). [ES+MS] m/z 190 (M).

The Intermediates 14-16 were prepared by methods analogous to that described for Intermediate 13 but replacing the alcohol ((2-fluoro-3-pyridinyl)methanol) with that indicated in Table 1.

TABLE 1

| Inter. | Structure | Alcohol | Physical data |
|---|---|---|---|
| 14 | 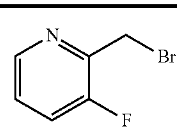 | | $^1$H NMR (300 MHz, DMSO-d$_6$) δ ppm: 8.40-8.43 (m, 1H), 7.75-7.81 (m, 1H), 7.47-7.52 (m, 1H), 4.71 (d, 2H). [ES+MS] m/z 190 (M). |

MAYBRIDGE

TABLE 1-continued

| Inter. | Structure | Alcohol | Physical data |
|---|---|---|---|
| 15 | ![structure] | ![structure] | $^1$H NMR (300 MHz, DMSO-$d_6$) δ ppm: 8.48 (s, 1H), 7.96 (s, 1H), 4.71 (s, 2H), 2.52 (s, 3H). |
|  |  | GALCHIMIA |  |
| 16 | ![structure] | ![structure] | $^1$H NMR (300 MHz, DMSO-$d_6$) δ ppm: 8.60 (s, 1H), 8.30 (s, 1H), 4.72 (s, 2H). |
|  |  | ACTIVATE |  |

Intermediate 17: 2-(1-bromoethyl)-3-fluoropyridine

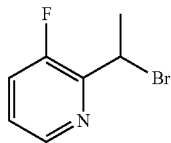

1-(3-fluoro-2-pyridinyl)ethanol (ASYNCHEM, 300 mg, 2.126 mmol) and triphenylphosphine (ALDRICH, 669 mg, 2.55 mmol) were dissolved in dry DCM (25 mL) under nitrogen atmosphere and solution was cooled at −10° C. N-Bromosuccinimide (ALDRICH, 416 mg, 2.338 mmol) was added in portions and reaction was stirred for 3 h. 0.3 eq. of triphenylphosphine (ALDRICH, 168 mg, 0.642 mmol) and 0.3 eq. of N-bromosuccinimide (ALDRICH, 114 mg, 0.642 mmol) were added and reaction was stirred at room temperature overnight. Reaction mixture was evaporated to dryness to afford 3.7 g of an oily solid. Residue was purified by silica column chromatography using a linear gradient of hexane/EtOAc (0%-50%-90%) affording the title compound (274 mg, 1.344 mmol, 63% yield). $^1$H NMR (300 MHz, DMSO-$d_6$) δ ppm: 8.43-8.44 (m, 1H), 7.71-7.77 (m, 1H), 7.46-7.50 (m, 1H), 5.64 (q, 1H), 2.00 (d, 3H).

Intermediate 18: (3,5-difluoro-2-pyridinyl)methyl methanesulfonate

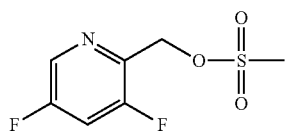

Intermediate 9 (3,5-difluoro-2-pyridinyl)methanol (114 mg, 0.786 mmol) was dissolved in DCM (anh) (6 mL) at 0° C. N,N-diethylethanamine (ALDRICH, 0.131 mL, 0.943 mmol) and methanesulfonyl chloride (ALDRICH, 0.067 mL, 0.864 mmol) were added. Reaction mixture was stirred at 0° C. for 1 h 30 min. Crude of reaction was partitioned between water and DCM, aqueous layer was extracted with DCM (2×10 mL). Organic layers were dried over MgSO4 (anh) and filtered. Solvent was eliminated to yield title compound (3,5-difluoro-2-pyridinyl)methyl methanesulfonate (137 mg, 0.614 mmol, 78% yield). $^1$H NMR (400 MHz, DMSO-$d_6$) δ ppm: $^1$H NMR (300 MHz, DMSO-$d_6$) δ ppm: 8.58 (d, 1H), 8.06-8.11 (m, 1H), 5.36 (d, 2H), 3.27 (s, 3H). [ES+MS] m/z 224 (MH$^+$).

Intermediates 19-21 were prepared by methods analogous to that described for Intermediate 18 but replacing the alcohol ((3,5-difluoro-2-pyridinyl)methanol) with that indicated in Table 2. Reaction times varied from 1 h to 4 h.

TABLE 2

| Inter. | Structure | Starting material | Physical Data |
|---|---|---|---|
| 19 | ![structure] See footnote (a) | ![structure] MAYBRIDGE | $^1$H NMR (400 MHz, DMSO-$d_6$) δ ppm: 8.48-8.50 (m, 1H), 7.82-7.87 (m, 1H), 7.57-7.61 (m, 1H), 5.37 (d, 2H), 3.27 (s, 3H). [ES+ MS] m/z 206 (MH$^+$). |
| 20 | 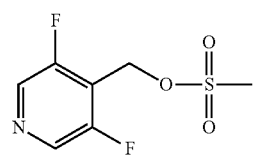 | Inter. 8 | $^1$H NMR (400 MHz, DMSO-$d_6$) δ ppm: 8.65 (s, 2H), 5.39 (s, 2H), 3.31 (s, 3H). [ES+ MS] m/z 224 (MH$^+$). |

TABLE 2-continued

| Inter. | Structure | Starting material | Physical Data |
|---|---|---|---|
| 21 | 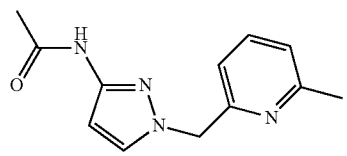 | Inter. 7 | $^1$H NMR (400 MHz, DMSO-$d_6$) δ ppm: 8.46-8.51 (m, 1H), 7.67-7.73 (m, 1H), 5.41 (d, 2H), 3.29 (s, 3H). [ES+ MS] m/z 224 (MH$^+$). |

(a) Organic layer was concentrated, dissolved in DCM and washed with NaHCO$_3$ (aq. sat).

Intermediate 22: N-{1-[(6-methyl-2-pyridinyl)methyl]-1H-pyrazol-3-yl}acetamide Intermediate 1 (97 mg, 0.774 mmol) was dissolved in 8 mL of THF (anh), at 0° C. NaH (ALDRICH, 31 mg, 0.774 mmol) was added, and mixture of reaction was stirred at 0° C. for 30 minutes. A solution of Intermediate 11 (144 mg, 0.774 mmol) in 2 mL THF (anh) was added to the mixture. Reaction was heated at 75° C. overnight. Mixture of reaction was partitioned between distilled water, EtOAc (×3) and DCM. Organic layers were dried over MgSO$_4$ (anh) and filtered. Solvent was evaporated under vacuum. Residue was purified by silica chromatography column using a linear gradient of DCM/MeOH as eluents to give the title compound (133 mg, 0.578 mmol, 75% yield). $^1$H NMR (300 MHz, DMSO-$d_6$) ppm: 10.40 (br s, 1H), 7.72 (d, 1H), 7.60-7.66 (m, 1H), 7.17-7.16 (m, 1H), 6.74-6.77 (m, 1H), 6.49 (d, 1H), 5.24 (s, 2H), 2.44 (s, 3H), 1.95 (s, 3H). [ES+MS] m/z 231 (MH$^+$).

The Intermediates 23-39 were prepared by methods analogous to that described for Intermediate 22 but replacing the benzyl halide (Intermediate 11) with that indicated in Table 3. Modifications are also indicated. Reaction times varied from 2 h to 3 h.

TABLE 3

| Inter. | Structure | Benzyl halide | Physical data |
|---|---|---|---|
| 23 | 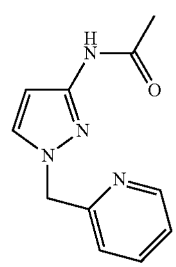 [SMILES: CC(=O)Nc1ccn(Cc2ccccn2)n1] | ALDRICH | $^1$H NMR (300 MHz, DMSO-$d_6$) δ ppm: 10.40 (br s, 1H), 8.50-8.53 (m, 1H), 7.73-7.79 (m, 2H), 7.28-7.32 (m, 1H), 6.99-7.01 (m, 1H), 6.49 (d, 1H), 5.30 (s, 2H), 1.95 (s, 3H). [ES+ MS] m/z 217 (MH+). |
| 24 | See footnote b) | ALDRICH | $^1$H NMR (300 MHz, DMSO-$d_6$) δ ppm: 10.39 (s, 1H), 8.48-8.50 (m, 2H), 7.75 (d, 1H), 7.58-7.62 (m, 1H), 7.34-7.38 (m, 1H), 6.47 (d, 1H), 5.25 (s, 2H), 1.95 (s, 3H). [ES+ MS] m/z 217 (MH+). |

TABLE 3-continued

| Inter. | Structure | Benzyl halide | Physical data |
|---|---|---|---|
| 25 | See footnote b) | Inter.14 or Inter. 19 | $^1$H NMR (300 MHz, DMSO-d$_6$) δ ppm: 10.37 (br s, 1H), 8.37-8.39 (m, 1H), 7.70-7.77 (m, 2H), 7.42-7.48 (m, 1H), 6.45 (d, 1H), 5.36 (d, 1H), 1.93 (s, 3H). [ES+ MS] m/z 235 (MH+). |
| 26 | See footnote b) and c) | Inter. 13 | $^1$H NMR (300 MHz, CDCl$_3$) δ ppm: 10.41 (s, 1H), 8.17 (m, 1H), 7.66-7.75 (m, 2H), 7.33-7.37 (m, 1H), 6.49 (d, 1H), 5.28 (s, 2H), 1.94 (s, 3H). [ES+ MS] m/z 235 (MH$^+$). |
| 27 | See footnote b) and c) | Inter. 10 | $^1$H NMR (300 MHz, CDCl$_3$) δ ppm: 10.35 (br s, 1H), 8.19-8.21 (m, 1H), 7.66 (d, 1H), 7.26-7.32 (m, 1H), 6.42 (d, 1H), 5.30-5.32 (d, 2H), 2.26 (s, 3H), 1.91 (s, 3H). [ES+ MS] m/z 249 (MH$^+$). |
| 28 | See footnote a) and b) | Inter. 15 | $^1$H NMR (300 MHz, DMSO-d$_6$) δ ppm: 10.39 (s, 1H), 8.33-8.34 (m, 1H), 7.74 (d, 1H), 7.70-7.71 (m, 1H), 6.47 (d, 1H), 5.23 (s, 2H), 2.51 (s, 3H), 1.95 (s, H). [ES+ MS] m/z 265 (MH$^+$). |

TABLE 3-continued

| Inter. | Structure | Benzyl halide | Physical data |
|---|---|---|---|
| 29 | (See footnote a) and b)) | Inter. 16 | $^1$H NMR (300 MHz, DMSO-d$_6$) δ ppm: 10.36 (s, 1H), 8.56 (d, 1H), 8.26 (d, 1H), 7.68 (d, 1H), 6.45 (d, 1H), 5.42 (s, 2H), 1.92 (s, 3H). [ES+ MS] m/z 285 (MH$^+$). |
| 30 | (See footnote b)) | Inter. 17 | $^1$H NMR (300 MHz, DMSO-d$_6$) δ ppm: 10.38 (s, 1H), 8.39-8.40 (m, 1H), 7.67-7.73 (m, 2H), 7.41-7.46 (m, 1H), 6.45 (d, 1H), 5.82 (q, 1H), 1.92 (s, 3H), 1.79 (d, 3H). [ES+ MS] m/z 249 MH$^+$. |
| 31 | (See footnote b)) | ALLICHEM | $^1$H NMR (300 MHz, DMSO-d$_6$) δ ppm: 10.41 (s, 1H), 7.92-8.00 (m, 1H), 7.74 (d, 1H), 6.96-7.11 (m, 2H), 6.51 (d, 1H), 5.27 (s, 2H), 1.96 (s, 3H). [ES+ MS] m/z 235 (MH$^+$). |
| 32 | (See footnote a), b) and d)) | ALDRICH | $^1$H NMR (300 MHz, CDCl3-d$_6$) δ ppm: 7.66 (br s, 1H), 7.19 (d, 1H), 6.66 (d, 1H), 4.90 (s, 2H), 2.39 (s, 3H), 2.14-2.17 (m, 6H). [ES+ MS] m/z 235 (MH$^+$). |

TABLE 3-continued

| Inter. | Structure | Benzyl halide | Physical data |
|---|---|---|---|
| 33 | See footnote a) and b) | ACROS | $^1$H NMR (300 MHz, DMSO-$d_6$) δ ppm: 10.41 (s, 1H), 7.70 (d, 1H), 6.47 (d, 1H), 6.02 (s, 1H), 5.24 (s, 2H), 2.35 (s, 3H), 1.96 (s, 3H). [ES+ MS] m/z 221 (MH$^+$). |
| 34 | See footnote a) | CHEMBRIDGE | $^1$H NMR (300 MHz, CDCl$_3$) δ ppm: 10.34 (s, 1H), 8.33 (m, 1H), 7.59-7.62 (m, 2H), 7.23-7.27 (m, 1H), 6.44 (d, 1H), 5.32 (s, 2H), 2.27 (s, 3H), 1.93 (s, 3H). [ES+ MS] m/z 231 (MH$^+$). |
| 35 | See footnote a) | Inter. 12 | $^1$H NMR (400 MHz, DMSO-$d_6$) δ ppm: 11.46 (br s, 1H), 10.39 (s, 1H), 7.60 (d, 1H), 6.90 (s, 1H), 6.45 (d, 1H), 5.12 (s, 2H), 1.96 (s, 3H), 1.47 (s, 9H) [ES+ MS] m/z 338 (MH$^+$). |
| 36 | See footnote a) | APOLLO | $^1$H NMR (400 MHz, DMSO-$d_6$) δ ppm: 10.37 (s, 1H), 8.44 (d, 1H), 8.31-8.33 (m, 1H), 7.98-8.00 (m, 1H), 7.76-7.81 (m, 3H), 7.65-7.69 (m, 1H), 6.45 (d, 1H), 5.82 (s, 2H), 1.90 (s, 3H). [ES+ MS] m/z 267 (MH$^+$). |

TABLE 3-continued

| Inter. | Structure | Benzyl halide | Physical data |
|---|---|---|---|
| 37 | See footnote b) | Inter. 18 | $^1$H NMR (400 MHz, DMSO-d$_6$) δ ppm: 10.37 (s, 1H), 8.47 (d, 1H), 7.95-8.00 (m, 1H), 7.70 (d, 1H), 6.45 (d, 1H), 5.35 (d, 2H), 1.93 (s, 3H). [ES+ MS] m/z 253 (MH$^+$). |
| 38 | 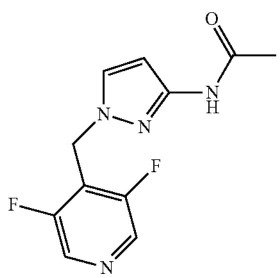 [SMILES: CC(=O)Nc1ccn(Cc2c(F)cncc2F)n1] | Inter. 20 | $^1$H NMR (400 MHz, DMSO-d$_6$) δ ppm: 10.40 (s, 1H), 8.56 (s, 2H), 7.76 (d, 1H), 6.46 (d, 1H), 5.37 (s, 2H), 1.92 (s, 3H). [ES+ MS] m/z 253 (MH$^+$). |
| 39 | See footnote a) | Inter. 21 | $^1$H NMR (400 MHz, DMSO-d$_6$) δ ppm: 10.38 (s, 1H), 8.38-8.41 (m, 1H), 7.73 (d, 1H), 7.55-7.60 (m, 1H), 6.46 (d, 1H), 5.41 (d, 2H), 1.93 (s, 3H). [ES+ MS] m/z 253 (MH$^+$). |
| 40 | See footnote a) and e) | Inter. 19 | $^1$H NMR (400 MHz, DMSO-d$_6$) δ ppm: 10.25 (br s, 1H), 8.35-8.38 (m, 1H), 7.70-7.75 (m, 1H), 7.41-7.45 (m, 1H), 6.29 (s, 1H), 5.29 (d, 2H), 2.32 (s, 3H), 1.91 (s, 3H). [ES+ MS] m/z 249 (MH$^+$). | a) DMF used as solvent.
b) Room temperature.
c) Purified without previous treatment.
d) Purified by silica column chromatography with linear gradient of Hexane/AcOEt.
e) Intermediate 2 was used instead of Intermediate 1.

Intermediate 41: N-{1-[(3-hydroxy-2-pyridinyl)methyl]-1H-pyrazol-3-yl}acetamide

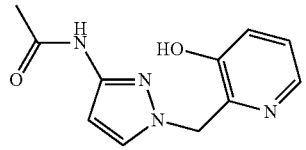 [SMILES: CC(=O)Nc1ccn(Cc2ncccc2O)n1]

Intermediate 1 (200 mg, 1.598 mmol) was dissolved in 2 mL of anhydrous DMF at 0° C. Sodium hydride (ALDRICH, 48.5 mg, 1.920 mmol) was added and mixture of reaction was stirred at 0° C. for 20 minutes. 2-(Bromomethyl)-3-pyridinol hydrobromide (ALFAAESAR, 301 mg, 1.598 mmol) was dissolved in 2 mL of DMF (anh) at 0° C. Sodium hydride (ALDRICH, 48.5 mg, 1.920 mmol) was added and this solution was stirred at 0° C. for 20 minutes. Solution of 2-(bromomethyl)-3-pyridinol was added dropwise to reaction mixture. Reaction was stirred at 80° C. for 24 h. Solvent was evaporated to dryness. Residue was partitioned between EtOAc and NH$_4$Cl. Organic layer was dried over MgSO$_4$ (anh), filtered and concentrated to dryness. Residue was purified using silica chromatography column using a linear gradient of DCM/MeOH as eluents to give the title compound (48.5 mg, 0.207 mmol, 13% yield). $^1$H NMR (300 MHz, CDCl$_3$) δ ppm: 9.70 (br s, 1H), 8.04 (m, 1H), 7.46 (d, 1H), 7.33 (m, 1H), 7.24 (m, 1H), 6.53 (d, 1H), 5.42 (s, 2H), 2.27 (s, 3H). [ES+MS] m/z 233 (MH$^+$).

Intermediate 42: N-[1-(2-quinolinylmethyl)-1H-pyrazol-3-yl]acetamide

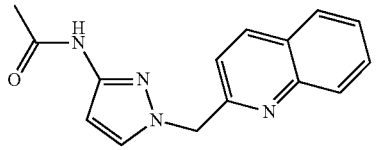 [SMILES: CC(=O)Nc1ccn(Cc2ccc3ccccc3n2)n1]

Title compound was prepared by a method analogous to that described for Intermediate 41 using Intermediate 1 (150 mg, 1.199 mmol), replacing 2-(Bromomethyl)-3-pyridinol hydrobromide with 2-(chloromethyl)quinoline hydrochloride (ALDRICH). Title compound was obtained (90 mg, 0.338 mmol, 28.2% yield). $^1$H NMR (300 MHz, CDCl$_3$) δ ppm: 8.10 (d, 1H), 8.07 (d, 1H), 7.79 (d, 1H), 7.74 (m, 1H), 7.55 (m, 1H), 7.46 (d, 1H), 7.07 (d, 1H), 6.76 (d, 1H), 5.49 (s, 2H), br s 2.14 (s, 3H). [ES+MS] m/z 267 (MH$^+$).

Intermediate 43: N-{1-[(2-methyl-1,3-thiazol-4-yl)methyl]-1H-pyrazol-3-yl}acetamide

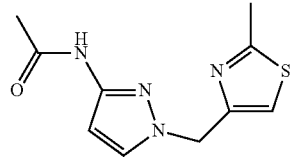 [SMILES: CC(=O)Nc1ccn(Cc2csc(C)n2)n1]

Title compound was prepared by a method analogous to that described for Intermediate 41, replacing the benzyl halide by 4-(chloromethyl)-2-methyl-1,3-thiazole hydrochloride (MAYBRIDGE). 4-(chloromethyl)-2-methyl-1,3-thiazole hydrochloride (MAYBRIDGE) was also liberated using NaOH (1N, aq) at room temperature. $^1$H NMR (300 MHz, DMSO-d$_6$) ppm: 10.37 (s, 1H), 7.62-7.63 (m, 1H), 7.25 (s, 1H), 6.43-6.44 (m, 1H), 5.20 (s, 2H), 2.59 (s, 3H), 1.93 (s, 3H). [ES+MS] m/z 237 (MH$^+$).

Intermediate 44: 2-(1H-pyrazol-3-yl)-1H-isoindole-1,3(2H)-dione

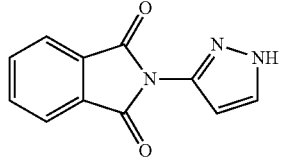 [SMILES: O=C1c2ccccc2C(=O)N1c1cc[nH]n1]

In a 500 mL round-bottom flask a mixture of 3-aminopyrazole (ALDRICH, 10 g, 120 mmol) and phthalic anhydride (ALDRICH, 24.96 g, 168 mmol) in 1,4-dioxane (150 mL) was stirred at reflux for 17 h. Solvent was evaporated to dryness. Residue was triturated with EtOH to afford (23.6 g, 111 mmol, yield 92%) of the title compound. $^1$H NMR (300 MHz, DMSO-d$_6$) δ ppm: 13.09 (br s, 1H), 7.89-7.98 (m, 4H), 7.86 (br s, 1H), 6.36 (d, 1H). [ES+MS] m/z 214 (MH$^+$).

Intermediate 45: 2-{1-[(6-fluoro-2-pyridinyl)methyl]-1H-pyrazol-3-yl}-1H-isoindole-1,3(2H)-dione

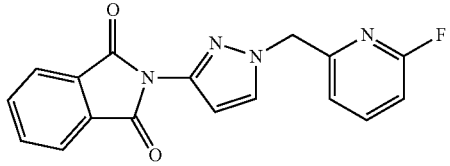 [SMILES: O=C1c2ccccc2C(=O)N1c1ccn(Cc2cccc(F)n2)n1]

A mixture of Intermediate 44 (200 mg, 0.938 mmol), 2-(chloromethyl)-6-fluoropyridine (ALLICHEM, 137 mg, 0.938 mmol) and potassium carbonate (ALDRICH, 157 mg, 0.938 mmol) dissolved in acetonitrile (10 mL) was stirred at 80° C. for 6 h. 0.2 eq. of 2-(chloromethyl)-6-fluoropyridine (ALLICHEM, 27.3 mg, 0.188 mmol) and 5 mL of dry acetonitrile were added. Reaction was stirred at 80° C. overnight. Reaction was diluted with DCM and filtered. Solvent was evaporated to dryness. Residue was purified by silica column chromatography using a linear gradient of hexane/EtOAc to yield the title compound (94 mg, 0.292 mmol, 31% yield). $^1$H NMR (300 MHz, DMSO-d$_6$) δ ppm: 8.02-7.88 (m, 6H), 7.11 (m, 2H), 6.43 (d, 1H), 5.45 (s, 2H). [ES+MS] m/z 323 (MH$^+$).

Intermediate 46: 2-{1-[(2-fluoro-3-pyridinyl)methyl]-1H-pyrazol-3-yl}-1H-isoindole-1,3(2H)-dione

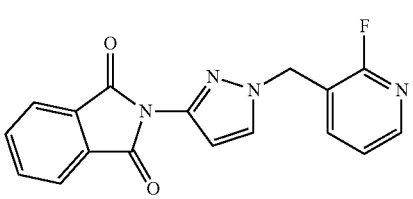 [SMILES: O=C1c2ccccc2C(=O)N1c1ccn(Cc2cccnc2F)n1]

Title compound was prepared by a method analogous to that described for Intermediate 45, replacing 2-(chloromethyl)-6-fluoropyridine with Intermediate 13 (200 mg, 1.051 mmol) to yield the title compound (211 mg, 0.655 mmol, 62.3% yield). $^1$H NMR (300 MHz, DMSO-d$_6$) δ ppm: 8.21

(m, 1H), 8.00 (d, 1H), 7.95-7.88 (m, 4H), 7.78 (m, 1H), 7.38 (m, 1H), 6.41 (d, 1H), 5.46 (s, 2H). [ES+MS] m/z 323 (MH+).

Intermediate 47: 1-[(2-fluoro-3-pyridinyl)methyl]-1H-pyrazol-3-amine

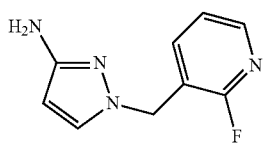 [SMILES: Nc1ccn(Cc2cccnc2F)n1]

A mixture of Intermediate 46 (180 mg, 0.558 mmol) and hydrazine monohydrate (FLUKA, 0.035 mL, 1.117 mmol) in ethanol (10 mL) was stirred at room temperature for 4 h. Precipitate was filtered and washed with DCM. Filtrate was evaporated to dryness. Residue was purified by silica column chromatography using a linear gradient of DCM/MeOH as eluents to yield the title compound (102 mg, 0.53 mmol, 95% yield). $^1$H NMR (300 MHz, DMSO-d$_6$) δ ppm: 8.15 (m, 1H), 7.57-7.62 (m, 1H), 7.45 (d, 1H), 7.29-7.33 (m, 1H), 5.41 (d, 1H), 5.08 (s, 2H), 4.62 (br s, 2H). [ES+MS] m/z 193 (MH+).

Intermediate 48: 1-[(6-fluoro-2-pyridinyl)methyl]-1H-pyrazol-3-amine

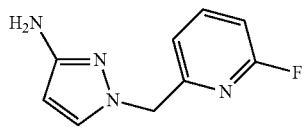

Title compound was prepared by a method analogous to that described for Intermediate 47, replacing Intermediate 46 with Intermediate 45 (90 mg, 0.279 mmol) to yield the title compound (48 mg, 0.250 mmol, 48% yield). $^1$H NMR (300 MHz, CDCl$_3$) δ ppm: 7.73 (q, 1H), 7.30 (d, 1H), 6.89 (dd, 1H), 6.83 (dd, 1H), 5.67 (d, 1H), 5.16 (s, 2H), 2.87 (br s, 2H). [ES+MS] m/z 192 (MH+).

Intermediate 49: 1-[(3,5-difluoro-2-pyridinyl)methyl]-1H-pyrazol-3-amine

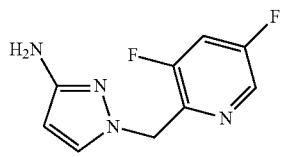 [SMILES: Nc1ccn(Cc2ncc(F)cc2F)n1]

Intermediate 37 (94 mg, 0.373 mmol) was dissolved in dioxane (2 mL) and HCl (aqueous, 2 M) (0.932 mL) was added. The mixture was heated to 60° C. for 7 h 30 min. Reaction mixture was basified with Na$_2$CO$_3$ (aq,sat) and extracted with ethyl acetate (3×15 mL). Organic layers were dried over Na$_2$SO$_4$ (anh), filtered and concentrated to dryness to give the title compound (68 mg, 0.324 mmol, 87% yield). $^1$H NMR (400 MHz, DMSO-d$_6$) ppm: 8.46 (d, 1H), 7.92-7.97 (m, 1H), 7.41 (d, 1H), 5.38 (d, 1H), 5.16 (d, 2H), 4.55 (br s, 2H). [ES+MS] m/z 211 (MH+).

Intermediates 50-52 were prepared by methods analogous to that described for Intermediate 49 but replacing the acetyl intermediate (Intermediate 37) with the Intermediate indicated in Table 4. Modifications are also indicated. Reaction times varied from 5 h 30 min to 9 h 30 min.

TABLE 4

| Intermediate | Structure | Acetyl Intermediate | Physical data |
| --- | --- | --- | --- |
| 50 | 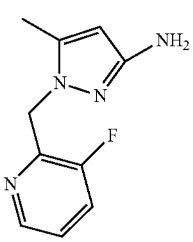 | 40 | $^1$H NMR (400 MHz, DMSO-d$_6$) δ ppm: 8.34-8.36 (m, 1H), 7.67-7.72 (m, 1H), 7.39-7.43 (m, 1H), 5.22 (s, 1H), 5.11 (d, 2H), 4.39 (br s, 2H). [ES+ MS] m/z 207 (MH+). |
| 51 | 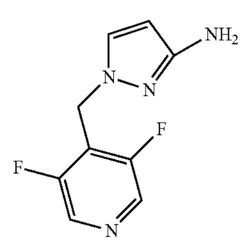 [SMILES: Nc1ccn(Cc2c(F)cncc2F)n1] | 38 | $^1$H NMR (400 MHz, DMSO-d$_6$) δ ppm: 8.53 (s, 2H), 7.46 (d, 1H), 5.38 (d, 1H), 5.17 (s, 2H), 4.63 (br s, 2H). [ES+ MS] m/z 211 (MH+). |

TABLE 4-continued

| Intermediate | Structure | Acetyl Intermediate | Physical data |
|---|---|---|---|
| 52 | See footnote (a) | 39 | $^1$H NMR (400 MHz, DMSO-$d_6$) δ ppm: 7.34 (d, 1H), 7.15 (d, 1H), 5.95-5.99 (m, 1H), 5.31 (d, 1H), 4.78 (d, 2H), 4.42 (br s, 2H). [ES+ MS] m/z 209 (MH$^+$). |

(a) Aqueous layer was concentrated and residue was washed with DCM:MeOH (10:1) and filtered.

Intermediate 53: 1-[(3-fluoro-4-methyl-2-pyridinyl)methyl]-1H-pyrazol-3-amine

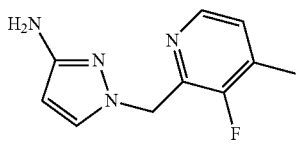

Intermediate 27 (256 mg, 1.031 mmol) was dissolved in EtOH (15 mL) and NaOH (aqueous, 25%) (15 mL) was added. The mixture was heated to 75° C. for 7 h 30 min. Ethanol was evaporated under vacuum. Aqueous layer was extracted with EtOAc (×2), organic layers were dried over MgSO$_4$ (anh) and concentrated to dryness to give the title compound (220 mg, quantitative yield). $^1$H NMR (300 MHz, DMSO-$d_6$) δ ppm: 8.19-8.21 (m, 1H), 7.39 (d, 1H), 7.29-7.32 (m, 1H), 5.37 (d, 1H), 5.13 (d, 2H), 4.53 (br s, 2H), 2.27 (m, 3H). [ES+MS] m/z 207 (MH$^+$).

Intermediates 54-71 were prepared by methods analogous to that described for Intermediate 53 but replacing the acetyl intermediate (Intermediate 27) with the Intermediate indicated in Table 5. Modifications are also indicated. Reaction times varied from 1 h 30 min to 19 h.

TABLE 5

| Inter | Structure | Acetyl Intermediate | Physical data |
|---|---|---|---|
| 54 | See footnote (a) | 22 | $^1$H NMR (300 MHz, DMSO-$d_6$) δ ppm: 7.60 (t, 1H), 7.44 (d, 1H), 7.11 (d, 1H), 6.68 (d, 1H), 5.43 (d, 1H), 5.05 (s, 2H), 4.58 (br s, 2H), 2.43 (s, 3H). [ES MS] m/z 189 (MH$^+$). |
| 55 | 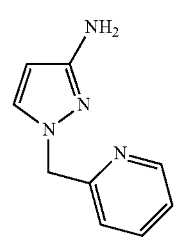 [SMILES: Nc1ccn(Cc2ccccn2)n1] | 23 | $^1$H NMR (300 MHz, DMSO-$d_6$) δ ppm: 8.48 (m, 1H), 7.71 (m, 1H), 7.46 (d, 1H), 7.25 (m, 1H), 6.91 (d, 1H), 5.42 (d, 1H), 5.10 (s, 2H), 4.57 (br s 2H). [ES+ MS] m/z 175 (MH$^+$). |
| 56 | 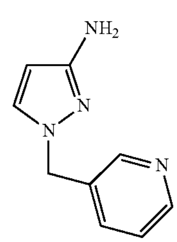 [SMILES: Nc1ccn(Cc2cccnc2)n1] | 24 | $^1$H NMR (300 MHz, DMSO-$d_6$) δ ppm: 8.44 (m, 1H), 8.41 (s, 1H), 7.55 (m, 1H), 7.46 (d, 1H), 7.33 (m, 1H), 5.40 (d, 1H), 5.05 (s, 2H), 4.61 (br s, 2H). [ES+ MS] m/z 175 (MH$^+$). |

TABLE 5-continued

| Inter | Structure | Acetyl Intermediate | Physical data |
|---|---|---|---|
| 57 | (3-amino-1H-pyrazol-1-yl)methyl attached to 3-fluoropyridin-2-yl<br>See footnote (b) | 25 | $^1$H NMR (300 MHz, DMSO-d$_6$) δ ppm: 8.35 (d, 1H), 7.70 (t, 1H), 7.40 (m, 2H), 5.37 (d, 1H), 5.16 (s, 2H), 4.52 (br s, 2H). [ES+ MS] m/z 193 (MH$^+$). |
| 58 | (3-amino-1H-pyrazol-1-yl)methyl attached to 2-ethoxypyridin-3-yl | 26 | $^1$H NMR (300 MHz, DMSO-d$_6$) δ ppm: 8.03 (m, 1H), 7.38 (d, 1H), 7.14 (m, 1H), 6.90 (m, 1H), 5.41 (d, 1H), 4.95 (s, 2H), 4.57 (br s, 2H), 4.32 (q, 2H), 1.31 (t, 3H). [ES+ MS] m/z 219 (MH$^+$). |
| 59 | (3-amino-1H-pyrazol-1-yl)methyl attached to 5-chloro-6-methylpyridin-3-yl | 28 | $^1$H NMR (300 MHz, DMSO-d$_6$) δ ppm: 8.26 (d, 1H), 7.61 (d, 1H), 7.46 (d, 1H), 5.39 (d, 1H), 5.03 (s, 2H), 4.61 (br s, 2H), 2.48 (s, 3H). [ES+ MS] m/z 223 (MH$^+$). |
| 60 | (3-amino-1H-pyrazol-1-yl)methyl attached to 3,5-dichloropyridin-2-yl<br>See footnote (c) | 29 | $^1$H NMR (300 MHz, DMSO-d$_6$) δ ppm: 8.55 (d, 1H), 8.22 (d, 1H), 7.40 (d, 1H), 5.38 (d, 1H), 5.23 (s, 2H), 4.54 (br s, 2H). [ES+ MS] m/z 243 (MH$^+$). |
| 61 | 1-(3-fluoropyridin-2-yl)ethyl attached to 3-amino-1H-pyrazol-1-yl | 30 | $^1$H NMR (300 MHz, DMSO-d$_6$) δ ppm: 8.37 (m, 1H), 7.67 (m, 1H), 7.43 (m, 2H), 5.61 (q, 1H), 5.37 (d, 1H), 4.51 (br s, 2H), 1.70 (d, 3H). [ES MS] m/z 207 (MH$^+$). |

TABLE 5-continued

| Inter | Structure | Acetyl Intermediate | Physical data |
|---|---|---|---|
| 62 | 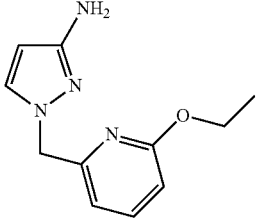 [SMILES: CCOc1cccc(Cn2ccc(N)n2)n1] | 31 | ¹H NMR (300 MHz, DMSO-d$_6$) δ ppm: 7.60 (t, 1H), 7.44 (d, 1H), 6.63 (d, 1H), 6.46 (d, 1H), 5.43 (d, 1H), 5.00 (s, 2H), 4.57 (br s, 2H), 4.25 (q, 2H), 1.28 (t, 3H). [ES+ MS] m/z 219 (MH$^+$). |
| 63 | 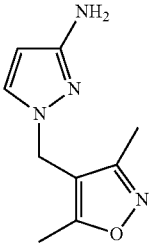 | 32 | ¹H NMR (300 MHz, DMSO-d$_6$) δ ppm: 7.35 (d, 1H), 5.35 (d, 1H), 4.82 (s, 2H), 4.54 (br s, 2H), 2.34 (s, 3H), 2.10 (s, 3H). [ES+ MS] m/z 193 (MH$^+$). |
| 64 | 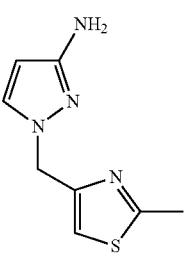 | 43 | ¹H NMR (300 MHz, DMSO-d$_6$) δ ppm: 7.35 (d, 1H), 7.15 (s, 1H), 5.38 (d, 1H), 5.02 (s, 2H), 4.53 (br s, 2H), 2.59 (s, 3H). [ES MS] m/z 195 (MH$^+$). |
| 65 | 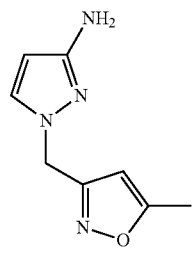 | 33 | ¹H NMR (300 MHz, DMSO-d$_6$) δ ppm: 7.41 (d, 1H), 5.98 (s, 1H), 5.40 (d, 1H), 5.03 (s, 2H), 4.60 (br s, 2H), 2.34 (s, 3H). [ES+ MS] m/z 179 (MH$^+$). |
| 66 | 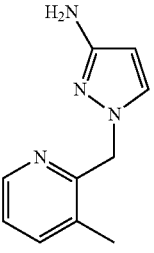 See footnote (d) | 34 | ¹H NMR (300 MHz, CDCl$_3$) δ ppm: 8.31 (m, 1H), 7.55 (m, 1H), 7.30 (d, 1H), 7.21 (m, 1H), 5.36 (d, 1H), 5.11 (s, 2H), 4.49 (br s, 2H), 2.27 (s, 3H). [ES+ MS] m/z: 189 (MH$^+$). |
| 67 | 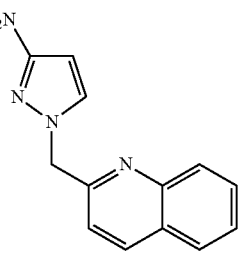 | 42 | ¹H NMR (400 MHz, CDCl$_3$) δ ppm: 8.09 (m, 2H), 7.81-7.70 (m, 2H), 7.53 (m, 1H), 7.31 (d, 1H), 7.14 (d, 1H), 5.68 (s, 1H), 5.42 (s, 2H). [ES+ MS] m/z 210 (MH$^+$). |

TABLE 5-continued

| Inter | Structure | Acetyl Intermediate | Physical data |
|---|---|---|---|
| 68 | 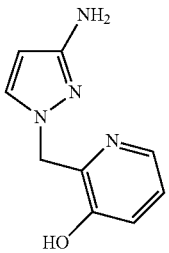 See footnote (e) | 41 | $^1$H NMR (300 MHz, DMSO-$d_6$) δ ppm: 10.28 (br s, 1H), 7.95 (m, 1H), 7.18 (m, 2H), 7.00 (d, 1H), 5.27-5.32 (m, 3H), 5.12 (s, 2H). [ES+ MS] m/z 191 (MH$^+$). |
| 69 | 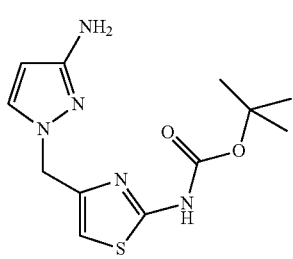 See footnote (e) | 35 | $^1$H NMR (400 MHz, DMSO-$d_6$) δ ppm: 11.48 (br s, 1H), 7.32 (d, 1H), 6.79 (s, 1H), 5.39 (d, 1H), 4.94 (s, 2H), 4.52 (br s, 2H), 1.47 (s, 9H). [ES+ MS] m/z 296 (MH$^+$) |
| 70 | 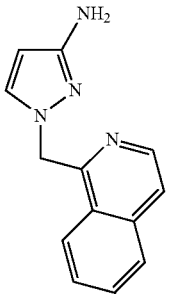 [SMILES: Nc1ccn(Cc2nccc3ccccc23)n1] | 36 | $^1$H NMR (400 MHz, DMSO-$d_6$) δ ppm: 8.43 (d, 1H), 8.33-8.35 (m, 1H), 7.97-7.99 (m, 1H), 7.74-7.79 (m, 2H), 7.64-7.68 (m 1H), 7.44 (d, 1H), 5.62 (s, 2H), 5.38 (d, 1H), 4.50 (br s, 2H). [ES+ MS] m/z 267 (MH$^+$). |
| 71 | 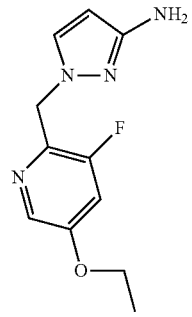 [SMILES: CCOc1cnc(Cn2ccc(N)n2)c(F)c1] | 37 | $^1$H NMR (300 MHz, DMSO-$d_6$) δ ppm: 8.06-8.10 (m, 1H), 7.39-7.49 (m, 1H), 7.30-7.36 (m, 1H), 5.36 (d, 1H), 5.06-5.07 (m, 2H), 4.44-4.52 (m, 2H), 4.05-4.14 (m, 2H), 1.30-1.37 (m, 3H). |

(a) NaOH (2N).

(b) Crude was purified using silica gel cartridge with a linear gradient of DCM/MeOH.

(c) Crude was purified twice using silica gel cartridge with a linear gradient of DCM/MeOH and purified again by preparative HPLC, using XTERRA chromatography column (19 mm × 150 mm), gradient 10%-100% ACN/NH$_4$HCO$_3$ (aq. 10 mM).

(d) Aqueous layer was saturated with NaCl and extracted with ethyl acetate.

(e) Aqueous layer was extracted with DCM and it was brought to pH = 7 with HCl 1N.

Intermediate 72: 2-fluoro-6-[(3-isothiocyanato-1H-pyrazol-1-yl)methyl]pyridine

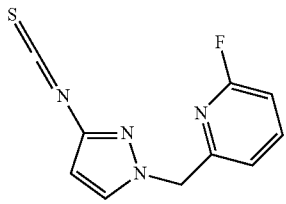 [SMILES: Fc1cccc(Cn2ccc(N=CC=S)n2)n1]

Intermediate 48 (48 mg, 0.250 mmol) was dissolved in 2 mL of DCM. 2 mL of sodium bicarbonate solution (aqueous, saturated) were added to the mixture and finally thiocarbonyl dichloride (ALDRICH, 0.019 mL, 0.250 mmol) was added dropwise. The reaction was stirred for 15 h. The crude was dissolved in 5 mL of DCM and washed with 5 mL of distilled water. Organic layer was dried over $MgSO_4$ (anh), filtered and concentrated to dryness to give the title compound as a brown oil (45 mg, 0.192 mmol, 77%). $^1$H NMR (300 MHz, $CDCl_3$) δ ppm: 7.78 (q, 1H), 7.49 (d, 1H), 6.98 (dd, 1H), 6.89 (dd, 1H), 6.22 (d, 1H); 5.26 (s, 2H). [ES+MS] m/z 235 (MH$^+$).

Intermediates 73-100 were prepared by methods analogous to that described for Intermediate 72 but replacing Intermediate 48 with that indicated in Table 6. Reaction time: from 20 minutes to 6 h. Other modifications are also indicated.

TABLE 6

| Int | Structure | Starting intermediate | Physical data |
|---|---|---|---|
| 73 | 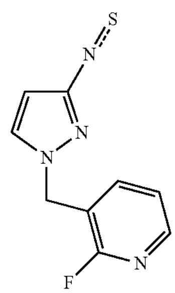 | 47 | $^1$H NMR (300 MHz, DMSO-$d_6$) δ ppm: 8.21 (m, 1H), 7.97 (d, 1H), 7.78 (m, 1H), 7.37 (m, 1H), 6.47 (d, 1H), 5.38 (s, 2H). [ES+ MS] m/z 235 (MH$^+$). |
| 74 | 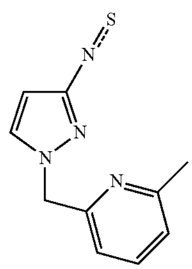 | 54 | $^1$H NMR (300 MHz, DMSO-$d_6$) δ ppm: 7.95 (d, 1H), 7.67 (t, 1H), 7.19 (d, 1H), 6.88 (d, 1H), 6.46 (d, 1H), 5.33 (s, 2H), 2.44 (s, 3H). [ES+ MS] m/z 231 (MH$^+$). |
| 75 | 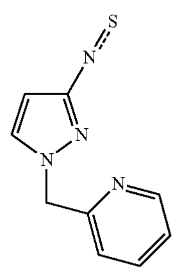 | 55 | $^1$H NMR (300 MHz, DMSO-$d_6$) δ ppm: 8.52 (m, 1H), 7.95 (d, 1H), 7.79 (m, 1H), 7.32 (m, 1H), 7.14 (d, 1H), 6.46 (d, 1H), 5.39 (s, 2H). [ES+ MS] m/z 217 (MH$^+$). |
| 76 | 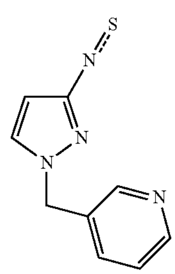 | 56 | $^1$H NMR (300 MHz, DMSO-$d_6$) δ ppm: 8.51 (m, 2H), 7.97 (d, 1H), 7.65 (m, 1H), 7.37 (m, 1H), 6.45 (d, 1H), 5.34 (s, 2H). [ES+ MS] m/z 217(MH$^+$). |

See footnote (a)

TABLE 6-continued

| Int | Structure | Starting intermediate | Physical data |
|---|---|---|---|
| 77 | 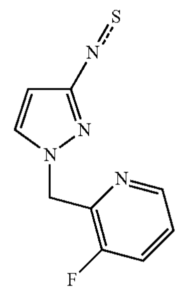 | 57 | $^1$H NMR (300 MHz, DMSO-d$_6$) δ, ppm: 8.38 (m, 1H), 7.93 (d, 1H), 7.76 (m, 1H), 7.48 (m, 1H), 6.44 (d, 1H), 5.47 (s, 2H). [ES+ MS] m/z 235 (MH$^+$). |
| 78 | 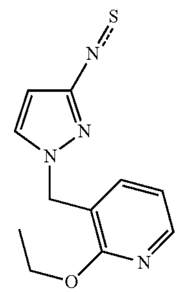 | 58 | $^1$H NMR (300 MHz, DMSO-d$_6$) δ ppm: 7.94 (m, 1H), 7.65 (m, 1H), 6.67 (m, 2H), 6.46 (m, 1H), 5.27 (s, 2H), 4.22 (q, 2H), 1.24 (t, 3H). [ES+ MS] m/z 261 (MH$^+$). |
| 79 | 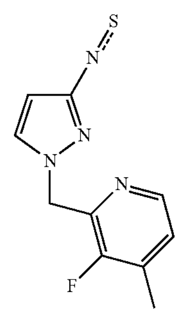 | 53 | $^1$H NMR (300 MHz, DMSO-d$_6$) δ ppm: 8.21 (d, 1H), 7.91 (d, 1H), 7.34 (t, 1H), 6.42 (d, 1H), 5.43 (s, 2H), 2.28 (s, 3H). [ES+ MS] m/z 249 (MH$^+$). |
| 80 | 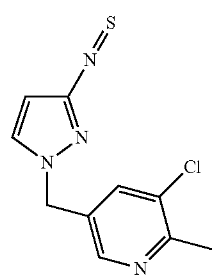 | 59 | $^1$H NMR (300 MHz, DMSO-d$_6$) δ ppm: 8.37 (d, 1H), 7.97 (d, 1H), 7.80 (d, 1H), 6.45 (d, 1H), 5.31 (s, 2H), 2.52 (s, 3H). [ES+ MS] m/z 265 (MH$^+$). |
| 81 | 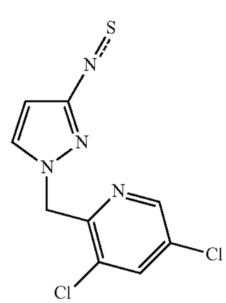 | 60 | $^1$H NMR (300 MHz, DMSO-d$_6$) δ ppm: 8.55 (d, 1H), 8.29 (d, 1H), 7.91 (d, 1H), 6.45 (d, 1H), 5.22 (s, 2H). [ES+ MS] m/z 285 (MH$^+$). |

TABLE 6-continued

| Int | Structure | Starting intermediate | Physical data |
|---|---|---|---|
| 82 | 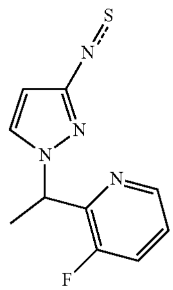 | 61 | $^1$H NMR (300 MHz, DMSO-d$_6$) δ ppm: 8.40 (m, 1H), 7.97 (d, 1H), 7.74 (m, 1H), 7.48 (m, 1H), 6.43 (d, 1H), 5.92 (m, 1H), 1.79 (d, 3H). [ES+ MS] m/z 249 (MH$^+$). |
| 83 | 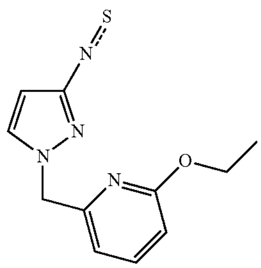 | 62 | $^1$H NMR (300 MHz, DMSO-d$_6$) δ ppm: 7.93-7.95 (m, 1H), 7.62-7.69 (m, 1H), 6.65-6.70 (m, 2H), 6.45-6.47 (m, 1H), 5.28 (s, 2H), 4.18-4.25 (m, 2H), 1.22-1.27 (m, 3H). [ES+ MS] m/z 261 (MH$^+$). |
| 84 | 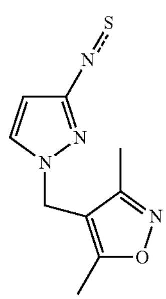 | 63 | $^1$H NMR (300 MHz, DMSO-d$_6$) δ ppm: 7.88 (d, 1H), 6.42 (s, 1H), 5.11 (s, 2H), 2.39 (s, 3H), 2.12 (s, 3H). [ES+ MS] m/z 235 (MH$^+$). |
| 85 | 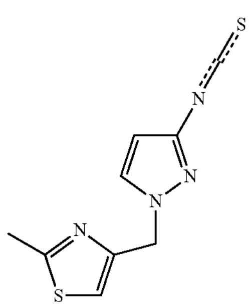 | 64 | $^1$H NMR (300 MHz, DMSO-d$_6$) δ ppm: 7.87 (d, 1H), 7.37 (s, 1H), 6.42 (d, 1H), 5.30 (s, 2H), 2.60 (s, 3H). [ES+ MS] m/z 237 (MH$^+$). |
| 86 | 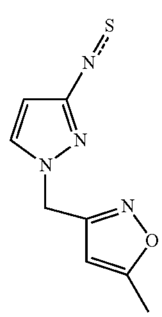 | 65 | $^1$H NMR (300 MHz, DMSO-d$_6$) δ ppm: 7.93 (d, 1H), 6.45 (d, 1H), 6.12 (s, 1H), 5.35 (d, 2H), 2.36 (s, 3H). [ES+ MS] m/z 221 (MH$^+$). |

TABLE 6-continued

| Int | Structure | Starting intermediate | Physical data |
|---|---|---|---|
| 87 | 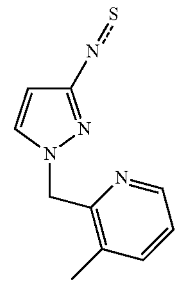 | 66 | $^1$H NMR (300 MHz, DMSO-d$_6$) δ ppm: 8.45 (dd, 1H), 7.91 (d, 1H), 7.84 (d, 1H), 7.45 (m, 1JH), 6.45 (d, 1H), 5.49 (s, 2H), 2.34 (s, 3H). [ES+ MS] m/z 231 (MH$^+$). |
| 88 | 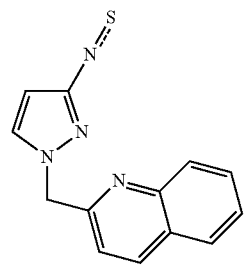 | 67 | $^1$H NMR (400 MHz, CDCl$_3$) δ ppm: 8.17 (m, 1H), 8.08 (m, 1H), 7.84-7.73 (m, 3H), 7.58 (m, 1H), 7.51 (d, 1H), 6.24 (d, 1H), 5.54 (s, 2H). [ES+ MS] m/z 267 (MH$^+$). |
| 89 | 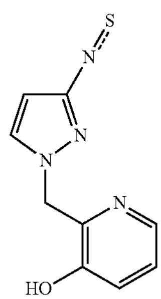 | 68 | [ES+ MS] m/z 233 (MH$^+$). |
| 90 | 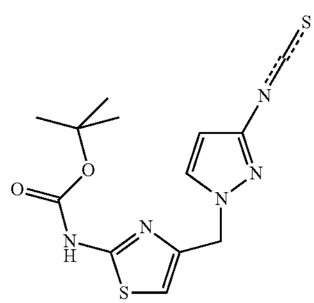 | 69 | $^1$H NMR (400 MHz, DMSO-d$_6$) δ ppm: 11.50 (br s, 1H), 7.83 (d, 1H), 7.01 (s, 1H), 6.43 (d, 1H), 5.22 (s, 2H), 1.44 (s, 9H). [ES+ MS] m/z 338 (MH$^+$). |
| 91 | 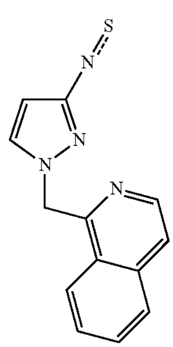 | 70 | $^1$H NMR (400 MHz, DMSO-d$_6$) δ ppm: 8.42 (d, 1H), 8.35 (d, 1H), 8.03 (d, 1H), 7.97 (d, 1H), 7.84 (d, 1H), 7.82 (m, 1H), 7.74 (m, 1H), 6.46 (d, 1H), 5.97 (s, 2H). [ES+ MS] m/z 267 (MH$^+$). |

TABLE 6-continued

| Int | Structure | Starting intermediate | Physical data |
|---|---|---|---|
| 92 | 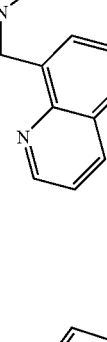 | 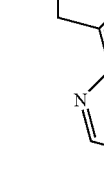  UKRORG SYN | $^1$H NMR (400 MHz, DMSO-d$_6$) δ ppm: 8.97 (dd, 1H), 8.42 (dd, 1H), 7.97 (m, 2H), 7.62-7.56 (m, 2H), 7.37 (d, 1H), 6.44 (d, 1H), 5.91 (s, 2H). [ES+ MS] m/z 267 (MH$^+$). |
| 93 | 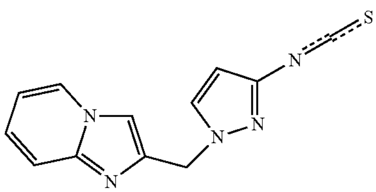 |   UKRORG SYN | $^1$H NMR (400 MHz, DMSO-d$_6$) δ ppm: 8.83 (d, 1H), 8.26 (s, 1H), 7.99 (d, 1H), 7.38-7.42 (m, 1H), 6.51 (d, 1H), 5.62 (s, 2H). [ES+ MS] m/z 256 (MH$^+$). |
| 94 | 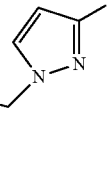 | 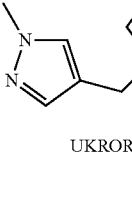  UKRORG SYN | $^1$H NMR (400 MHz, DMSO-d$_6$) δ ppm: 7.79 (d, 1H), 7.69 (s, 1H), 7.39 (s, 1H), 6.37 (d, 1H), 5.10 (s, 2H), 3.78 (s, 3H). [ES+ MS] m/z 219 (MH$^+$). |
| 95 | 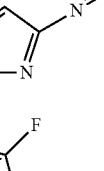 | 50 | $^1$H NMR (400 MHz, DMSO-d$_6$) δ ppm: 8.35-8.37 (m, 1H), 7.74-7.79 (m, 1H), 7.44-7.48 (m, 1H), 6.25 (s, 1H), 5.43 (m, 2H), 2.30 (s, 3H). [ES+ MS] m/z 249 (MH$^+$). |
| 96 | 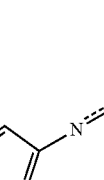 | 49 | $^1$H NMR (400 MHz, DMSO-d$_6$) δ ppm: 8.48 (d, 1H), 7.98-8.03 (m, 1H), 7.94 (d, 1H), 6.44 (d, 1H), 5.46 (d, 2H). [ES+ MS] m/z 253 (MH$^+$). |

TABLE 6-continued

| Int | Structure | Starting intermediate | Physical data |
|---|---|---|---|
| 97 | 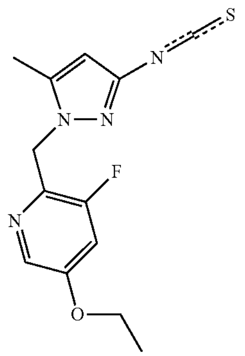 | 71 | $^1$H NMR (300 MHz, DMSO-d$_6$) δ ppm: 8.08-8.12 (m, 1H), 7.83-7.90 (m, 1H), 7.45-7.55 (m, 1H), 6.41-6.42 (m, 1H), 5.34-5.37 (m, 2H), 4.09-4.15 (m, 2H), 1.31-1.35 (m, 3H). [ES+ MS] m/z 279 (MH$^+$). |
| 98 | 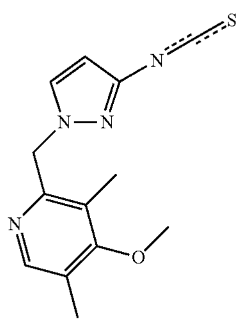 | UKRORG SYN | $^1$H NMR (300 MHz, DMSO-d$_6$) δ ppm: 8.56 (s, 1H), 8.04 (d, 1H), 6.49 (d, 1H), 5.60 (s, 2H), 2.35 (s, 3H), 2.24 (s, 3H). [ES+ MS] m/z 275 (MH$^+$). |
| 99 | 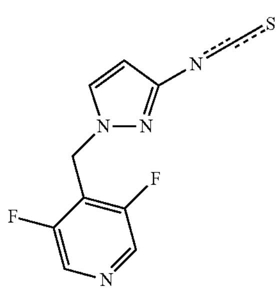 | 51 | $^1$H NMR (400 MHz, DMSO-d$_6$) δ ppm: 8.58 (s, 2H), 8.01 (d, 1H), 6.46 (d, 1H), 5.47 (s, 2H). [ES+ MS] m/z 253 (MH$^+$). |
| 100 | 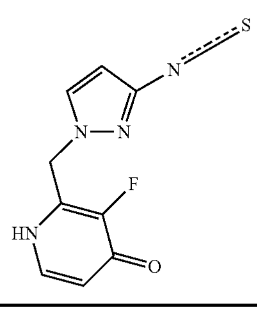 | 52 | $^1$H NMR (400 MHz, DMSO-d$_6$) δ ppm: 8.54 (d, 1H), 7.97 (d, 1H), 7.73 (t, 1H), 6.47 (d, 1H), 5.59 (m, 2H). [ES+ MS] m/z 251 (MH$^+$). |

(a) Crude was purified using silica gel cartridge with a linear gradient of hexane:EtOAc.

Intermediate 101: Ethyl 2-(3,5-dimethyl-1H-pyrazol-1-yl)propanoate

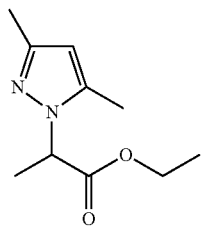

A suspension of 3,5-dimethyl-1H-pyrazole (ALDRICH, 8 g, 0.083 mol), anhydrous $K_2CO_3$ (ALDRICH, 11.50 g, 0.083 mol) and ethyl 2-bromopropanoate (ALDRICH, 15 g, 0.083 mol) in 50 mL of dry ACN was refluxed with mechanical stirring for 24 h. Reaction was checked by TLC (iodine), and starting material was detected. 0.2 equivalents of $K_2CO_3$ were added to the mixture which was refluxed over the weekend. Reaction was checked, starting material was still detected. 0.2 eq. of $K_2CO_3$ were added to the mixture, which was refluxed during 24 additional hours. Reaction mixture was filtered. Solvent was evaporated under reduced pressure. Residue was diluted with 50 ml of DCM, and washed with water. Organic layer was separated and aqueous fraction was extracted three times with 70 mL of DCM. Combined organic extracts were washed with brine, dried over $Na_2SO_4$ (anh), filtered and concentrated under reduce pressure. Residue was purified using a 70 g silica gel cartridge with a linear gradient of hexane/EtOAc 100/0 to 20/80 to yield the title compound (11.6 g 71%) as colourless oil. $^1$H NMR (300 MHz, $CDCl_3$) δ ppm: 5.83 (s, 1H), 4.85 (q, 1H), 4.08-4.25 (m, 2H), 2.22-2.23 (m, 6H), 1.79 (d, 3H), 1.23 (t, 3H).

Intermediate 102: 2-(3,5-dimethyl-1H-pyrazol-1-yl)propanohydrazide

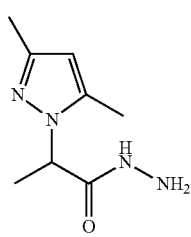

To a stirred solution of hydrazine hydrate (FLUKA, 0.397 mol, 17.25 mL) in 100 mL of 95% EtOH intermediate 101 (11.6 g, 0.066 mol) was added dropwise, previously dissolved in 60 mL of EtOH. Mixture of reaction was heated to 50° C. during 16 h. Reaction was followed by TLC (iodine). Solvent was eliminated in vacuum conditions to yield a white solid characterized as the title compound (10.7 g, 98%). $^1$H NMR (300 MHz, $CDCl_3$) δ ppm: 7.90 (br s, 1H), 5.85 (s, 1H), 4.80 (q, 1H), 3.82 (br s, 2H), 2.21-2.24 (m, 6H), 1.75 (d, 3H). [ES+MS] m/z 183 ($MH^+$).

Intermediate 103: Ethyl 3-amino-2-methyl-3-thioxopropanoate

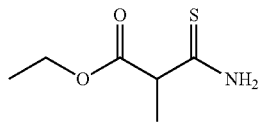

A mixture of diphenylphosphinodithioic acid (ALFAAESAR, 37.4 g, 149 mmol) and 2-cyanopropionic acid ethyl ester (ABCR, 9.90 mL, 74.7 mmol) in isopropanol (350 mL) was heated under reflux for 5 h. TLC (Hex:EtOAc 7:3) showed reaction had gone to completion. Reaction mixture was allowed to cool and was placed in the fridge overnight. Reaction mixture was filtered off and washed with isopropanol. Residue was partitioned between ethyl acetate (250 mL) and 1N NaOH (250 mL). Phases were separated and organic phase was washed with water (300 mL), brine (300 mL), dried over sodium sulfate and concentrated to dryness. Crude was purified by chromatography on silica gel using a hexane/EtOAc gradient. Appropriate fractions were combined and evaporated to yield title compound as a white solid (6.6 g, 40.9 mmol, 54.8% yield). $^1$H NMR (300 MHz, DMSO-$d_6$) δ ppm: 9.60 (s, 1H), 9.40 (s, 1H), 4.05 (q, 2H), 3.74 (q, 1H), 1.29 (d, 3H), 1.15 (t, 3H). [ES+MS] m/z 162 ($MH^+$).

Intermediate 104: Ethyl 2-(4-methyl-1,3-thiazol-2-yl)propanoate

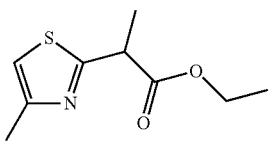

A mixture of Intermediate 103 (6.6 g, 40.9 mmol) and chloroacetone (FLUKA, 3.27 mL, 40.9 mmol) in DMF (50 mL) was stirred at 80° C. for 5 h. Reaction mixture was cooled to room temperature, treated with $NaHCO_3$ (150 mL) and extracted with ethyl ether (2×200 mL). Organic layer was washed with brine, dried over $Na_2SO_4$ and evaporated to give title compound (7.57 g, 38.0 mmol, 93% yield) as yellow oil. $^1$H NMR (300 MHz, DMSO-$d_6$) δ ppm: 7.19 (s, 1H), 4.23-4.06 (m, 3H), 2.31 (s, 3H), 1.48 (d, 3H), 1.16 (t, 3H). [ES+MS] m/z 200 ($MH^+$). It was subsequently observed that this compound undergoes autooxidation at the stereogenic centre to form ethyl 2-hydroxy-2-(4-methyl-1,3-thiazol-2-yl)propanoate. Once the presence of this compound had been observed, the compound was actively synthesised, hereinbelow described as Intermediate 106.

Intermediate 105: ethyl 2-bromo-2-(4-methyl-1,3-thiazol-2-yl)propanoate

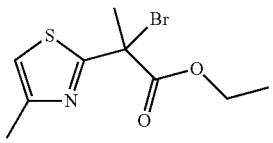

To a solution of Intermediate 104 (7.57 g, 38.0 mmol) in toluene (100 mL) was added hydrochloric acid (3.43 mL, 41.8 mmol). The mixture was kept at room temperature for 10 minutes. The mixture was cooled to 0° C. and potassium bromide (PANREAC, 4.97 g, 41.8 mmol) and hydrogen peroxide (4.59 mL, 49.4 mmol) were added. Reaction mixture was stirred at 0° C. for 3 hours and then was quenched with 1N $Na_2S_2O_3$ (150 mL) and saturated $NaHCO_3$ aqueous solution (150 mL). Organic phase was separated and the aqueous phase was extracted with EtOAc (2×150 mL). Combined organic layers were washed with brine, dried over sodium sulfate and concentrated to give the title compound (10.22 g, 36.7 mmol, 97% yield) as oil. $^1$H NMR (300 MHz, DMSO-$d_6$) δ ppm: 7.43 (m, 1H), 4.21-4.28 (q, 2H), 2.30-2.35 (m, 6H), 1.19-1.24 (m, 3H).

Intermediate 106: ethyl 2-hydroxy-2-(4-methyl-1,3-thiazol-2-yl)propanoate

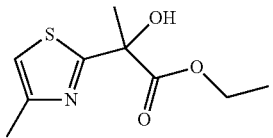

A mixture of Intermediate 105 (10.2 g, 36.7 mmol) and silver oxide (ALDRICH, 4.25 g, 18.33 mmol) in acetonitrile (112 mL) and water (28 mL) was stirred at room temperature overnight. Reaction mixture was filtered through a pad of Celite to remove solids, and the pad was washed with a 95:5 DCM-MeOH mixture (300 mL). The filtrate was concentrated to give 8 g of a brown residue. This batch was purified on 150 g of silica gel cartridge and was eluted with hexane-EtOAc, gradient 0-30%, to yield the title compound (4.14 g, 19.23 mmol, 52.4% yield) as yellow oil. $^1$H NMR (300 MHz, DMSO-$d_6$) δ ppm: 7.19 (m, 1H), 6.72 (s, 1H), 4.09 (q, 2H), 2.31-2.32 (m, 3H), 1.69 (s, 3H), 1.14 (t, 3H). [ES+MS] m/z 216 (MH$^+$).

Intermediate 107: 2-hydroxy-2-(4-methyl-1,3-thiazol-2-yl)propanohydrazide

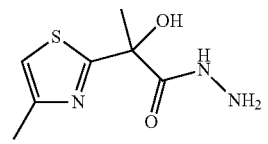

A solution of Intermediate 106 (4.14 g, 19.23 mmol) in EtOH (60 mL) was treated with hydrazine monohydrate (FLUKA, 9.35 mL, 192 mmol). Mixture was heated at reflux for 3 h. Reaction mixture was concentrated. Residue was triturated with a mixture of DCM/Hexane and finally ether, and was filtered. Crude was purified by silica gel chromatography using a linear gradient of DCM/MeOH (0-5%) as eluents to obtain the title compound (3 g, 14.91 mmol, 78% yield) as a white solid. $^1$H NMR (300 MHz, DMSO-$d_6$) δ ppm: 9.05 (br s, 1H), 7.16 (s, 1H), 6.59 (s, 1H), 4.23-4.25 (m, 2H), 2.32 (s, 3H), 1.67 (s, 3H). [ES+MS] m/z 202 (MH$^+$).

Intermediate 108: 2-(4-methyl-1,3-thiazol-2-yl)propanohydrazide

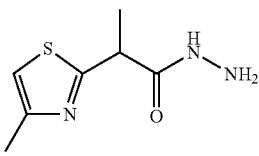

Preparation and characterization of intermediate 108 is described in PB63555P.

Intermediate 109: 1-[(2-methyl-1,3-thiazol-4-yl)methyl]-1H-indazol-3-amine

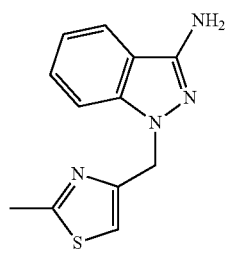 [SMILES: Cc1nc(Cn2nc(N)c3ccccc32)cs1]

A solution of 1H-indazol-3-amine (ABCR, 700 mg, 5.26 mmol) in anhydrous DMSO (10 ml) was added to a suspension of potassium hydroxide (PANREAC, 737 mg, 13.14 mmol) in anhydrous DMSO (40 mL) and this mixture was stirred for 10 min. A solution of 4-(chloromethyl)-2-methyl-1,3-thiazole hydrochloride (BUTTPARK, 776 mg, 5.26 mmol) and sodium hydride (ALDRICH, 126 mg, 5.26 mmol) in anhydrous DMSO (10 mL) was added dropwise to the mixture. Reaction was stirred at room temperature for 32 hours. Mixture of reaction was poured into water (100 mL) and extracted using DCM (4×100 mL). The combined organics were washed with water:brine (1:1) (100 mL) and dried over $MgSO_4$ (anh), filtered and concentrated to dryness. Residue was purified using silica chromatography column using a linear gradient of DCM/MeOH (0%->5%) as eluents to give the title compound 1-[(2-methyl-1,3-thiazol-4-yl)methyl]-1H-indazol-3-amine (988 mg, 4.04 mmol, 77% yield). $^1$H NMR (400 MHz, DMSO-$d_6$) δ ppm: 7.67-7.69 (m, 1H), 7.40-7.43 (m, 1H), 7.23-7.28 (m, 1H), 7.07 (s, 1H), 6.90-6.90 (m, 1H), 5.46 (br s, 2H), 5.31 (s, 2H), 2.57 (s, 3H). [ES+MS] m/z 245 (MH$^+$).

Intermediate 110 was prepared by methods analogous to that described for Intermediate 72 but replacing Intermediate 48 with that indicated in Table 7. Reaction time: from 20 minutes to 6 h. Other modifications are also indicated.

TABLE 7

| Int | Structure | Starting intermediate | Physical data |
|---|---|---|---|
| 110 | 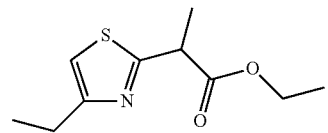 | 109 | ¹H NMR (400 MHz, DMSO-d$_6$) δ ppm: 7.84-7.86 (m, 1H), 7.74-7.76 (m, 1H), 7.50-7.54 (m, 1H), 7.41 (s, 1H), 7.27-7.31 (m, 1H), 5.65 (s, 2H), 2.56 (s, 3H). [ES+ MS] m/z 287 (MH$^+$). |

Intermediate 111: Ethyl 2-(4-ethyl-1,3-thiazol-2-yl)propanoate

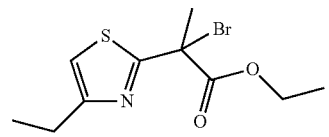

Prepared following same procedure as intermediate 104 but using 1-chloro-2-butanone (Ukrorg, 198 mg, 1.861 mmol) instead of chloroacetone and heating at reflux instead at 80° C. for 5 hours. Obtained title compound (340 mg (1.594 mmol, 86% yield) as a yellow oil. ¹H NMR (400 MHz, CDCl$_3$) δ ppm: 6.86 (s, 1H), 4.27 (q, 1H), 4.21 (q, 2H), 2.82 (q, 2H), 1.66 (d, 3H), 1.30 (t, 3H), 1.27 (t, 3H).

Intermediate 112: Ethyl 2-bromo-2-(4-ethyl-1,3-thiazol-2-yl)propanoate

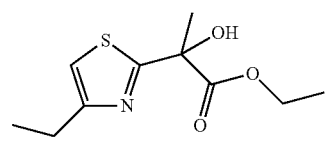

Prepared following same procedure as intermediate 105 but using as intermediate 111 (330 mg, 1.547 mmol). Obtained title compound (410 mg, 1.103 mmol, 91% yield) as a yellow oil. ¹H NMR (400 MHz, CDCl$_3$) δ ppm: 6.96 (s, 1H), 4.30 (q, 2H), 2.79 (q, 2H), 2.49 (s, 3H), 1.31 (t, 3H), 1.28 (t, 3H)

Intermediate 113: Ethyl 2-(4-ethyl-1,3-thiazol-2-yl)-2-hydroxypropanoate

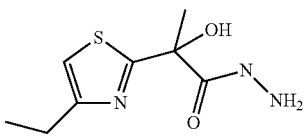

Prepared following same procedure as intermediate 106 but using intermediate 112 (400 mg, 1.369 mmol). After reacting for 24 h, added an extra drop of water to drive the reaction to completion and continued reacting at rt for 3 days. Obtained title compound (130 mg, 0.567 mmol, 41% yield) ¹H NMR (400 MHz, DMSO-d$_6$) δ ppm: 7.18 (s, 1H), 4.08 (q, 2H), 2.66 (q, 2H), 1.68 (s, 3H), 1.19-1.10 (m, 6H).

Intermediate 114: 2-(4-ethyl-1,3-thiazol-2-yl)-2-hydroxypropanohydrazide

Prepared following similar procedure to that of intermediate 107. Used intermediate 113 (120 mg, 0.523 mmol). After reacting with hydrazine monohydrate (0.127 mL, 2.62 mmol) at 60° C. overnight, reaction did not go to completion. For this reason added an extra amount of hydrazine monohydrate (0.127 mL, 2.62 mmol) at 60° C. for another 18 h. Reaction mixture was concentrated to yield title compound with no need of further purification. Obtained title compound (110 mg, 0.511 mmol, 98% yield)
¹H NMR (400 MHz, DMSO-d$_6$) δ ppm: 9.04 (br s, 1H), 7.16 (s, 1H), 6.58 (br s, 1H), 4.24 (br s, 2H), 2.67 (q, 2H), 1.67 (s, 3H), 1.19 (t, 3H).

EXAMPLES

Method A

Example 1

5-[1-(3,5-dimethyl-1H-pyrazol-1-yl)ethyl]-N-{1-[(6-methyl-2-pyridinyl)methyl]-1H-pyrazol-3-yl}-1,3,4-thiadiazol-2-amine

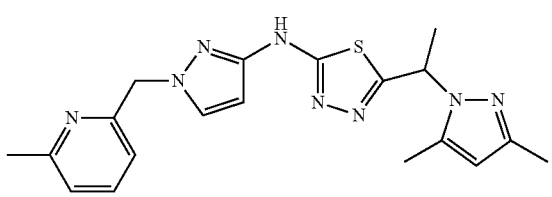

Intermediate 74 2-[(3-isothiocyanato-1H-pyrazol-1-yl)methyl]-6-methylpyridine (101 mg, 0.439 mmol) was dissolved in 4 mL of DCM, and then Intermediate 102 2-(3,5-dimethyl-1H-pyrazol-1-yl)propanohydrazide (80 mg, 0.439 mmol) was added. The mixture was stirred at room temperature for 2 h. Solvent was evaporated under vacuum to give 2-[2-(3,5-dimethyl-1H-pyrazol-1-yl)propanoyl]-N-{1-[(6-methyl-2-pyridinyl)methyl]-1H-pyrazol-3-yl}hydrazinecarbothioamide (181 mg, 0.439 mmol, 100% yield) as yellow solid. [ES+MS] m/z 413 (MH$^+$)]. Solid was dissolved in 5 mL of POCl$_3$ and the mixture was stirred at 100° C., until no starting material was detected (1 h 30 minutes). Crude of reaction was partitioned between DCM and distilled water. Organic layer was dried over MgSO$_4$ (anh), filtered and concentrated to give a light yellow solid. This solid was purified by HPLC preparative using X-Terra chromatography column (30 mm×150 mm), gradient 0% to 40% ACN/H$_2$O, in neutral conditions to yield the title compound as a white solid (22 mg, 12.7%). $^1$H NMR (300 MHz, DMSO-d$_6$) δ ppm: 10.87 (br s, 1H), 7.77 (d, 1H), 7.59-7.65 (m, 1H), 7.15-7.17 (m, 1H), 6.77-6.80 (m, 1H), 6.01 (d, 1H), 5.83 (br s, 1H), 5.77 (q, 1H), 5.26 (s, 2H), 2.45 (s, 3H), 2.24 (s, 3H), 2.08 (s, 3H), 1.78 (d, 3H). [ES+MS] m/z 395 (MH$^+$).

Examples 2-5 were prepared by methods analogous to that described for Example 1, replacing isothiocyanate and hydrazide intermediates 74 and 102 with those indicated in Table 1. Modifications in the purification step are also indicated.

TABLE 1

| Ex. | Structure | Isothiocyanate intermediate | Hydrazide intermediate | Physical data |
|---|---|---|---|---|
| 2 | 5-[1-(3,5-dimethyl-1H-pyrazol-1-yl)ethyl]-N-{1-[(3-fluoro-4-methyl-2-pyridinyl)methyl]-1H-pyrazol-3-yl}-1,3,4-thiadiazol-2-amine See footnote b) | 79 0.322 mmol | 102 0.354 mmol | $^1$H NMR (300 MHz, DMSO-d$_6$) δ ppm: 10.82 (br s, 1H), 8.20 (d, 1H), 7.71 (d, 1H), 7.32 (t, 1H), 5.95 (d, 1H), 5.82 (s, 1H), 5.75 (q, 1H), 5.32 (d, 2H), 2.39 (br s, 3H), 2.23 (s, 3H), 2.09 (s, 3H), 1.77 (d, 3H). [ES+ MS] m/z 413 (MH$^+$). |
| 3 | N-{1-[(3-fluoro-4-methyl-2-pyridinyl)methyl]-1H-pyrazol-3-yl}-5-[1-(3-methyl-1H-pyrazol-1-yl)ethyl]-1,3,4-thiadiazol-2-amine See footnote e) | 79 0.262 mmol | 0.288 mmol ARTCHEM | $^1$H NMR (300 MHz, DMSO-d$_6$) δ ppm: 10.84 (br s, 1H), 8.20 (d, 1H), 7.72-7.74 (m, 2H), 7.31-7.35 (m, 1H), 6.05 (d, 1H), 5.96 (d, 1H), 5.82 (q, 1H), 5.33 (d, 2H), 2.30 (br s, 3H), 2.16 (s, 3H), 1.81 (d, 2H). [ES+ MS] m/z 399 (MH$^+$). |
| 4 | 5-[1-(3,5-dimethyl-1H-pyrazol-1-yl)ethyl]-N-[1-(3-pyridinylmethyl)-1H-pyrazol-3-yl]-1,3,4-thiadiazol-2-amine See footnote c) | 76 0.564 mmol | 102 0.564 mmol | $^1$H NMR (300 MHz, DMSO-d$_6$) δ ppm: 10.88 (br s, 1H), 8.49-8.51 (m, 2H), 7.78 (d, 1H), 7.63-7.67 (m, 1H), 7.33-7.38 (m, 1H), 5.97 (d, 1H), 5.85 (s, 1H), 5.78 (q, 1H), 5.26 (s, 2H), 2.25 (s, 3H), 2.11 (s, 3H), 1.79 (d, 3H). [ES+ MS] m/z 381 (MH$^+$). |
| 5 | 5-[1-(3,5-dimethyl-1H-pyrazol-1-yl)ethyl]-N-[1-(2-pyridinylmethyl)-1H-pyrazol-3-yl]-1,3,4-thiadiazol-2-amine See footnote d) | 75 1.013 mmol | 102 1.013 mmol | $^1$H NMR (300 MHz, DMSO-d$_6$) δ ppm: 8.51-8.53 (m, 1H), 7.72-7.79 (m, 2H), 7.28-7.33 (m, 1H), 7.02-7.05 (m, 1H), 6.01 (d, 1H), 5.83 (s, 1H), 5.76 (q, 1H), 5.31 (s, 2H), 2.23 (s, 3H), 2.08 (s, 3H), 1.78 (d, 3H). [ES+ MS] m/z 381 (MH$^+$). |

TABLE 1-continued

| Ex. | Structure | Isothiocyanate intermediate | Hydrazide intermediate | Physical data |
|---|---|---|---|---|
| 6 | 5-[1-(3,5-dimethyl-1H-pyrazol-1-yl)ethyl]-N-{1-[(3-fluoro-2-pyridinyl)methyl]-1H-pyrazol-3-yl}-1,3,4-thiadiazol-2-amine<br>See footnote a) and d). | 77<br>0.692 mmol | 102<br>0.692 mmol | $^1$H NMR (300 MHz, DMSO-d$_6$) δ ppm: 10.81 (br s, 1H), 8.35-8.37 (m, 1H), 7.68-7.75 (m, 2H), 7.42-7.48 (m, 1H), 5.96 (d, 1H), 5.84 (s, 1H), 5.74 (q, 1H), 5.33-5.37 (m, 2H), 2.23 (s, 3H), 2.09 (s, 3H), 1.77 (d, 3H). [ES+ MS] m/z 399 (MH$^+$). |
| 7 | 5-[1-(3,5-dimethyl-1H-pyrazol-1-yl)ethyl]-N-{1-[(2-fluoro-3-pyridinyl)methyl]-1H-pyrazol-3-yl}-1,3,4-thiadiazol-2-amine<br>See footnote a) and d). | 73<br>0.194 mmol | 102<br>0.194 mmol | $^1$H NMR (300 MHz, DMSO-d$_6$) δ ppm: 10.89 (br s, 1H), 8.17-8.19 (m, 1H), 7.78 (d, 1H), 7.67-7.74 (m, 1H), 7.30-7.35 (m, 1H), 5.99 (d, 1H), 5.83 (s, 1H), 5.76 (q, 1H), 5.28 (s, 2H), 2.23 (s, 3H), 2.09 (s, 3H), 1.78 (d, 3H). [ES+ MS] m/z 399 (MH$^+$). |
| 8 | N-{1-[(5-chloro-6-methyl-3-pyridinyl)methyl]-1H-pyrazol-3-yl}-5-[1-(3,5-dimethyl-1H-pyrazol-1-yl)ethyl]-1,3,4-thiadiazol-2-amine<br>See footnote e) | 80<br>0.317 mmol | 102<br>0.317 mmol | $^1$H NMR (300 MHz, DMSO-d$_6$) δ ppm: 10.89 (br s, 1H), 8.34 (d, 1H), 7.78 (d, 1H), 7.75 (d, 1H), 5.97 (d, 1H), 5.74-5.82 (m, 2H), 5.33 (br s, 2H), 2.51 (s, 3H), 2.24 (s, 3H), 2.09 (s, 3H), 1.79 (d, 3H). [ES+ MS] m/z 429 (MH$^+$). |
| 9 | N-{1-[(3,5-dichloro-2-pyridinyl)methyl]-1H-pyrazol-3-yl}-5-[1-(3,5-dimethyl-1H-pyrazol-1-yl)ethyl]-1,3,4-thiadiazol-2-amine<br>See footnote e) | 81<br>0.077 mmol | 102<br>0.077 mmol | $^1$H NMR (300 MHz, CDCl$_3$) δ ppm: 9.55 (br s, 1H), 8.42 (d, 1H), 7.75 (d, 1H), 7.42 (d, 1H), 6.08 (d, 1H), 5.81 (s, 1H), 5.70 (q, 2H), 5.41 (s, 2H), 2.27 (s, 3H), 2.26 (s, 3H), 1.98 (d, 3H). [ES+ MS] m/z 449 (MH$^+$). |

TABLE 1-continued

| Ex. | Structure | Isothiocyanate intermediate | Hydrazide intermediate | Physical data |
|---|---|---|---|---|
| 10 | N-{1-[(2-fluoro-3-pyridinyl)methyl]-1H-pyrazol-3-yl}-5-[1-(3-methyl-1H-pyrazol-1-yl)ethyl]-1,3,4-thiadiazol-2-amine<br>See footnote e) | 73<br>0.201 mmol | 0.201 mmol<br>ARTCHEM | $^1$H NMR (300 MHz, DMSO-d$_6$) δ 10.89 (br s, 1H), 8.18 (d, 1H), 7.78 (d, 1H), 7.65-7.74 (m, 2H), 7.30-7.35 (m, 1H), 6.06 (d, 1H), 5.99 (d, 1H), 5.82 (q, 1H), 5.28 (s, 2H), 2.15 (s, 3H), 1.81 (d, 3H). [ES+ MS] m/z 385 (MH$^+$). |
| 11 | 5-[1-(3,5-dimethyl-1H-pyrazol-1-yl)ethyl]-N-(1-{[2-(ethyloxy)-3-pyridinyl]methyl}-1H-pyrazol-3-yl)-1,3,4-thiadiazol-2-amine<br>See footnote a) and d) | 78<br>0.269 mmol | 102<br>0.269 mmol | $^1$H NMR (300 MHz, DMSO-d$_6$) δ ppm: 10.86 (br s, 1H), 8.07-8.09 (m, 1H), 7.70 (d, 1H), 7.28-7.31 (m, 1H), 6.89-6.93 (m, 1H), 5.96 (d, 1H), 5.82 (s, 1H), 5.76 (q, 1H), 5.14 (s, 2H), 4.31 (q, 2H), 2.23 (s, 3H), 2.08 (s, 3H), 1.78 (d, 3H), 1.30 (t, 3H). [ES+ MS] m/z 425 (MH$^+$). | a) Residue was purified by flash chromatography DCM/MeOH (0-20%).
b) Residue was purified by HPLC preparative using X-Terra column (30 × 150 mm), linear gradient 25%-100% ACN/H$_2$O (0.1% NH$_4$NCO$_3$).
c) Residue was purified by HPLC preparative using SunFire column (19 × 150 mm) linear gradient 20%-100% ACN/H$_2$O, in neutral conditions.
d) Residue was purified by HPLC preparative using X-Terra column (19 × 150 mm) or (30 × 150 mm) linear gradient 25%-100% ACN/H$_2$O, in neutral conditions.
e) Residue was purified by HPLC preparative using X-Bridge column (30 × 150 mm) linear gradient 25%-100% ACN/H$_2$O (0.1% NH$_4$HCO$_3$).

Method B

Example 12

1-[5-({1-[(3,5-difluoro-2-pyridinyl)methyl]-1H-pyrazol-3-yl}amino)-1,3,4-thiadiazol-2-yl]-1-(4-methyl-1,3-thiazol-2-yl)ethanol

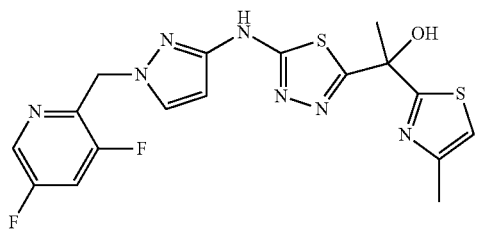 [SMILES: Cc1csc(C(C)(O)c2nnc(Nc3ccn(Cc4ncc(F)cc4F)n3)s2)n1]

A mixture of Intermediate 107, 2-hydroxy-2-(4-methyl-1,3-thiazol-2-yl)propanohydrazide (63 mg, 0.313 mmol), and Intermediate 96, 3,5-difluoro-2-[(3-isothiocyanato-1H-pyrazol-1-yl)methyl]pyridine (79 mg, 0.313 mmol) in dichloromethane (anh) (3 mL) was stirred at room temperature overnight. Reaction mixture was concentrated, residue was treated with sulfuric acid (2 mL, 0.364 mmol) and stirred at room temperature during 1 h. Resulting mixture was neutralized with 32% NH$_3$ (aq) under ice-bath until pH was basic. Mixture was partitioned between DCM (3×15 mL) and water (15 mL). Organic phase was separated, dried over magnesium sulfate and concentrated. Residue was purified by preparative HPLC using SUNFIRE column (C18, 3.5 μm, 19×150 mm) and linear gradient 25% to 75% water (0.1% HCOOH)—(0.1% HCOOH). Appropriate fractions were collected to give 1-[5-({1-[(3,5-difluoro-2-pyridinyl)methyl]-1H-pyrazol-3-yl}amino)-1,3,4-thiadiazol-2-yl]-1-(4-methyl-1,3-thiazol-2-yl)ethanol (50 mg, 0.109 mmol, 30.0% yield) as a white solid. $^1$H NMR (400 MHz, DMSO-d$_6$) δ ppm: 10.83 (s, 1H), 8.46 (d, 1H), 7.93-7.98 (m, 1H), 7.74 (d, 1H), 7.27 (s, 1H), 7.21 (m, 1H), 5.96 (d, 1H), 5.37 (d, 2H), 2.29 (d, 3H), 1.97 (s, 1H). [ES+MS] m/z 436 (MH$^+$).

Examples 13-36 were prepared by methods analogous to that described for Example 1 replacing isothiocyanate and hydrazide intermediates 96 and 107 with those indicated in Table 2. When the method used for purification was different from that for Example 13, it is indicated.

TABLE 2

| Ex. | Structure | Isothiocyanate intermediate | Hydrazide intermediate | Physical data |
|---|---|---|---|---|
| 13 | 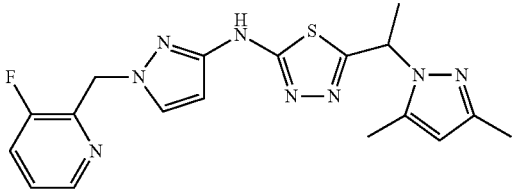<br>N-{1-[(3-fluoro-2-pyridinyl)methyl]-1H-pyrazol-3-yl}-5-[1-(3-methyl-1H-pyrazol-1-yl)ethyl]-1,3,4-thiadiazol-2-amin<br>See footnote c) | 77<br>0.427 mmol | 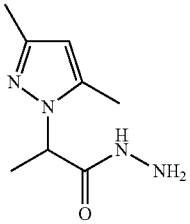<br>0.427 mmol<br>ARTCHEM | $^1$H NMR (300 MHz, DMSO-d$_6$) δ ppm: 8.35-8.37 (m, 1H), 7.69-7.75 (m, 3H), 7.42-7.48 (m, 1H), 6.07 (d, 1H), 5.97 (d, 1H), 5.81 (q, 1H), 5.34-5.38 (m, 2H), 2.16 (s, 3H), 1.80 (d, 3H). [ES+ MS] m/z 385 (MH$^+$). |
| 14 | 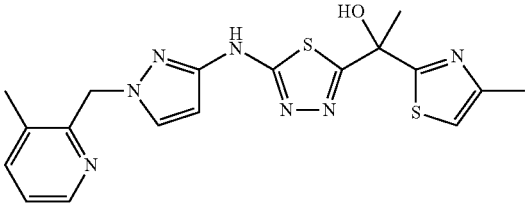 [SMILES: Cc1csc(C(C)(O)c2nnc(Nc3ccn(Cc4ncccc4C)n3)s2)n1]<br>1-[5-({1-[(3-methyl-2-pyridinyl)methyl]-1H-pyrazol-3-yl}amino)-1,3,4-thiadiazol-2-yl]-1-(4-methyl-1,3-thiazol-2-yl)ethanol<br>See footnote a) | 87<br>0.204 mmol | 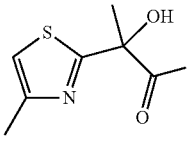<br>107<br>0.204 mmol | $^1$H NMR (300 MHz, DMSO-d$_6$) δ ppm: 10.82 (br s, 1H), 8.31 (d, 1H), 7.63 (d, 1H), 7.58 (d, 1H), 7.23 (m, 2H), 5.89 (d, 1H), 5.29 (s, 2H), 2.37 (s, 3H), 2.29 (s, 3H), 1.97 (s, 3H). [ES+ MS] m/z 414 (MH$^+$). |
| 15 | 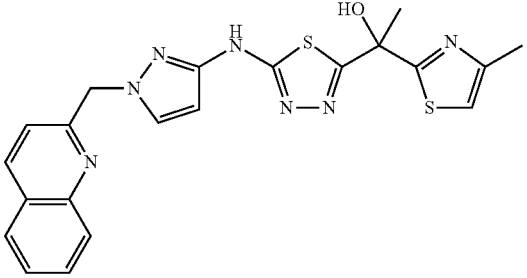 [SMILES: Cc1csc(C(C)(O)c2nnc(Nc3ccn(Cc4ccc5ccccc5n4)n3)s2)n1]<br>1-(4-methyl-1,3-thiazol-2-yl)-1-(5-{[1-(2-quinolinylmethyl)-1H-pyrazol-3-yl]amino}-1,3,4-thiadiazol-2-yl)ethanol<br>See footnote b) | 88<br>0.248 mmol | 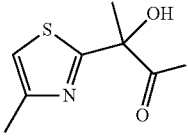<br>107<br>0.248 mmol | $^1$H NMR (300 MHz, DMSO-d$_6$) δ ppm: 10.90 (br s, 1H), 8.30 (d, 1H), 7.97 (t, 2H), 7.86 (d, 1H), 7.77 (t, 1H), 7.60 (t, 1H), 7.26 (s, 1H), 7.15 (m, 2H), 6.03 (d, 1H), 5.51 (d, 2H), 2.26 (s, 3H), 1.95 (s, 3H). [ES+ MS] m/z 450 (MH$^+$). |
| 16 | 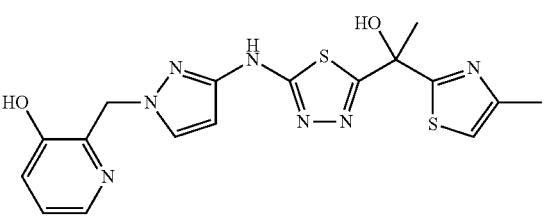 [SMILES: Cc1csc(C(C)(O)c2nnc(Nc3ccn(Cc4ncccc4O)n3)s2)n1]<br>2-{[3-({5-[1-hydroxy-1-(4-methyl-1,3-thiazol-2-yl)ethyl]-1,3,4-thiadiazol-2-yl}amino)-1H-pyrazol-1-yl]methyl}-3-pyridinol<br>See footnote c) | 89<br>0.034 mmol | 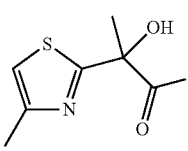<br>107<br>0.034 mmol | $^1$H NMR (300 MHz, CDCl$_3$) δ ppm: 8.11 (d, 1H), 7.65 (d, 1H), 7.51 (m, 2H), 6.89 (s, 1H), 6.31 (d, 1H), 5.69 (s, 2H), 2.42 (s, 3H), 2.05 (s, 3H). [ES+ MS] m/z 416 (MH$^+$). |

TABLE 2-continued

| Ex. | Structure | Isothiocyanate intermediate | Hydrazide intermediate | Physical data |
|---|---|---|---|---|
| 17 | 1-[5-({1-[(2-amino-1,3-thiazol-4-yl)methyl]-1H-pyrazol-3-yl}amino)-1,3,4-thiadiazol-2-yl]-1-(4-methyl-1,3-thiazol-2-yl)ethanol<br>See footnote a) | 90<br>0.184 mmol | 107<br>0.184 mmol | $^1$H NMR (400 MHz, DMSO-d$_6$) δ ppm: 10.82 (s, 1H), 7.59 (d, 1H), 7.30 (s, 1H), 7.19 (s, 1H), 6.95 (br s, 2H), 6.31 (s, 1H), 5.93 (d, 1H), 4.95 (s, 2H), 2.29 (s, 3H), 1.97 (s, 3H). [ES+ MS] m/z 421 (MH$^+$). |
| 18 | 1-[5-({1-[(6-fluoro-2-pyridinyl)methyl]-1H-pyrazol-3-yl}amino-1,3,4-thiadiazol-2-yl]-1-(4-methyl-1,3-thiazol-2-yl)ethanol<br>See footnote a) | 72<br>0.192 mmol | 107<br>0.192 mmol | $^1$H NMR (300 MHz, CDCl$_3$) δ ppm: 7.74 (q, 1H), 7.45 (d, 1H), 6.93 (d, 1H), 6.84-6.94 (m, 3H), 6.15 (d, 1H), 5.28 (s, 2H), 2.41 (s, 3H), 2.09 (s, 3H). [ES+ MS] m/z 418 (MH$^+$). |
| 19 | 1-(5-{[1-(1-isoquinolinylmethyl)-1H-pyrazol-3-yl]amino}-1,3,4-thiadiazol-2-yl)-1-(4-methyl-1,3-thiazol-2-yl)ethanol<br>See footnote a) | 91<br>0.357 mmol | 107<br>0.357 mmol | $^1$H NMR (400 MHz, DMSO-d$_6$) δ ppm: 10.82 (s, 1H), 8.51 (d, 1H), 8.43 (d, 1H), 7.98 (d, 1H), 7.74-7.81 (m, 3H), 7.64 (t, 1H), 7.27 (s, 1H), 7.22 (s, 1H), 5.91 (d, 1H), 5.84 (d, 2H), 2.29 (s, 3H), 1.96 (s, 3H). [ES+ MS] m/z 450 (MH$^+$). |
| 20 | 1-(4-methyl-1,3-thiazol-2-yl)-1-(5-{[1-(8-quinolinylmethyl)-1H-pyrazol-3-yl]amino}-1,3,4-thiadiazol-2-yl)ethanol<br>See footnote a) | 92<br>0.582 mmol | 107<br>0.582 mmol | $^1$H NMR (400 MHz, DMSO-d$_6$) δ ppm: 10.85 (s, 1H), 8.97 (dd, 1H), 8.40 (dd, 1H), 7.93 (dd, 1H), 7.76 (d, 1H), 7.59 (dd, 1H), 7.53 (t, 1H), 7.28 (d, 1H), 7.25 (s, 1H), 7.19 (d, 1H), 5.97 (d, 1H), 5.85 (s, 2H), 2.26 (s, 3H), 1.95 (s, 3H). [ES+ MS] m/z 450 (MH$^+$). |

TABLE 2-continued

| Ex. | Structure | Isothiocyanate intermediate | Hydrazide intermediate | Physical data |
|---|---|---|---|---|
| 21 | 1-(4-methyl-1,3-thiazol-2-yl)-1-[5-({1-[(2-methyl-1,3-thiazol-4-yl)methyl]-1H-pyrazol-3-yl}amino)-1,3,4-thiadiazol-2-yl]ethanol See footnote a) | 85<br>2.332 mmol | 107<br>2.332 mmol | $^1$H NMR (300 MHz, DMSO-d$_6$) δ ppm: 7.66 (d, 1H), 7.29 (d, 1H), 7.24 (s, 1H), 7.19 (d, 1H), 5.95 (d, 1H), 5.23 (s, 2H), 2.60 (s, 3H), 2.29 (d, 3H), 1.97 (s, 3H). [ES+ MS] m/z 420 (MH$^+$). |
| 22 | 1-[5-({1-[(5-methyl-3-isoxazolyl)methyl]-1H-pyrazol-3-yl}amino)-1,3,4-thiadiazol-2-yl]-1-(4-methyl-1,3-thiazol-2-yl)ethanol See footnote a) | 86<br>0.590 mmol | 107<br>0.649 mmol | $^1$H NMR (300 MHz, DMSO-d$_6$) δ ppm: 7.74 (d, 1H), 7.32 (s, 1H), 7.20 (m, 1H), 6.05 (s, 1H), 5.96 (d, 1H), 5.26 (s, 2H), 2.34 (s, 3H), 2.29 (s, 3H), 1.98 (s, 3H). [ES+ MS] m/z 404 (MH$^+$). |
| 23 | 5-[1-(3-methyl-1H-pyrazol-1-yl)ethyl]-N-{1-[(2-methyl-1,3-thiazol-4-yl)methyl]-1H-pyrazol-3-yl}-1,3,4-thiadiazol-2-amine See footnote a) | 85<br>0.846 mmol | 0.849 mmol<br>ARTCHEM | $^1$H NMR (300 MHz, DMSO-d$_6$) δ ppm: 10.87 (br s, 1H), 7.75 (d, 1H), 7.68 (d, 1H), 7.25 (s, 1H), 6.05 (d, 1H), 5.97 (d, 1H), 5.84 (q, 1H), 5.23 (s, 2H), 2.61 (s, 3H), 2.16 (s, 3H), 1.82 (d, 3H). [ES+ MS] m/z 387 (MH$^+$). |
| 24 | 1-(5-{[1-(imidazo[1,2-a]pyridin-2-ylmethyl)-1H-pyrazol-3-yl]amino}-1,3,4-thiadiazol-2-yl)-1-(4-methyl-1,3-thiazol-2-yl)ethanol See footnote d) | 93<br>0.286 mmol | 107<br>0.286 mmol | $^1$H NMR (400 MHz, DMSO-d$_6$) δ ppm: 10.87 (br s, 1H), 8.50 (d, 1H), 7.77 (s, 1H), 7.71 (d, 1H), 7.49-7.51 (m, 1H), 7.29 (s, 1H), 7.23-7.27 (m, 1H), 7.19 (m, 1H), 6.88-6.91 (m, 1H), 5.96 (d, 1H), 5.33 (s, 2H), 2.29 (m, 3H), 1.98 (s, 3H). [ES+ MS] m/z 439 (MH$^+$). |

TABLE 2-continued

| Ex. | Structure | Isothiocyanate intermediate | Hydrazide intermediate | Physical data |
|---|---|---|---|---|
| 25 | 1-[5-({1-[(1-methyl-1H-pyrazol-4-yl)methyl]-1H-pyrazol-3-yl}amino)-1,3,4-thiadiazol-2-yl]-1-(4-methyl-1,3-thiazol-2-yl)ethanol<br>See footnote f) | 94<br>0.547 mmol | 107<br>0.547 mmol | $^1$H NMR (400 MHz, DMSO-d$_6$) δ ppm: 10.82 (br s, 1H), 7.63 (s, 1H), 7.57 (d, 1H), 7.38 (m, 1H), 7.30 (s, 1H), 7.20 (m, 1H), 5.88 (d, 1H), 5.03 (s, 2H), 3.77 (s, 3H), 2.30 (m, 3H), 1.98 (s, 3H). [ES+ MS] m/z 403 (MH$^+$). |
| 26 | 1-[5-({1-[(3,5-dimethyl-4-isoxazolyl)methyl]-1H-pyrazol-3-yl}amino)-1,3,4-thiadiazol-2-yl]-1-(4-methyl-1,3-thiazol-2-yl)ethanol<br>See footnote e) | 84<br>0.213 mmol | 107<br>0.235 mmol | $^1$H NMR (300 MHz, DMSO-d$_6$) δ ppm: 10.90 (br s, 1H), 7.72 (d, 1H), 7.28 (s, 1H), 7.23 (m, 1H), 5.86 (d, 1H), 5.02 (s, 2H), 2.42 (s, 3H), 2.31 (s, 3H), 2.19 (s, 3H), 1.99 (s, 3H). [ES+ MS] m/z 418 (MH$^+$). |
| 27 | N-{1-[(3,5-dimethyl-4-isoxazolyl)methyl]-1H-pyrazol-3-yl}-5-[1-(3-methyl-1H-pyrazol-1-yl)ethyl]-1,3,4-thiadiazol-2-amine<br>See footnote e) | 84<br>0.213 mmol | 0.235 mmol<br>ARTCHEM | $^1$H NMR (300 MHz, DMSO-d$_6$) δ ppm: 10.91 (s, 1H), 7.72-7.77 (m, 2H), 6.07 (d, 1H), 5.81-5.88 (m, 2H), 5.00 (s, 2H), 2.41 (s, 3H), 2.18 (s, 6H), 1.82 (d, 3H). [ES+ MS] m/z 385 (MH$^+$). |
| 28 | 1-[5-({1-[(3-fluoro-2-pyridinyl)methyl]-5-methyl-1H-pyrazol-3-yl}amino)-1,3,4-thiadiazol-2-yl]-1-(4-methyl-1,3-thiazol-2-yl)ethanol<br>See footnote b) | 95<br>0.342 mmol | 107<br>0.342 mmol | $^1$H NMR (400 MHz, DMSO-d$_6$) δ ppm: 10.73 (s, 1H), 8.34-8.36 (m, 1H), 7.69-7.74 (m, 1H), 7.41-7.45 (m, 1H), 7.25 (s, 1H), 7.21 (m, 1H), 5.78 (s, 1H), 5.31-5.32 (m, 2H), 2.29 (m, 6H), 1.96 (s, 3H). [ES+ MS] m/z 432 (MH$^+$). |

TABLE 2-continued

| Ex. | Structure | Isothiocyanate intermediate | Hydrazide intermediate | Physical data |
|---|---|---|---|---|
| 29 | N-{1-[(3-fluoro-2-pyridinyl)methyl]-5-methyl-1H-pyrazol-3-yl}-5-[1-(3-methyl-1H-pyrazol-1-yl)ethyl]-1,3,4-thiadiazol-2-amine<br>See footnote b) | 95<br>0.342 mmol | 0.342 mmol<br>ARTCHEM | $^1$H NMR (400 MHz, DMSO-d$_6$) δ ppm: 10.75 (s, 1H), 8.34-8.35 (m, 1H), 7.68-7.73 (m, 2H), 7.40-7.45 (m, 1H), 6.05 (d, 1H), 5.77-5.82 (m, 2H), 5.29 (d, 2H), 2.29 (s, 3H), 2.15 (s, 3H), 1.79 (d, 3H). [ES+ MS] m/z 399 (MH$^+$). |
| 30 | 1-{5-[(1-{[5-(ethyloxy)-3-fluoro-2-pyridinyl]methyl}-1H-pyrazol-3-yl)amino]-1,3,4-thiadiazol-2-yl}-1-(4-methyl-1,3-thiazol-2-yl)ethanol<br>See footnote c) | 97<br>0.269 mmol | 107<br>0.269 mmol | $^1$H NMR (400 MHz, DMSO-d$_6$) δ ppm: 10.80 (s, 1H), 8.05-8.10 (m, 1H), 7.62-7.67 (m, 1H), 7.39-7.50 (m, 1H), 7.26-7.27 (m, 1H), 7.19-7.20 (m, 1H), 5.90-5.93 (m, 1H), 5.24-5.26 (m, 2H), 4.08-4.14 (m, 2H), 2.28-2.29 (m, 3H), 1.96 (s, 3H), 1.32-1.36 (m, 3H). [ES+ MS] m/z 462 (MH$^+$). |
| 31 | 1-{5-[(1-{[3,5-dimethyl-4-(methyloxy)-2-pyridinyl]methyl}-1H-pyrazol-3-yl)amino]-1,3,4-thiadiazol-2-yl}-1-(4-methyl-1,3-thiazol-2-yl)ethanol<br>See footnote c) | 98<br>0.663 mmol | 107<br>0.663 mmol | $^1$H NMR (400 MHz, DMSO-d$_6$) δ ppm: 10.84 (s, 1H), 8.15 (s, 1H), 7.63 (d, 1H), 7.26 (s, 1H), 7.21 (m, 1H), 5.87 (d, 1H), 5.25 (s, 2H), 3.69 (s, 3H), 2.30 (s, 6H), 2.18 (s, 3H), 1.98 (s, 3H). [ES+ MS] m/z 458 (MH$^+$). |

TABLE 2-continued

| Ex. | Structure | Isothiocyanate intermediate | Hydrazide intermediate | Physical data |
|---|---|---|---|---|
| 32 | 1-[5-({1-[(3,5-difluoro-4-pyridinyl)methyl]-1H-pyrazol-3-yl}amino)-1,3,4-thiadiazol-2-yl]-1-(4-methyl-1,3-thiazol-2-yl)ethanol<br>See footnote c) | 99<br>0.297 mmol | 107<br>0.297 mmol | $^1$H NMR (400 MHz, DMSO-$d_6$) δ ppm: 10.88 (s, 1H), 8.54 (s, 2H), 7.80 (d, 1H), 7.26 (s, 1H), 7.23 (m, 1H), 5.95 (d, 1H), 5.37 (s, 2H), 2.30 (d, 3H), 1.97 (s, 3H). [ES+ MS] m/z 436 (MH$^+$). |
| 33 | 3-fluoro-2-{[3-({5-[1-hydroxy-1-(4-methyl-1,3-thiazol-2-yl)ethyl]-1,3,4-thiadiazol-2-yl}amino)-1H-pyrazol-1-yl]methyl}-4(1H)-pyridinone<br>See footnote c) | 100<br>0.139 mmol | 107<br>0.139 mmol | $^1$H NMR (400 MHz, DMSO-$d_6$) δ ppm: 10.85 (br s, 1H), 8.14 (s, 1H), 7.70 (m, 2H), 7.29 (s, 1H), 7.20 (m, 1H), 6.0 (br s, 1H), 5.26 (s, 2H), 2.30 (m, 3H), 1.98 (s, 3H). [ES+ MS] m/z 434 (MH$^+$). |
| 34 | N-{1-[(3-fluoro-2-[pyridinyl)methyl]-1H-pyrazol-3-yl}-5-[1-(4-methyl-1,3-thiazol-2-yl)ethyl]-1,3,4-thiadiazol-2-amine<br>See footnote a) | 77<br>0.427 mmol | 108<br>0.427 mmol | $^1$H NMR (300 MHz, DMSO-$d_6$) δ ppm: 10.82 (br s, 1H), 8.35-8.37 (m, 1H), 7.68-7.75 (m, 2H), 7.41-7.47 (m, 1H), 7.19-7.22 (m, 1H), 5.97-5.98 (m, 1H), 5.37 (s, 2H), 4.87 (q, 1H), 2.33 (s, 3H), 1.70 (d, 3H). [ES+ MS] m/z 402 (MH$^+$). |
| 35 | 5-[1-(3,5-dimethyl-1H-pyrazol-1-yl)ethyl]-N-{1-[1-(3-fluoro-2-pyridinyl)ethyl]-1H-pyrazol-3-yl}-1,3,4-thiadiazol-2-amine<br>See footnote c) | 82<br>0.246 mmol | 102<br>0.246 mmol | $^1$H NMR (300 MHz, DMSO-$d_6$) δ ppm: 10.79 (br s, 1H), 8.37-8.39 (m, 1H), 7.75-7.77 (m, 1H), 7.65-7.72 (m, 1H), 7.40-7.46 (m, 1H), 5.97 (d, 1H), 5.70-5.84 (m, 3H), 2.23 (d, 3H), 2.10 (s, 3H), 1.76-1.80 (m, 6H). [ES+ MS] m/z 413 (MH$^+$). |

TABLE 2-continued

| Ex. | Structure | Isothiocyanate intermediate | Hydrazide intermediate | Physical data |
|---|---|---|---|---|
| 36 | 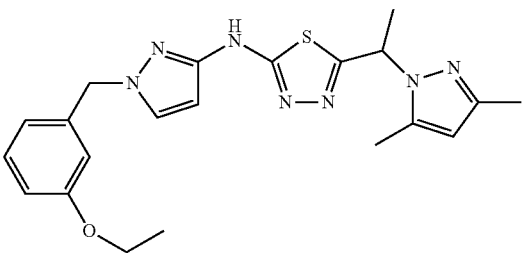 [SMILES: CCOc1cccc(Cn2ccc(Nc3nnc(C(C)n4nc(C)cc4C)s3)n2)c1]<br>5-[1-(3,5-dimethyl-1H-pyrazol-1-yl)ethyl]-N-(1-{[6-(ethyloxy)-2-pyridinyl]methyl}-1H-pyrazol-3-yl)-1,3,4-thiadiazol-2-amine<br>See footnote c) | 83<br>0.764 mmol | 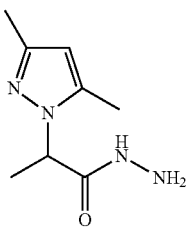<br>102<br>0.764 mmol | $^1$H NMR (300 MHz, CDCl$_3$) δ ppm: 10.03 (br s, 1H), 7.40-7.52 (m, 2H), 6.59-6.62 (m, 2H), 6.10-6.12 (m, 1H), 5.69-5.79 (m, 2H), 5.19 (br s, 2H), 4.32 (q, 2H), 2.27 (s, 3H), 2.23 (s, 3H), 1.98 (d, 3H), 1.37 (t, 3H). [ES+ MS] m/z 425 (MH$^+$). |

(a) Residue was purified by flash chromatography DCM/MeOH (0-20%).
(b) Residue was triturated with ethyl ether and resulting solid was filtered and washed with ethyl ether and water.
(c) Residue was purified by HPLC preparative using X-Bridge column (19 × 150 mm) or (30 × 150 mm) linear gradient 10%-100% or linear gradient 25%-100% (25_100) ACN/H$_2$O (0.1% NH$_4$HCO$_3$).
(d) Residue was purified by HPLC preparative using X-Bridge column (30 × 150 mm) linear gradient 10%-100% ACN (0.1% HCOOH)/H$_2$O (0.1% HCOOH).
(e) Residue was purified by HPLC preparative using X-Terra column (10 × 150 mm) linear gradient 20%-100% ACN/H$_2$O (0.1% NH$_4$HCO$_3$).
(f) Purification of crude was not needed.

Method C

Example 37

1-[5-({1-[(3-fluoro-4-methyl-2-pyridinyl)methyl]-1H-pyrazol-3-yl}amino)-1,3,4-thiadiazol-2-yl]-1-(4-methyl-1,3-thiazol-2-yl)ethanol

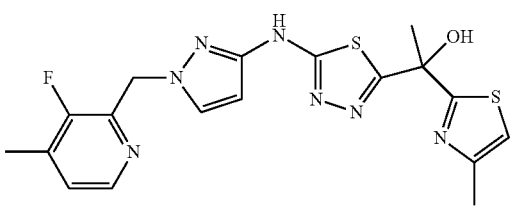 [SMILES: Cc1csc(C(C)(O)c2nnc(Nc3ccn(Cc4nccc(C)c4F)n3)s2)n1]

A mixture of Intermediate 107, 2-hydroxy-2-(4-methyl-1,3-thiazol-2-yl)propanohydrazide (82 mg, 0.407 mmol), and Intermediate 79, 3-fluoro-2-[(3-isothiocyanato-1H-pyrazol-1-yl)methyl]-4-methylpyridine (84 mg, 0.340 mmol) in ethanol (6 mL) was heated under reflux for 3 h. Reaction mixture was concentrated and residue was treated with sulfuric acid (2 mL, 37.5 mmol) at 0° C., and the resulting mixture was allowed to reach room temperature overnight. Reaction mixture was placed in an ice-bath and treated slowly and dropwise with 37% aq. NH$_3$ (10 mL) until pH was basic. Mixture was diluted with water and ethyl acetate (60 mL). Organic phase was separated, washed with brine, dried over sodium sulfate and concentrated. Crude was loaded on a silica cartridge and eluted with a linear gradient, 0-5% MeOH-DCM, affording 100 mg (68.3% yield) of the title compound. $^1$H NMR (300 MHz, DMSO-d$_6$) δ ppm: 10.81 (s, 1H), 8.19 (d, 1H), 7.71 (s, 1H), 7.33-7.31 (m, 1H), 7.27 (s, 1H), 7.19 (s, 1H), 5.93 (s, 1H), 5.33 (s, 2H), 2.28 (br s, 6H), 1.96 (s, 3H). [ES+MS] m/z 432 (MH$^+$).

Example 38

1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol

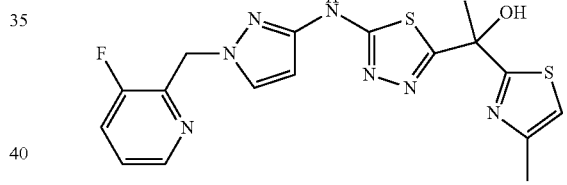

Title compound was prepared by a method analogous to that described for Example 37, replacing Intermediate 79 with Intermediate 77 (106 mg, 0.453 mmol) to yield the title compound (45 mg, 0.109 mmol, 24% yield). Example 38 was also prepared replacing conditions of EtOH at reflux by DCM at room temperature to yield (11.15 g, 25.6 mmol, quantitative yield). $^1$H NMR (300 MHz, DMSO-d$_6$) δ ppm: 10.81 (s, 1H), 8.36 (d, 1H), 7.74-7.68 (m, 2H), 7.47-7.41 (m, 1H), 7.26 (s, 1H), 7.20 (s, 1H), 5.95 (s, 1H), 5.37 (s, 2H), 2.28 (s, 3H), 1.96 (s, 3H). [ES+MS] m/z 418 (MH$^+$).

Chiral Separation of Racemate Example 13.

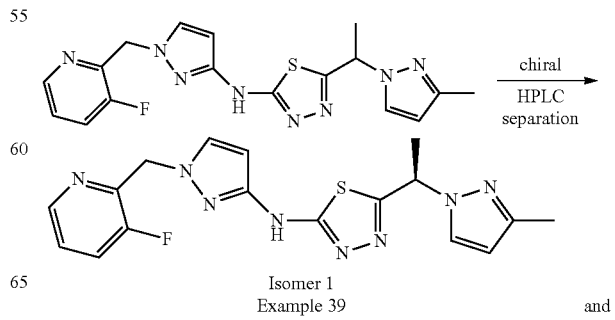

Isomer 1
Example 39 and

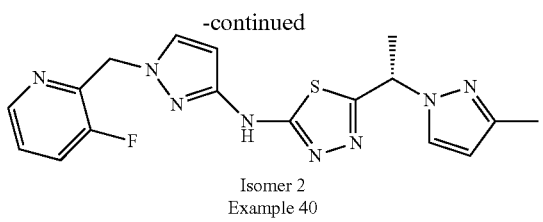

Isomer 2
Example 40

545 mg of Example 13 (racemic mixture) were separated using an isocratic mixture of hexane/ethanol 80:20 with a CHIRALPAK-IA 50×500 mm column, F=50 mL/min, 254 nm. Separation was achieved in one injection and appropriate fractions were collected to afford both enantiomers:

Example 39

N-{1-[(3-fluoro-2-pyridinyl)methyl]-1H-pyrazol-3-yl}-5-[(1R)-1-(3-methyl-1H-pyrazol-1-yl)ethyl]-1,3,4-thiadiazol-2-amine Isomer 1

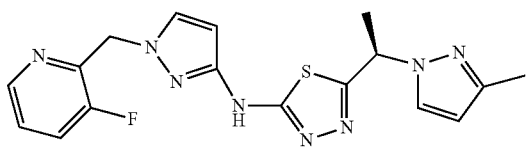

Isomer 1, first elution in HPLC: 199 mg, light orange solid. $^1$H NMR (400 MHz, DMSO-$d_6$) δ ppm: 10.83 (br s, 1H), 8.35-8.37 (m, 1H), 7.69-7.75 (m, 3H), 7.43-7.47 (m, 1H), 6.07 (d, 1H), 5.97 (d, 1H), 5.81 (q, 1H), 5.34-5.39 (m, 2H), 2.16 (s, 3H), 1.80 (d, 3H). [ES+MS] m/z 385 (MH$^+$). Analytical chiral HPLC conditions: CHIRALPAK-IA 4.6×150 mm column, method: eluent isocratic mixture hexane/ethanol 80/20, flow: 1 mL/min. RT: 18.66 min. [α]$_D$=−11.18° (2.04, MeOH). The absolute configuration was determined by ab initio vibrational circular dichroism (VCD).

Example 40

N-{1-[(3-fluoro-2-pyridinyl)methyl]-1H-pyrazol-3-yl}-5-[(1S)-1-(3-methyl-1H-pyrazol-1-yl)ethyl]-1,3,4-thiadiazol-2-amine Isomer 2

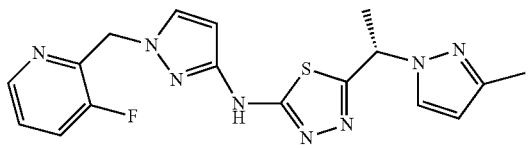

Isomer 2, second elution in HPLC: 262 mg, pale cream solid. $^1$H NMR (400 MHz, DMSO-$d_6$) δ ppm: 10.83 (br s, 1H), 8.35-8.37 (m, 1H), 7.69-7.75 (m, 3H), 7.43-7.47 (m, 1H), 6.06 (d, 1H), 5.96 (d, 1H), 5.81 (q, 1H), 5.34-5.39 (m, 2H), 2.16 (s, 3H), 1.80 (d, 3H). [ES+MS] m/z 385 (MH$^+$). Analytical chiral HPLC conditions: CHIRALPAK-IA 4.6×150 mm column, method: eluent isocratic mixture hexane/ethanol 80/20, flow: 1 mL/min. RT: 30.60 min. [α]$_D$=+11.28° (2.04, MeOH). The absolute configuration was determined by ab initio vibrational circular dichroism (VCD).

Chiral Separation of Racemate Example 38.

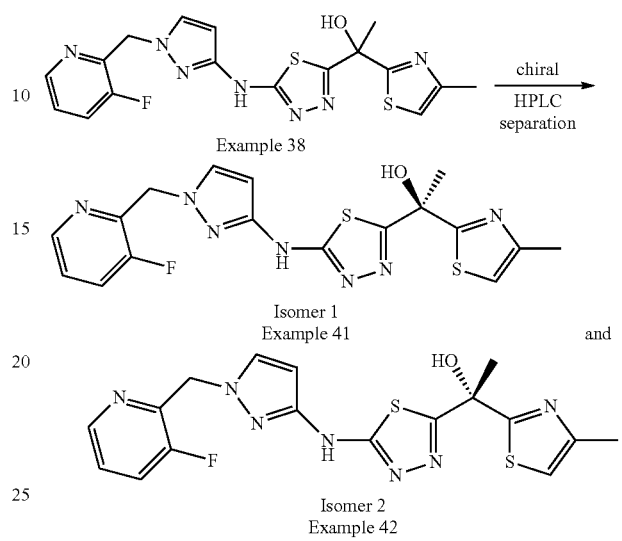

Example 38

Isomer 1
Example 41 and

Isomer 2
Example 42

162 mg of Example 38 (racemic mixture) were separated using a CHIRALPAK-AD 20×250 mm column, F=17 mL/min, 254 nm and an isocratic mixture of ACN, 0.1% isopropylamine-(MeOH-iPrOH 60:40), 0.1% isopropylamine 92:8. Product was dissolved in 8 mL of methanol/acetonitrile 1:1 (HPLC grade). Separation was achieved after 5 injections and appropriate fractions were collected to afford both enantiomers:

Example 41

(1S)-1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol Isomer 1

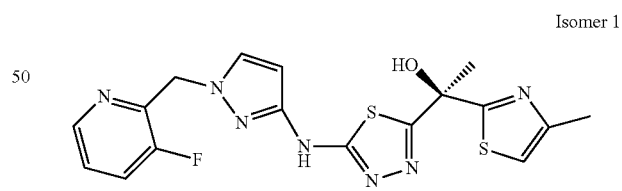

Isomer 1, first elution in HPLC: 70.5 mg, white solid. $^1$H NMR (300 MHz, DMSO-$d_6$) δ ppm: 10.82 (br s, 1H), 8.36 (d, 1H), 7.68-7.75 (m, 2H), 7.41-7.47 (m, 1H), 7.17-7.31 (m, 2H), 5.96 (d, 1H), 5.34-5.39 (m, 2H), 2.29 (br s, 3H), 1.96 (d, 3H). [ES+MS] m/z 418 (MH$^+$). Analytical chiral HPLC conditions: CHIRALPAK-AD 4.6×150 mm column, method: eluent isocratic mixture ACN 0.1% isoprylamine/MeOH 0.1% isopropylamine ratio 90/10, flow: 1 mL/min. RT: 4.83 min. [α]$_D$=+86.3° (2.02, MeOH). The absolute configuration was determined by ab initio vibrational circular dichroism (VCD).

Example 42

(1R)-1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol

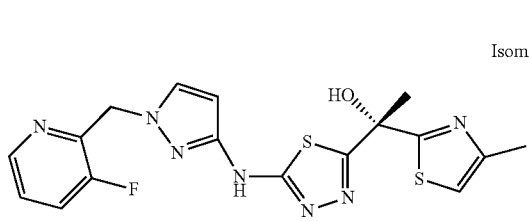

Isomer 2

Isomer 2, second elution in HPLC: 71 mg, white solid. $^1$H NMR (300 MHz, DMSO-d$_6$) δ ppm: 10.82 (br s, 1H), 8.36 (d, 1H), 7.68-7.75 (m, 2H), 7.41-7.47 (m, 1H), 7.17-7.31 (m, 2H), 5.96 (d, 1H), 5.34-5.39 (m, 2H), 2.28 (br s, 3H), 1.96 (d, 3H). [ES+MS] m/z 418 (MH$^+$).

Analytical chiral HPLC conditions: CHIRALPAK-AD 4.6×150 mm column, method: eluent isocratic mixture ACN 0.1% isoprylamine/MeOH 0.1% isopropylamine ratio 90/10, flow: 1 mL/min. RT: 8.08 min. [α]$_D$=−60.9° (2.1, MeOH). The absolute configuration was determined by ab initio vibrational circular dichroism (VCD).

Chiral Separation of Racemate Example 21.

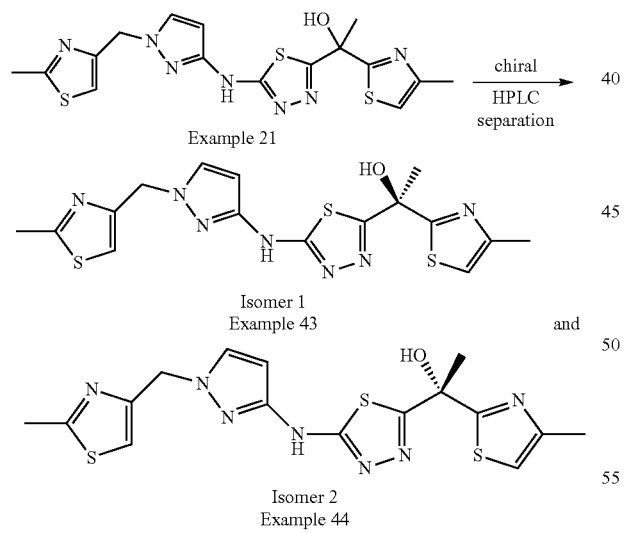

3.15 g of Example 21 (racemic mixture) were separated using a CHIRALPAK-IA 5×50 cm column, particle size 20 micron, F=50 mL/min, 254 nm and an isocratic mixture of ACN:[(MeOH (60)/IPA(40)] 95:5. Product was dissolved in 10 mL of a mixture of DCM/MeOH (HPLC grade). Separation was achieved after 7 injections and appropriate fractions were collected to afford both enantiomers:

Example 43

(1S)-1-(4-methyl-1,3-thiazol-2-yl)-1-[5-({1-[(2-methyl-1,3-thiazol-4-yl)methyl]-1H-pyrazol-3-yl}amino)-1,3,4-thiadiazol-2-yl]ethanol

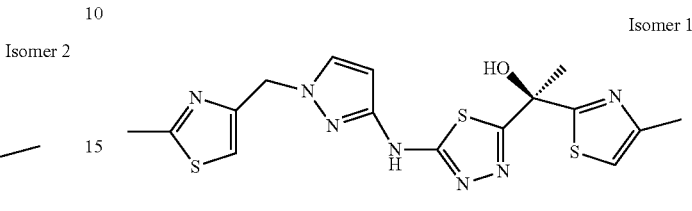

Isomer 1

Isomer 1, first elution in HPLC: 1.5 g, white solid. $^1$H NMR (400 MHz, DMSO-d$_6$) δ ppm: 10.81 (br s, 1H), 7.67 (d, 1H), 7.30 (s, 1H), 7.25 (s, 1H), 7.20 (m, 1H), 5.96 (d, 1H), 5.24 (s, 2H), 2.61 (s, 3H), 2.30 (d, 3H), 1.98 (s, 3H). [ES+MS] m/z 420 (MH$^+$). Analytical chiral HPLC conditions: CHIRALPAK-AD 4.6×150 mm column, method: eluent isocratic mixture hexane:ethanol ratio 80:20, flow: 1 mL/min. RT: 22.10 min. [α]$_D$=+119° (1, MeOH). The absolute configuration was determined by ab initio vibrational circular dichroism (VCD).

Example 44

(1R)-1-(4-methyl-1,3-thiazol-2-yl)-1-[5-({1-[(2-methyl-1,3-thiazol-4-yl)methyl]-1H-pyrazol-3-yl}amino)-1,3,4-thiadiazol-2-yl]ethanol

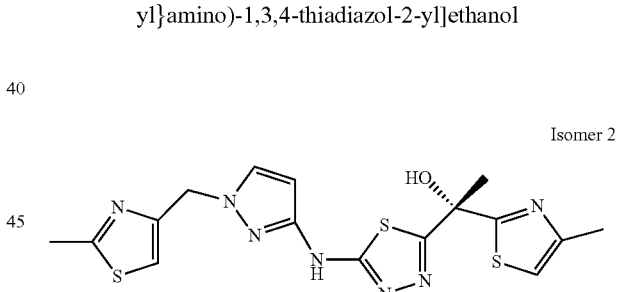

Isomer 2

Isomer 2, second elution in HPLC: 1.2 g, white solid. $^1$H NMR (400 MHz, DMSO-d$_6$) δ ppm: 10.86 (br s, 1H), 7.67 (d, 1H), 7.30 (s, 1H), 7.25 (s, 1H), 7.20 (m, 1H), 5.96 (d, 1H), 5.24 (s, 2H), 2.61 (s, 3H), 2.30 (d, 3H), 1.98 (s, 3H). [ES+MS] m/z 420 (MH$^+$). Analytical chiral HPLC conditions: CHIRALPAK-AD 4.6×150 mm column, method: eluent isocratic mixture hexane:ethanol ratio 80:20, flow: 1 mL/min. RT: 28.95 min. [α]$_D$=−147° (1, MeOH). The absolute configuration was determined by ab initio vibrational circular dichroism (VCD).

Examples 45 and 46 were prepared by methods analogous to that described for Example 13 replacing isothiocyanate and hydrazide intermediates 96 and 107 with those indicated in Table 2. When the method used for purification was different from that for Example 13, it is indicated.

| # | Structure | | Reagent | Product | NMR |
|---|---|---|---|---|---|
| 45 | 1-(4-methyl-1,3-thiazol-2-yl)-1-[5-({1-[(2-methyl-1,3-thiazol-4-yl)methyl]-1H-indazol-3-yl}amino)-1,3,4-thiadiazol-2-yl]ethanol<br>See footnote a | | 110<br>1.641 mmol | 107<br>1.641 mmol | $^1$H NMR (400 MHz, DMSO-d$_6$) δ ppm: 11.75 (br s, 1H), 8.07-8.09 (m, 1H), 7.60-7.62 (m, 1H), 7.38-7.43 (m, 2H), 7.21-7.22 (m, 1H), 7.17 (s, 1H), 7.09 (m, 1H), 5.54 (s, 2H), 2.56 (s, 3H), 2.02 (br s, 3H). [ES+ MS] m/z 470 (MH$^+$). |
| 46 | N-{5-[1-(3-methyl-1H-pyrazol-1-yl)ethyl]-1,3,4-thiadiazol-2-yl}-1-[(2-methyl-1,3-thiazol-4-yl)methyl]-1H-indazol-3-amine<br>See footnote a | | 110<br>1.571 mmol | 1.571 mmol<br>ARTCHEM | $^1$H NMR (400 MHz, DMSO-d$_6$) δ ppm: 11.79 (br s, 1H), 8.05-8.08 (m, 1H), 7.78 (d, 1H), 7.60-7.62 (m, 1H), 7.39-7.43 (m, 1H), 7.17 (s, 1H), 7.08-7.12 (m, 1H), 6.07 (d, 1H), 5.91 (q, 1H), 5.53 (s, 2H), 2.57 (s, 3H), 2.17 (s, 3H), 1.87 (d, 3H). [ES+ MS] m/z 437 (MH$^+$). |

(a) Residue was purified by flash chromatography DCM/MeOH (0-5%) and solid obtained was washed with ethyl ether.

Example 47

1-(4-ethylthiazol-2-yl)-1-(5-((1-((2-methylthiazol-4-yl)methyl)-1H-pyrazol-3-yl)amino)-1,3,4-thiadiazol-2-yl)methanol Prepared by methods analogous to that described for Example 37 using isothiocyanate intermediate 85 (71.4 mg, 0.302 mmol) and hydrazide intermediate 114 (65 mg, 0.302 mmol). Obtained title compound 72.7 mg, 0.168 mmol, 56% yield)

$^1$H-NMR, (400 MHz, DMSO-d$_6$) δ ppm: 10.83 (s, 1H) 7.66 (s, 1H), 7.27 (s, 1H), 7.23 (s, 1H), 7.19 (s, 1H), 5.95 (d, 1H), 5.23 (s, 2H), 2.65 (q, 2H), 2.60 (s, 3H), 1.97 (s, 3H), 1.16 (t, 3H) [ES MS] m/z 434 (MH$^+$)

Biological Activity

Mycobacterium tuberculosis H37Rv Inhibition Assay (Whole Cell Assay)

The measurement of the minimum inhibitory concentration (MIC) for each tested compound was performed in 96 wells flat-bottom, polystyrene microtiter plates. Ten two-fold drug dilutions in neat DMSO starting at 400 μM were performed. Five μl of these drug solutions were added to 95 μl of Middlebrook 7H9 medium. (Lines A-H, rows 1-10 of the plate layout). Isoniazid was used as a positive control, 8 two-fold dilution of Isoniazid starting at 160 μg/ml was prepared and 5 μl of this control curve was added to 95 μl of Middlebrook 7H9 medium (Difco catalogue ref. 271310). (Row 11, lines A-H). 5 μl of neat DMSO were added to row 12 (growth and Blank controls).

The inoculum was standardised to approximately 1×10$^7$ cfu/ml and diluted 1 in 100 in Middlebrook 7H9 broth (Middlebrook ADC enrichment, a dehydrated culture media which supports growth of mycobacterial species available from Becton Dickinson Catalogue Ref. 211887), to produce the final inoculum of H37Rv strain (ATCC25618). One hundred μl of this inoculum was added to the entire plate but G-12 and H-12 wells (Blank controls). All plates were placed in a sealed box to prevent drying out of the peripheral wells and they were incubated at 37° C. without shaking for six days. A resazurin solution was prepared by dissolving one tablet of resazurin (Resazurin Tablets for Milk Testing; Ref 330884Y VWR International Ltd) in 30 ml sterile PBS (phosphate buffered saline). 25 μl of this solution was added to each well. Fluorescence was measured (Spectramax M5 Molecular Devices, Excitation 530 nm, Emission 590 nm) after 48 hours to determine the MIC value.

Results of the *Mycobacterium tuberculosis* H37Rv Inhibition Assay (Whole Cell Assay)

All Examples were tested in the whole cell assay.

Examples 14, 18, 21, 38, 41, 43 and 47 described hereinabove were found to have an MIC value of 1 μM or less. For example, Example 43 was found to have an MIC value of 0.4 μM.

Examples 2, 6, 12, 13, 15, 20, 28, 29, 34, 37 and 40 described hereinabove were found to have an MIC value of 4 µM or less, but above Examples 7, 19 and 22-24 described hereinabove were found to have an MIC value of 10 µM or less, but above 4 µM.

Examples 1, 3-5, 8-11, 16, 17, 25-27, 30-33, 35, 36, 39, 42, 44, 45 and 46 described hereinabove were found to have an MIC value of greater than 10 µM.

In one aspect, compounds of the invention have an MIC value of 4 µM or less in the *Mycobacterium tuberculosis* H37Rv Inhibition Assay (Whole Cell Assay).

*Mycobacterium tuberculosis* InhA Inhibition Assay (Enzyme Assay)

InhA is able to reduce 2-trans enoyl-CoA esters with concomitant oxidation of NADH to $NAD^+$. The assay format is based on the kinetic detection of NADH consumption.

Assay for InhA inhibition is carried out with *mycobacterium* recombinant protein expressed and purified form *E. coli*. Standard assay conditions for the determination of kinetic constants and inhibitors activity use 5 nM of InhA, 50 µM of Dodecenoyl-CoA synthesized and purified as described by Quémard et al (DDCoA) and 50 µM of NADH as substrates, and it is carried out in 30 mM PIPES buffer pH 6.8, containing 0.05% of BSA. Solutions of compounds to be tested are prepared in 100% DMSO; eight one-third dilutions starting at 25 (or 1 µM for the most potent compounds) were made for doses-response curves. Triclosan is used as positive control in every experiment. One µl of compounds is added to the wells containing 25 µl of the DDCoA+NADH mix, the reaction is started by adding 50 µl of the enzyme solution. Fluorescence from NADH is followed at room temperature during 20 minutes in a fluorescent plate reader (excitation at 340 nM; emission at 480 nM). $IC_{50}$ values are determined using initial velocities of NADH consumption.

Quémard A, Sacchettini J C, Dessen A, et al. Enzymatic characterization of the target for isoniazid in *Mycobacterium tuberculosis*. Biochemistry 1995; 34:8235-41.

Results of the *Mycobacterium tuberculosis* InhA Inhibition Assay (Enzyme Assay)

All Examples other than Example 16 were tested in the enzyme assay.

Examples 1-4, 6-9, 14, 13-15, 18-21, 28, 29, 34-38, 40, 41, 43 and 47 described hereinabove were found to have an $IC_{50}$ value of less than or equal to 0.05 µg/ml. For example, Example 14 was found to have an $IC_{50}$ value of 0.004 µg/ml.

Examples 10, 12 and 22-24, described hereinabove were found to have an $IC_{50}$ value of less than 0.10 µg/ml but more than 0.05 µg/ml.

Examples 5, 17, 25, 30, 31, 39, 42, 44 and 45 described hereinabove were found to have an $IC_{50}$ value of less than 0.50 µg/ml but more than 0.10 µg/ml.

Examples 11, 26, 27, 32, 33 and 46 described hereinabove was found to have an $IC_{50}$ value of greater than 0.50 µg/ml.

In one aspect, compounds of the invention have an $IC_{50}$ value of less than 0.05 µg/ml in the *Mycobacterium tuberculosis* InhA Inhibition Assay (Enzyme Assay).

All publications, including but not limited to patents and patent applications cited in this specification are herein incorporated by reference as if each individual publication were specifically and individually indicated to be incorporated by reference as though fully set forth.

The application of which this description and claims forms part may be used as a basis for priority in respect of any subsequent application. The claims of such subsequent application may be directed to any feature or combination of features described herein.

They may take the form of product, composition, process, or use claims and may include, by way of example and without limitation, the following claims:

1. The compound (1S)-1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol, or a pharmaceutically acceptable salt thereof.

2. The compound: (1S)-1-[5-({1-[(3-fluoro-2-pyridinyl)methyl]-1H-pyrazol-3-yl}amino)-1,3,4-thiadiazol-2-yl]-1-(4-methyl-1,3-thiazol-2-yl)ethanol.

3. A compound according to claim 1, for use in therapy.

4. A compound according to claim 1, for use in the treatment of tuberculosis.

5. A method of treatment of tuberculosis in mammal, which method comprises the administration to a mammal in need of such treatment an effective amount of a compound or a pharmaceutically acceptable salt thereof according to claim 1.

6. A pharmaceutical composition comprising a compound according to claim 1, and one or more pharmaceutically acceptable carriers, excipients or diluents.

7. The method of claim 5 wherein said mammal is human.

* * * * *